United States Patent
Lee et al.

(10) Patent No.: US 10,538,510 B2
(45) Date of Patent: Jan. 21, 2020

(54) COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

(71) Applicants: SAMSUNG SDI CO., LTD., Yongin-si, Gyeonggi-do (KR); SAMSUNG ELECTRONICS CO., LTD, Suwon-si, Gyeonggi-do (KR)

(72) Inventors: Hanill Lee, Suwon-si (KR); Jun Seok Kim, Suwon-si (KR); Chang Ju Shin, Suwon-si (KR); Dongkyu Ryu, Suwon-si (KR); Eun Sun Yu, Suwon-si (KR); Sung-Hyun Jung, Suwon-si (KR); Sujin Han, Suwon-si (KR)

(73) Assignees: Samsung SDI Co., Ltd., Yongin-Si, Gyeonggi-do (KR); Samsung Electronics Co., Ltd., Suwon-Si, Gyeonggi-do (KR)

( * ) Notice: Subject to any disclaimer, the term of this patent is extended or adjusted under 35 U.S.C. 154(b) by 0 days.

(21) Appl. No.: 15/788,136

(22) Filed: Oct. 19, 2017

(65) Prior Publication Data
US 2018/0155325 A1 Jun. 7, 2018

(30) Foreign Application Priority Data
Dec. 2, 2016 (KR) .................. 10-2016-0163667

(51) Int. Cl.
| | | |
|---|---|---|
| *C07D 403/04* | (2006.01) | |
| *H01L 51/00* | (2006.01) | |
| *C07D 495/04* | (2006.01) | |
| *C07D 403/10* | (2006.01) | |
| *H01L 51/50* | (2006.01) | |

(52) U.S. Cl.
CPC ......... *C07D 403/04* (2013.01); *C07D 403/10* (2013.01); *C07D 495/04* (2013.01); *H01L 51/0067* (2013.01); *H01L 51/0071* (2013.01); *H01L 51/0072* (2013.01); *H01L 51/5016* (2013.01)

(58) Field of Classification Search
CPC .. C07D 403/04; C07D 403/10; C07D 495/04; H01L 51/0072; H01L 51/0067; H01L 51/0071; H01L 51/5016
USPC .................................. 428/690; 252/500, 582
See application file for complete search history.

(56) References Cited

U.S. PATENT DOCUMENTS

| | | | |
|---|---|---|---|
| 2012/0168731 A1* | 7/2012 | Schildknecht | C07D 235/02 257/40 |
| 2017/0069849 A1* | 3/2017 | Lee | H01L 51/0072 |
| 2017/0162795 A1* | 6/2017 | Molaire | H01L 51/5012 |
| 2017/0213985 A1* | 7/2017 | Lee | C09K 11/06 |
| 2018/0102485 A1* | 4/2018 | Mizutani | C07D 405/14 |

FOREIGN PATENT DOCUMENTS

| | | | |
|---|---|---|---|
| KR | 10-1074193 B | | 10/2011 |
| KR | 10-2012-0038056 | | 4/2012 |
| KR | 20120038056 A | * | 4/2012 |
| KR | 10-2012-0072784 A | | 7/2012 |
| KR | 10-1196093 B | | 11/2012 |
| KR | 10-1219481 B | | 1/2013 |
| KR | 10-2015-0226776 | | 10/2015 |
| KR | 10-1603070 B | | 3/2016 |

OTHER PUBLICATIONS

CAS reg. No. 1374446-01-1, May 24, 2012. (Year: 2012).*

* cited by examiner

*Primary Examiner* — Douglas J McGinty
(74) *Attorney, Agent, or Firm* — Lee & Morse, P.C.

(57) ABSTRACT

Disclosed are a compound for an organic optoelectronic device represented by Chemical Formula 1, a composition for an organic optoelectronic device, an organic optoelectronic device including the same, and a display device. Details of Chemical Formula 1 are the same as defined in the specification.

14 Claims, 1 Drawing Sheet

[FIG. 1]
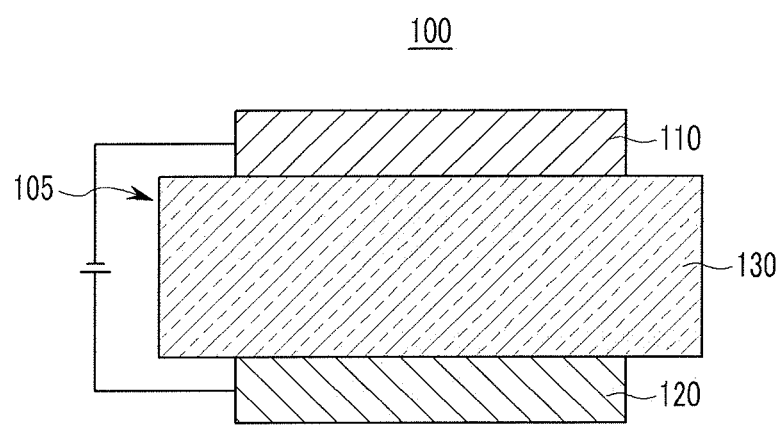
[FIG. 2]
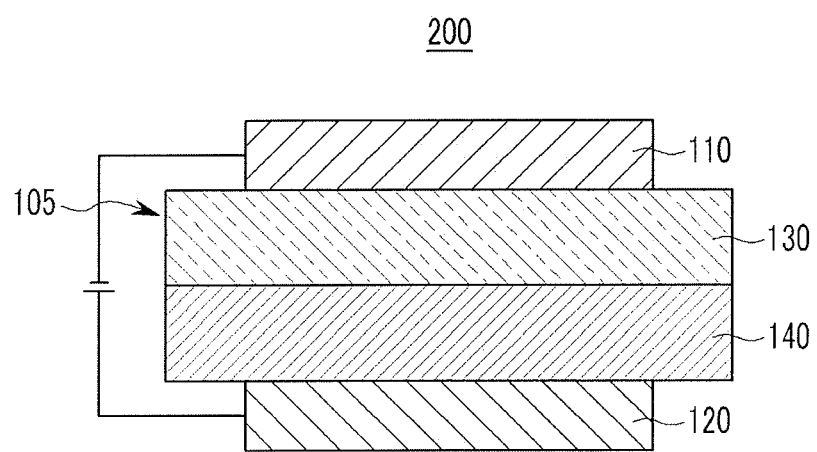

COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

CROSS-REFERENCE TO RELATED APPLICATION

This application claims priority to and the benefit of Korean Patent Application No. 10-2016-0163667 filed in the Korean Intellectual Property Office on Dec. 2, 2016, the entire contents of which are incorporated herein by reference.

BACKGROUND

1. Field

A compound for an organic optoelectronic device, a composition for an organic optoelectronic device, an organic optoelectronic device, and a display device are disclosed.

2. Description of the Related Art

An organic optoelectronic device is a device that converts electrical energy into photo energy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device are an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an Herein, the organic layer may include a light emitting layer and optionally an auxiliary layer, and the auxiliary layer may be, for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY

An embodiment provides a compound for an organic optoelectronic device capable of realizing an organic optoelectronic device having high efficiency and long life-span.

Another embodiment provides a composition for an organic optoelectronic device including the compound for an organic optoelectronic device.

Yet another embodiment provides an organic optoelectronic device including the compound.

Still another embodiment provides a display device including the organic optoelectronic device.

According to an embodiment, a compound for an organic optoelectronic device represented by Chemical Formula 1 is provided.

[Chemical Formula 1]

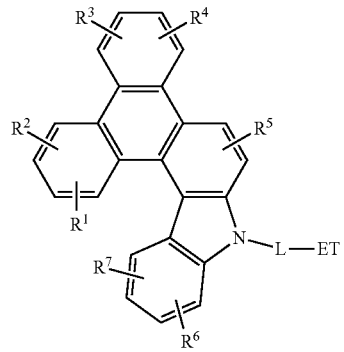

In Chemical Formula 1, $R^1$ to $R^7$ are independently hydrogen, deuterium, a substituted or unsubstituted C1 to C5 alkyl group, or a substituted or unsubstituted C6 to C18 aryl group, L is a single bond, a substituted or unsubstituted C6 to C20 arylene group, or a substituted or unsubstituted C2 to C30 heteroarylene group, ET is a substituted or unsubstituted C2 to C30 heterocyclic group including at least two N's, and the "substituted" refers to replacement of at least one hydrogen by deuterium, a cyano group, a C1 to C20 alkyl group, a C6 to C30 aryl group, or a C2 to C30 heteroaryl group.

According to another embodiment, a composition for an organic optoelectronic device includes a first compound for an organic optoelectronic device that is the compound; and a second compound for an organic optoelectronic device represented by Chemical Formula 2.

[Chemical Formula 2]

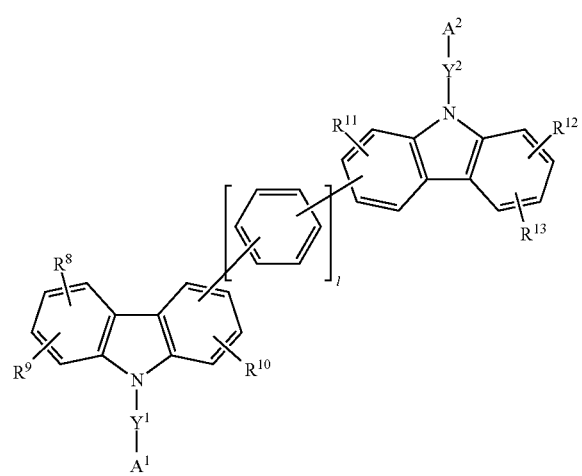

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $A^1$ and $A^2$ are independently substituted or unsubstituted C6 to C30 aryl group, a substituted or unsubstituted C2 to C30 heterocyclic group, or a combination thereof, $R^8$ to $R^{13}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and l is an integer of 0 to 2;

wherein the "substituted" refers to replacement of at least one hydrogen by deuterium, a C1 to C4 alkyl group, a C6 to C18 aryl group, or a C2 to C30 heteroaryl group.

According to another embodiment, an organic optoelectronic device includes an anode and a cathode facing each other and at least one organic layer disposed between the anode and the cathode, wherein the organic layer includes the compound for an organic optoelectronic device or the composition for an organic optoelectronic device.

According to yet another embodiment, a display device includes the organic optoelectronic device.

An organic optoelectronic device having high efficiency and a long life-span may be realized.

BRIEF DESCRIPTION OF THE DRAWINGS

FIGS. 1 and 2 are cross-sectional views showing organic light emitting diodes according to embodiments.

DETAILED DESCRIPTION

Hereinafter, embodiments of the present disclosure are described in detail. However, these embodiments are exemplary, the present disclosure is not limited thereto and the present disclosure is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present disclosure, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In a specific example of the present disclosure, "substituted" refers to replacement of at least one hydrogen of a substituent or a compound by deuterium, a C1 to C20 alkyl group, a C6 to C30 aryl group, or a C2 to C30 heteroaryl group. In a specific example of the present disclosure, "substituted" refers to replacement of at least one hydrogen of a substituent or a compound by deuterium, a C1 to C5 alkyl group, a C6 to C18 aryl group, a pyridinyl group, a quinolinyl group, an isoquinolinyl group, a quinazolinyl group, a dibenzofuranyl group, a dibenzothiophenyl group, or a carbazolyl group. In a specific example of the present disclosure, "substituted" refers to replacement of at least one hydrogen of a substituent or a compound by deuterium, a C1 to C5 alkyl group, a C6 to C18 aryl group, a pyridinyl group, a quinazolinyl group, a dibenzofuranyl group, or a dibenzothiophenyl group. In a specific example of the present disclosure, "substituted" refers to replacement of at least one hydrogen of a substituent or a compound by deuterium, a methyl group, an ethyl group, a propanyl group, a butyl group, a phenyl group, a biphenyl group, a terphenyl group, a naphthyl group, a triphenyl group, a fluorenyl group, a pyridinyl group, a quinazolinyl group, a carbazolyl group, a dibenzofuranyl group, or a dibenzothiophenyl group.

As used herein, when a definition is not otherwise provided, "hetero" refers to one including one to three heteroatoms selected from N, O, S, P, and Si, and remaining carbons in one functional group.

As used herein, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quaterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms. For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, a quinazolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted benzoquinolinyl group, a substituted or unsubstituted benzoisoquinolinyl group, a substituted or unsubstituted benzoquinazolinyl group, a substituted or unsubstituted benzothieno[3,2-d]pyrimidinyl group, a substituted or unsubstituted benzothieno[2,3-d]pyrimidinyl group, a substituted or unsubstituted benzofuro[3,2-d]pyrimidinyl group, a substituted or unsubstituted benzofuro[2,3-d]pyrimidinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment is represented by Chemical Formula 1.

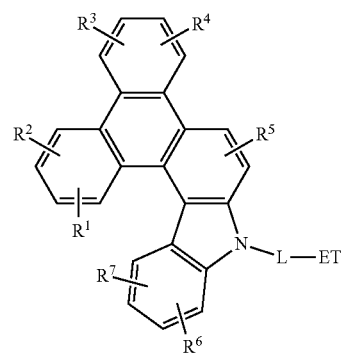

[Chemical Formula 1]

In Chemical Formula 1, $R^1$ to $R^7$ are independently hydrogen, deuterium, a substituted or unsubstituted C1 to C5 alkyl group, or a substituted or unsubstituted C6 to C18 aryl group, L is a single bond, a substituted or unsubstituted C6 to C20 arylene group, or a substituted or unsubstituted C2 to C30 heteroarylene group, ET is a substituted or unsubstituted C2 to C30 heterocyclic group including at least two N's, and the "substituted" refers to replacement of at least one hydrogen by deuterium, a cyano group, a C1 to C20 alkyl group, a C6 to C30 aryl group, or a C2 to C30 heteroaryl group. In a specific example of the present disclosure, the "substituted" refers to replacement of at least one hydrogen by deuterium, a C1 to C4 alkyl group, a C6 to C30 aryl group, a pyridinyl group, a quinolinyl group, an isoquinolinyl group, or a quinazolinyl group. In a more specific example of the present disclosure, the "substituted" refers to replacement of at least one hydrogen by deuterium, a C1 to C4 alkyl group or a C6 to C18 aryl group. For example, the "substituted" refers to replacement of at least one hydrogen by deuterium, a phenyl group, a biphenyl group, a terphenyl group, or a naphthyl group.

The compound for an organic optoelectronic device according to the present disclosure has a structure that an ET unit, that is, a moiety linked with a substituent having high electron mobility substituted for an amine group of carbazole, and a phenanthrene moiety is fused with the carbazole and thus may realize a device having a long life-span, a low driving voltage, and high efficiency.

In particular, since the position Nos. 3 and 4 of the carbazole are fused with the position Nos. 5 and 6 of the phenanthrene, the compound may have a shallow HOMO energy level, thus holes may be easily injected thereinto, and resultantly, a device having a low driving voltage and high efficiency may be realized. In addition, when the position Nos. 3 and 4 of the carbazole are fused with the position Nos. 5 and 6 of the phenanthrene rather than the other positions of the phenanthrene, the above effect may be maximized.

The compound according to the present disclosure includes phenanthrene that is fused with carbazole substituted with the ET unit, and thereby stability of the compound during a process may be increased and its degradation may be suppressed when it is applied to a device due to a high glass transition temperature (Tg). The glass transition temperature (Tg) may be related with thermal stability of a compound and a device including the compound. That is, when a compound for an organic optoelectronic device having a high glass transition temperature (Tg) is applied to an organic light emitting diode in a form of a thin film, degradation by the temperature may be suppressed in a subsequent process, for example an encapsulation process after depositing the compound for an organic optoelectronic device, life-span characteristics of the compound and a device may be ensured.

In addition, since the compound may interact with an electrode due to a polar group of nitrogen included in the ET unit, charges may be easily injected thereinto and have high mobility, and thus a low driving voltage may be realized.

In addition, since the compound is suppressed from crystallization as the interaction among molecules is reduced due to steric hindrance of the molecule structure, a yield of an organic light emitting diode including the same may be improved, and its long life-span may be secured.

In an example embodiment of the present disclosure, the substituted or unsubstituted C2 to C30 heterocyclic group including at least two N's is a substituent including an N-containing heterocyclic group, and herein, in the N-containing heterocyclic group, a ring having N may be directly linked with "N" of fused carbazole or a linking group "L", but when the N-containing heterocyclic group is a fused ring, a ring having N may not be directly linked with "N" of fused carbazole or a linking group "L."

Specifically, the ET may be a substituted or unsubstituted pyrimidinyl group, a substituted or unsubstituted triazinyl group, a substituted or unsubstituted quinazolinyl group, a substituted or unsubstituted benzoquinazolinyl group, a substituted or unsubstituted benzothieno[3,2-d]pyrimidinyl group, a substituted or unsubstituted benzothieno[2,3-d]pyrimidinyl group, a substituted or unsubstituted benzofuro[3,2-d]pyrimidinyl group, or a substituted or unsubstituted benzofuro[2,3-d]pyrimidinyl group, for example a substituted or unsubstituted pyrimidinyl group, a substituted or unsubstituted triazinyl group, a substituted or unsubstituted quinazolinyl group, a substituted or unsubstituted benzothieno[3,2-d]pyrimidinyl group, a substituted or unsubstituted benzothieno[2,3-d]pyrimidinyl group, a substituted or unsubstituted benzofuro[3,2-d]pyrimidinyl group, or a substituted or unsubstituted benzofuro[2,3-d]pyrimidinyl group.

In an example embodiment of the present disclosure, Chemical Formula 1 may be represented by one of Chemical Formula 1-I, Chemical Formula 1-II, Chemical Formula 1-III, Chemical Formula 1-IV, Chemical Formula 1-V, and Chemical Formula 1-VI.

[Chemical Formula 1-I]

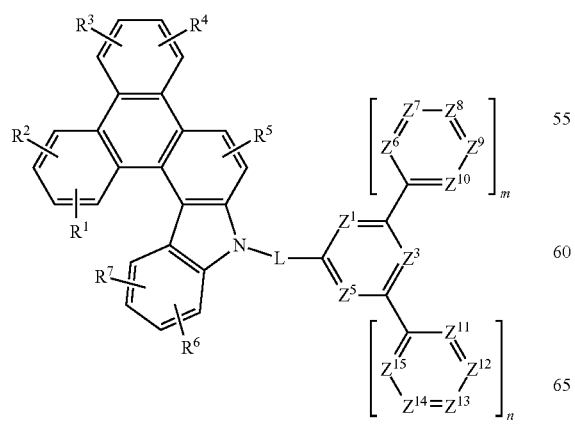

[Chemical Formula 1-II]

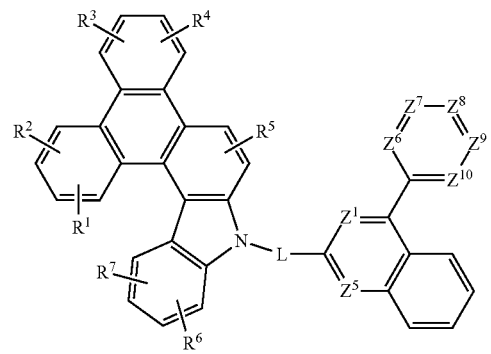

[Chemical Formula 1-III]

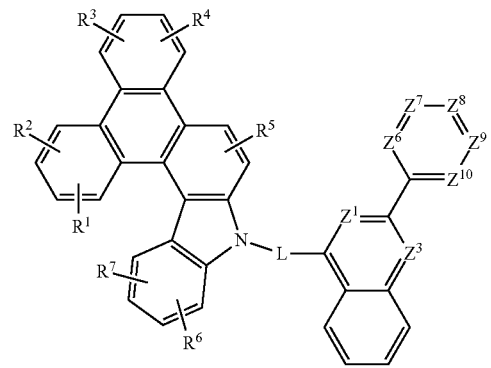

[Chemical Formula 1-IV]

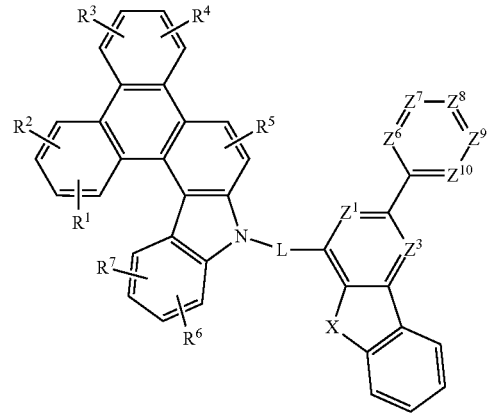

[Chemical Formula 1-V]

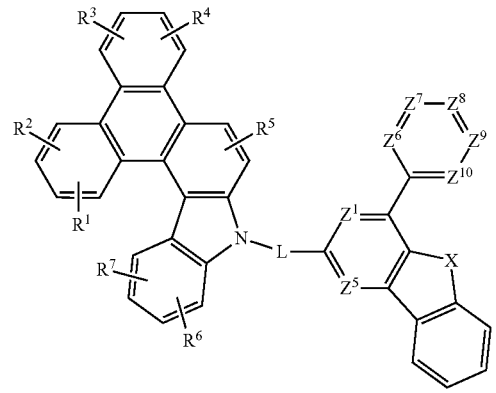

-continued

[Chemical Formula 1-VI]

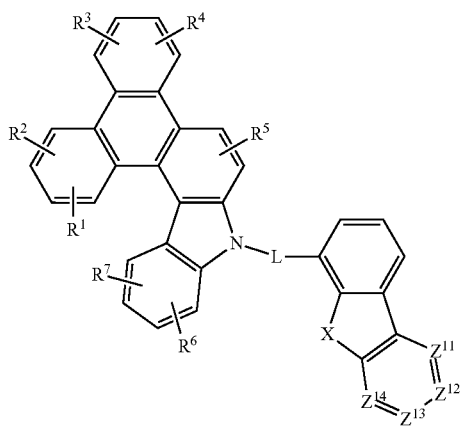

[Chemical Formula 1-II a]

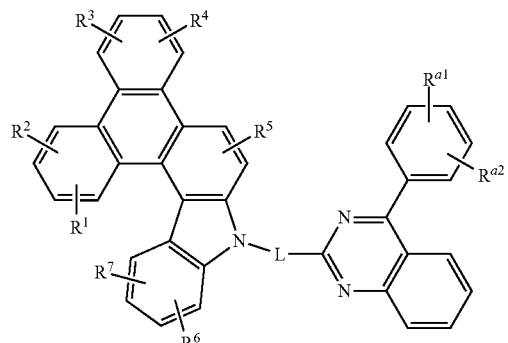

[Chemical Formula 1-III a]

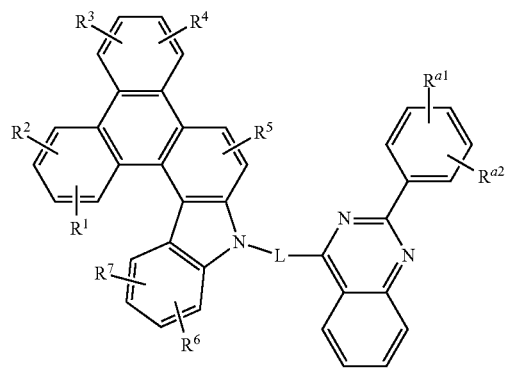

[Chemical Formula 1-IVa]

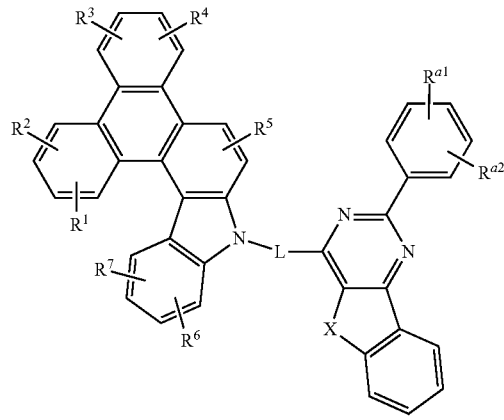

[Chemical Formula 1-Va]

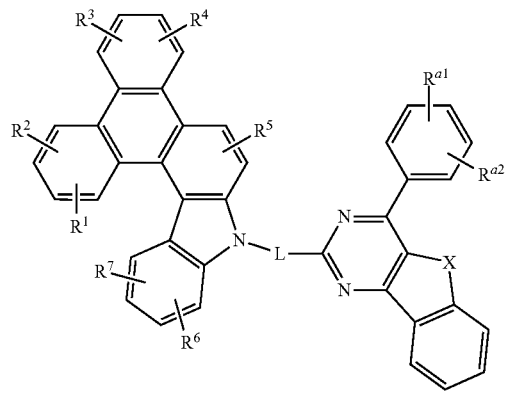

In Chemical Formula 1-I, Chemical Formula 1-II, Chemical Formula 1-III, Chemical Formula 1-IV, Chemical Formula 1-V, and Chemical Formula 1-VI, $R^1$ to $R^7$, and L are the same as above, $Z^1$, $Z^3$, $Z^5$, and $Z^6$ to $Z^{15}$ are independently N or $CR^a$, at least two of $Z^1$, $Z^3$, and $Z^5$ of Chemical Formula 1-I to Chemical Formula 1-V are N, at least two of $Z^{11}$ to $Z^{14}$ of Chemical Formula 1-VI are N, $R^a$ is the same as $R^1$ to $R^7$, m and n are independently an integer of 0 to 2, and X is O or S.

On the other hand, Chemical Formula 1 I may be for example represented by Chemical Formula 1-Ia.

[Chemical Formula 1-Ia]

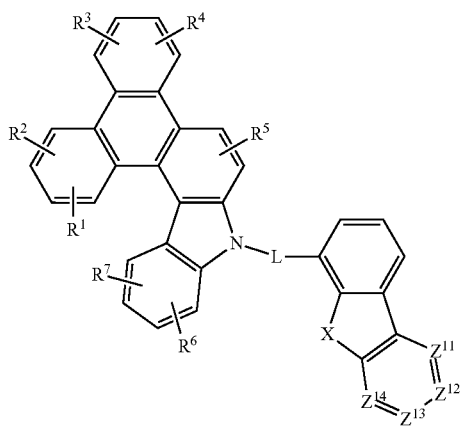

In Chemical Formula 14a, $R^1$ to $R^7$, and L are the same as above, $Z^1$, $Z^3$, and $Z^5$ are independently, N or $CR^a$, and at least two of $Z^1$, $Z^3$, and $Z^5$ are N, m and n are independently an integer of 0 to 2, and $R^a$, $R^{a1}$, $R^{a2}$, $R^{a3}$, and $R^{a4}$ are the same as $R^1$ to $R^7$.

In addition, Chemical Formula 1-II to Chemical Formula 1-VI may be for example represented by Chemical Formula 1-II a, Chemical Formula 1-III a, Chemical Formula 1-IVa, Chemical Formula 1-Va, and Chemical Formula 1-VIa.

[Chemical Formula 1-VIa]

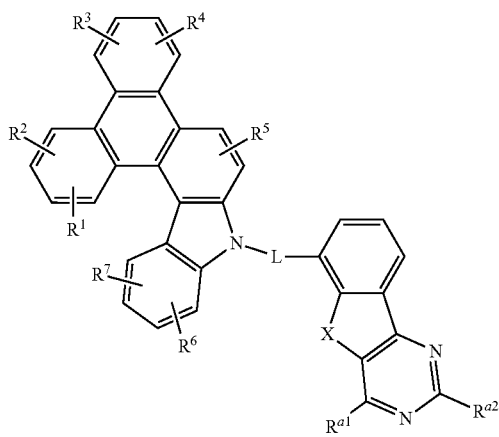

In Chemical Formula 1-II a. Chemical Formula 1-III a, Chemical Formula 1-IVa, Chemical Formula 1-Va, and Chemical Formula 1-VIa, $R^1$ to $R^7$, $R^{a1}$, $R^{a2}$, X and L are the same as described above.

In an example embodiment of the present disclosure, R' to $R^7$ and $R^{a1}$ to $R^{a4}$ may independently be hydrogen or a substituted or unsubstituted C6 to C18 aryl group, and specifically hydrogen, a substituted or unsubstituted phenyl group, a substituted or unsubstituted biphenyl group, or a substituted or unsubstituted naphthyl group, and may be for example all hydrogen or one of $R^1$ to $R^7$ and $R^{a1}$ to $R^{a4}$ may be a phenyl group, or a biphenyl group.

In an example embodiment of the present disclosure, L may be a single bond, or a substituted or unsubstituted C6 to C20 arylene group, and specifically a single bond, a substituted or unsubstituted phenylene group, a substituted or unsubstituted biphenylene group, a substituted or unsubstituted terphenylene group, or a substituted or unsubstituted naphthylene group, and may be for example a single bond, a substituted or unsubstituted phenylene group, or a substituted or unsubstituted biphenylene group.

In an example embodiment of the present disclosure, m and n may independently be an integer of 0 or 1. Specifically, at least one of m and n may be 1 and for example morn may be 0 or m and n may be 1.

In an example embodiment of the present disclosure, the ET may be for example selected from substituents of Group I.

[Group I]

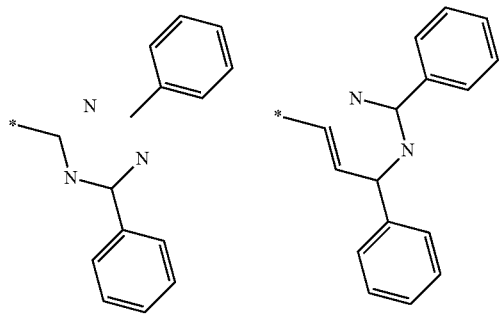

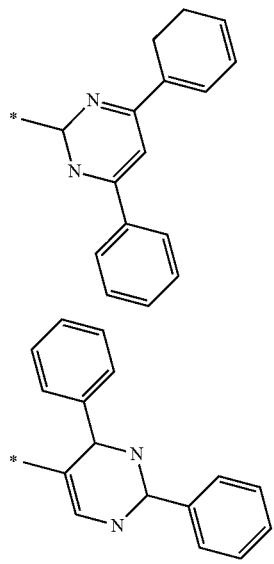

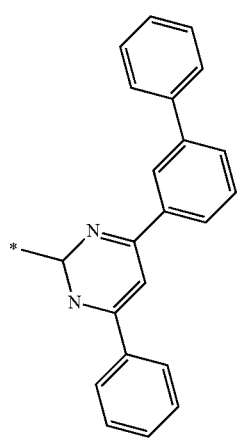

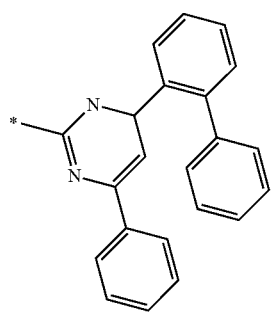

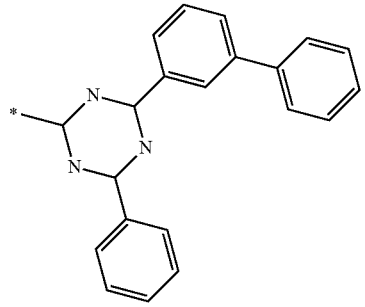

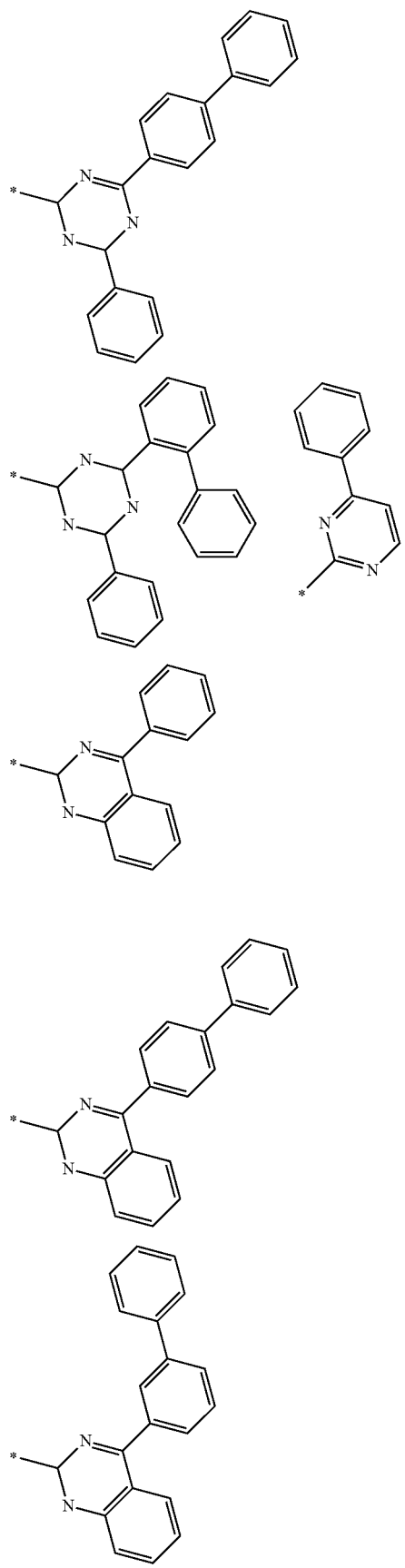
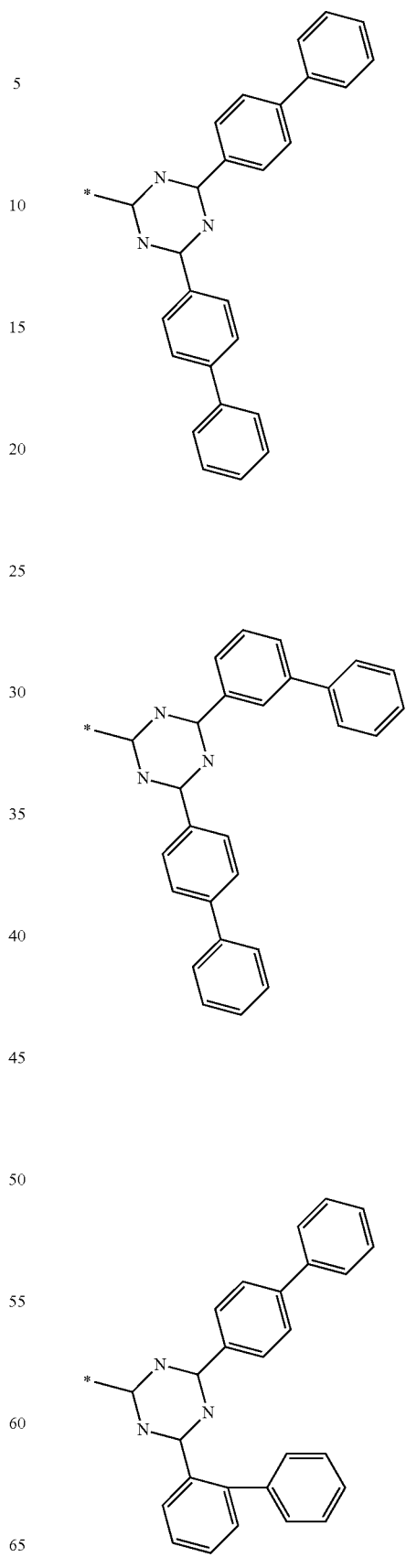

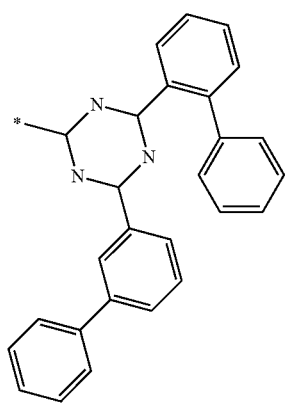
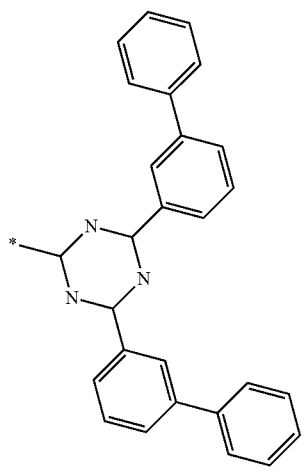
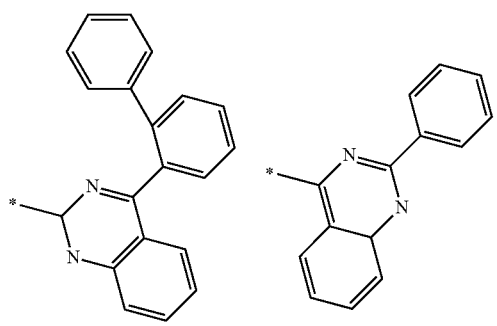
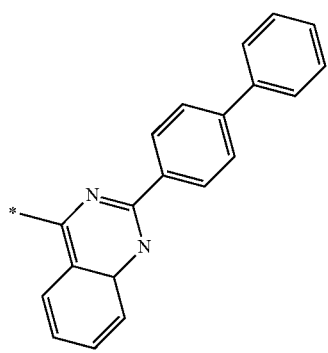
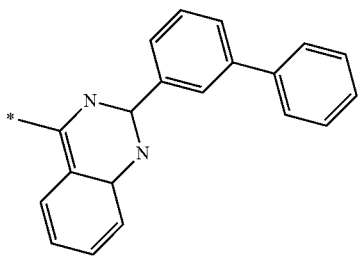
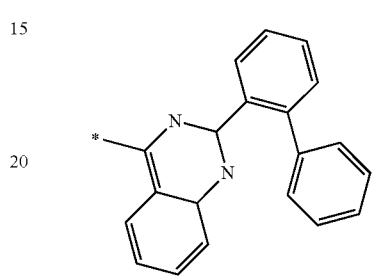
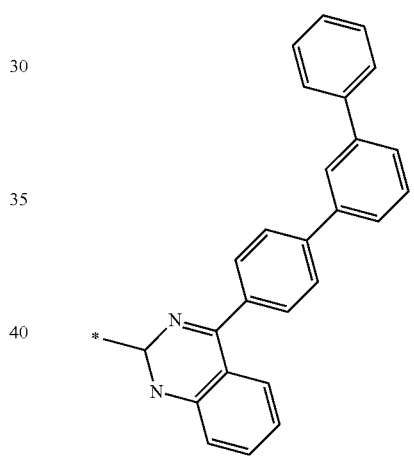
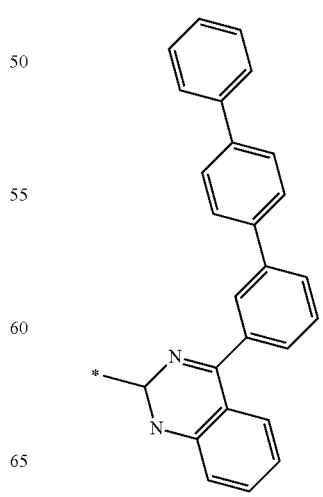

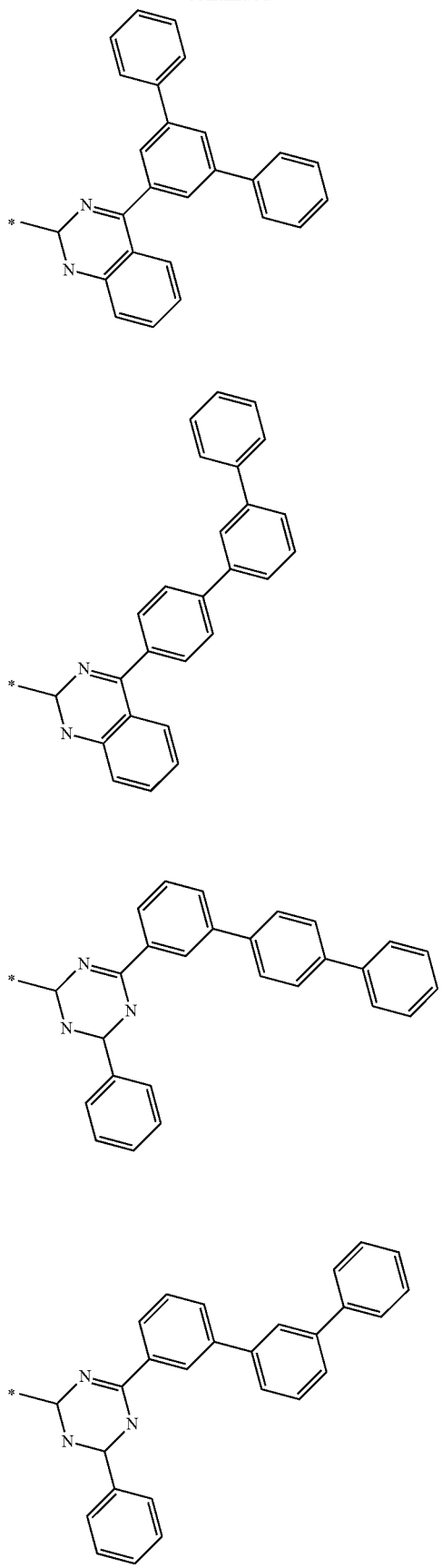

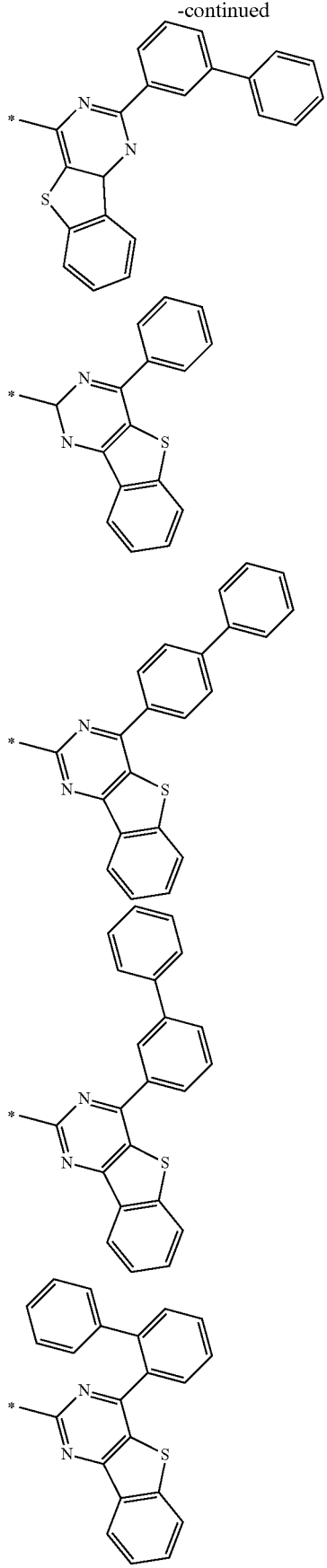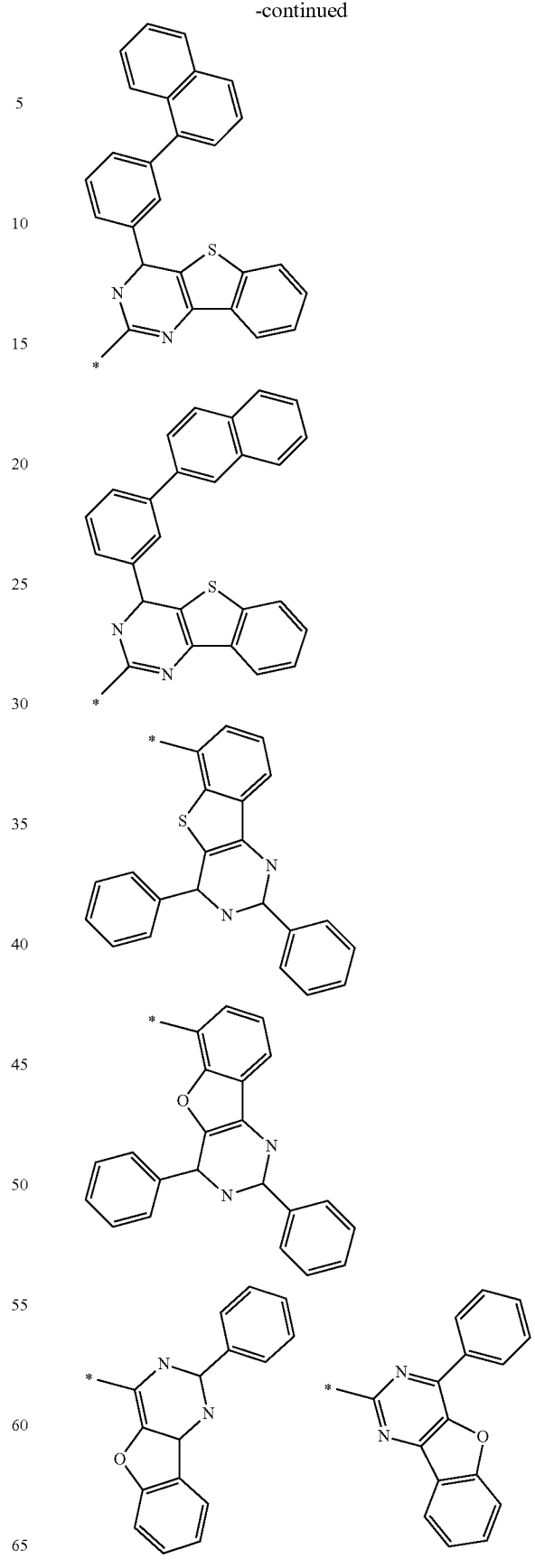

In Group I, * is a linking point of "L" of Chemical Formula 1.
The compound for an organic optoelectronic device represented by Chemical Formula 1 may be for example selected from compounds of Group 1, but is not limited thereto.
[Group 1]
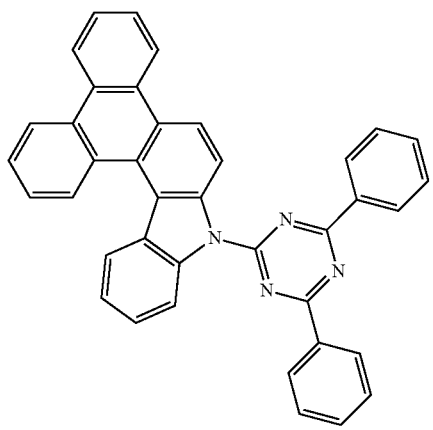
1
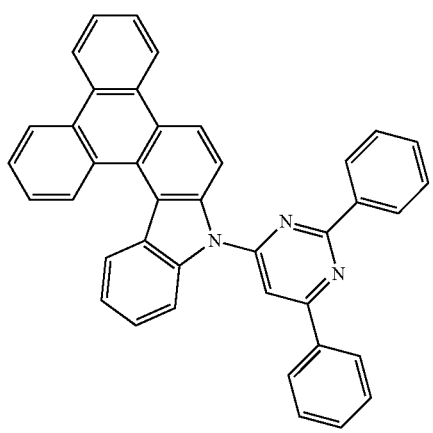
2
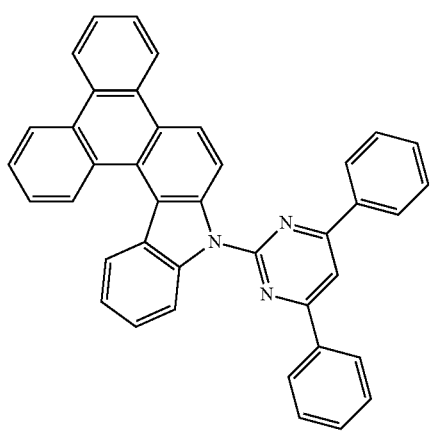
3
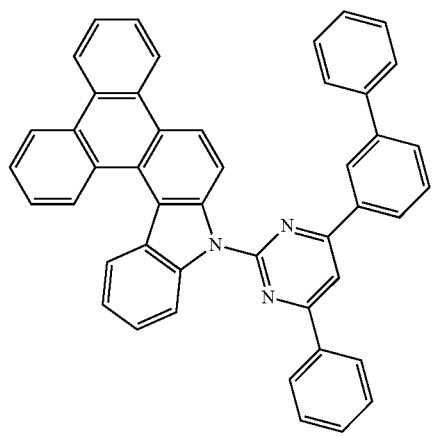
4
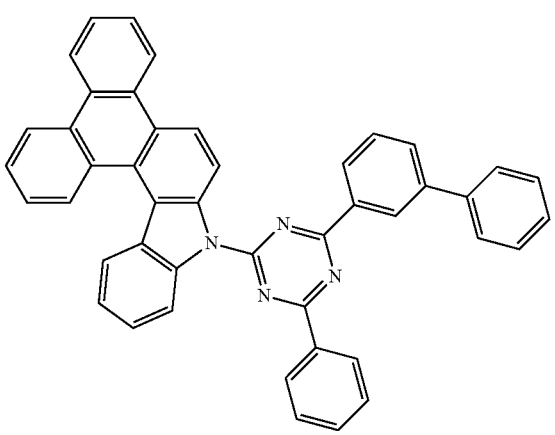
5
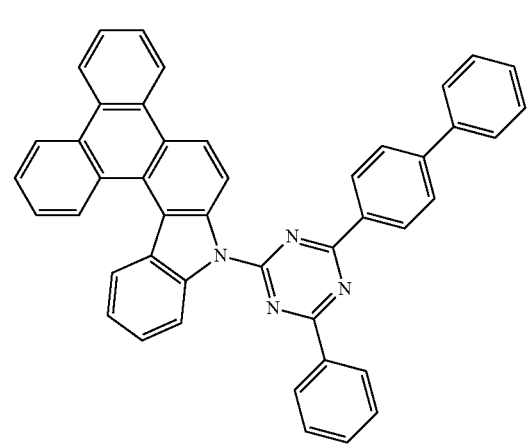
6

7
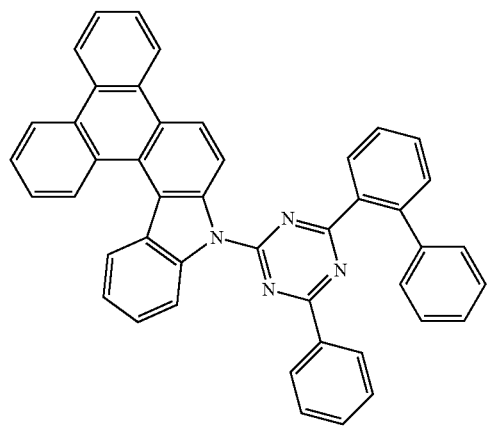
8
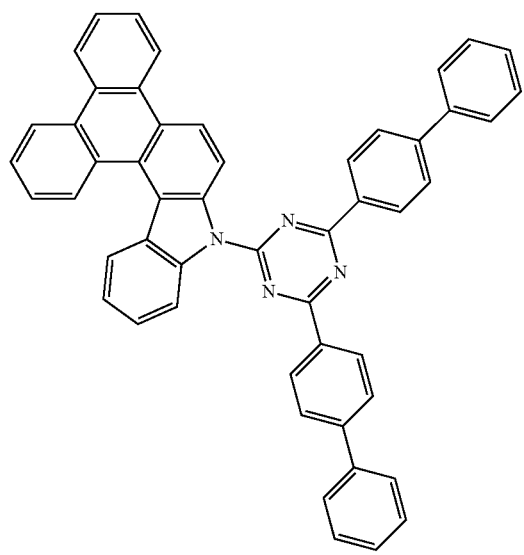
9
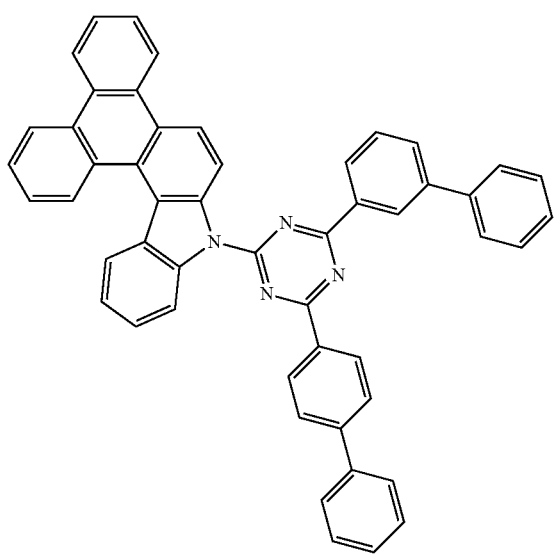
10
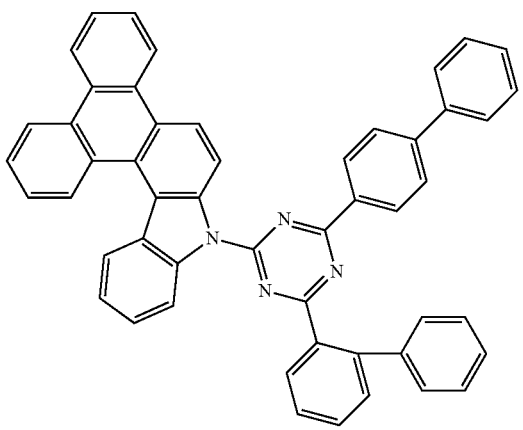
11
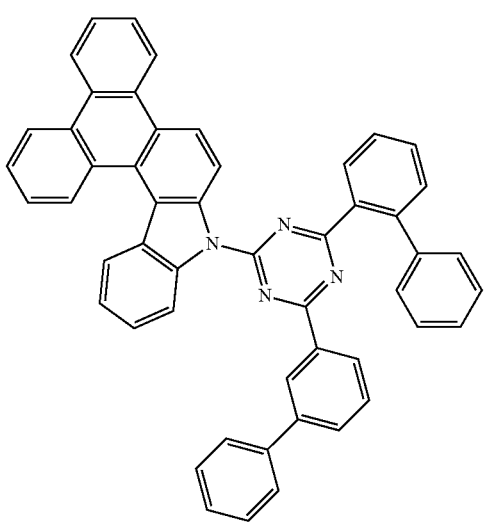
12
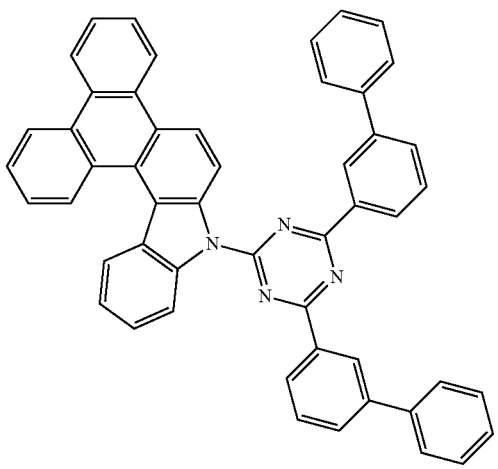

-continued
13
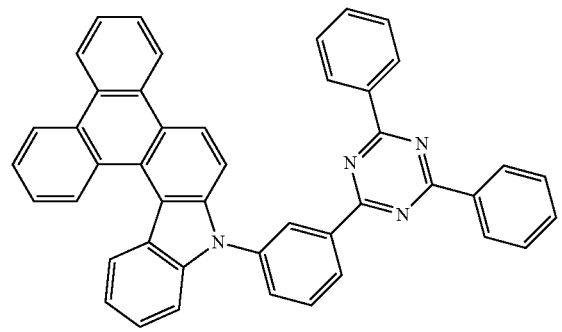
14
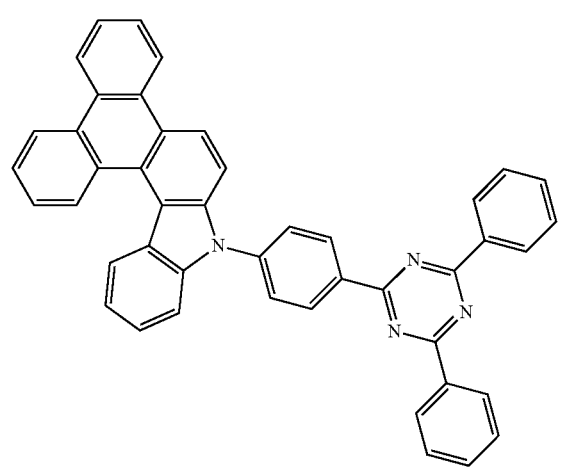
15
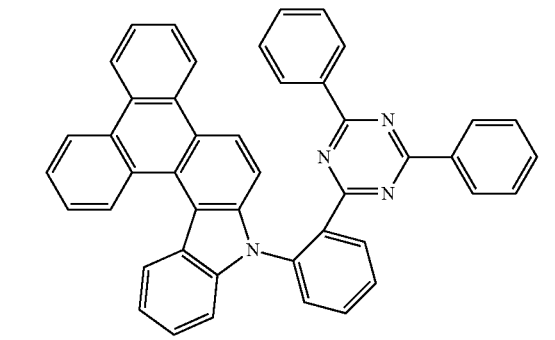
16
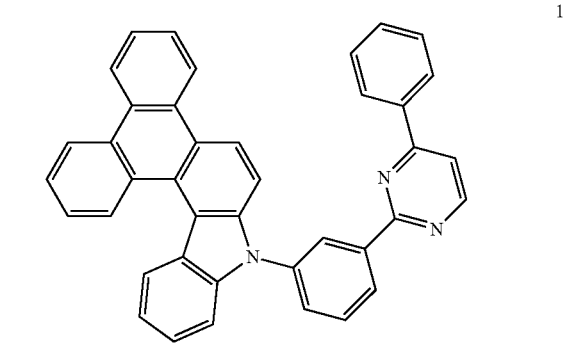
-continued
17
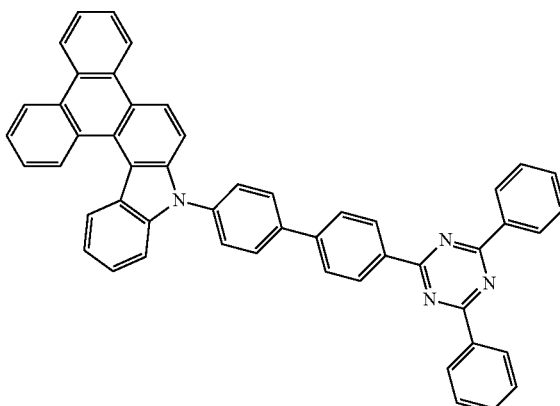
18
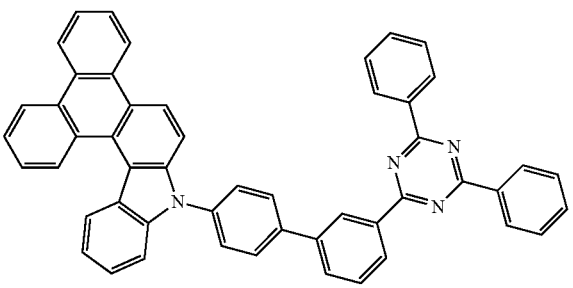
19

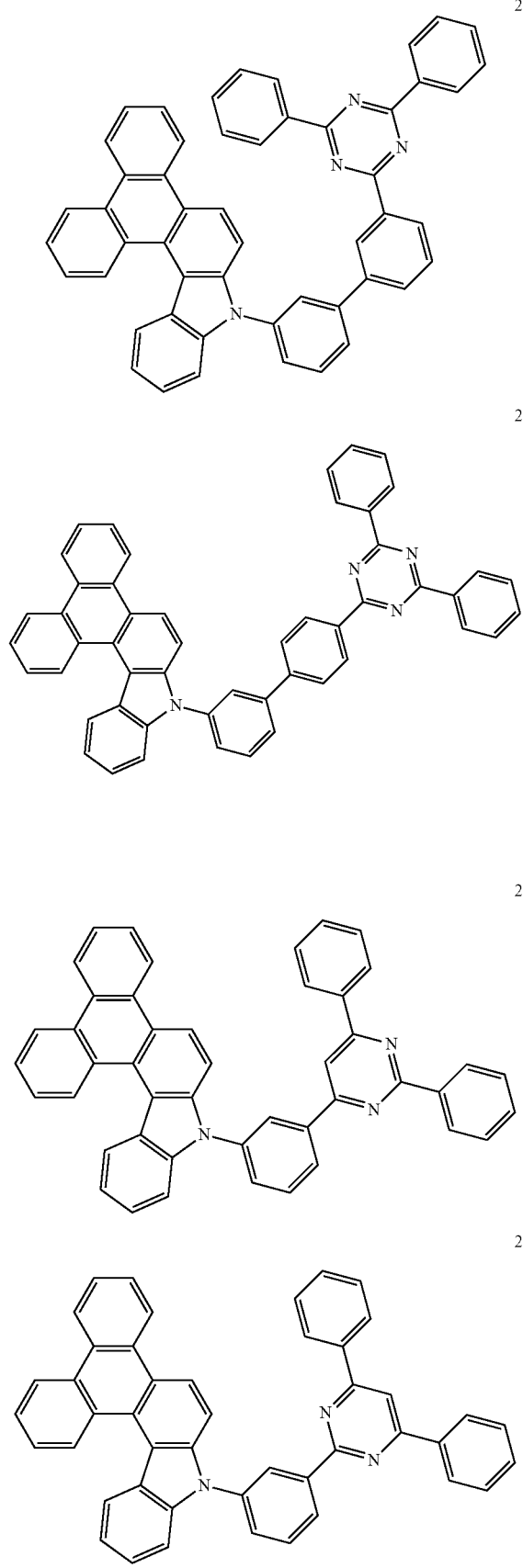
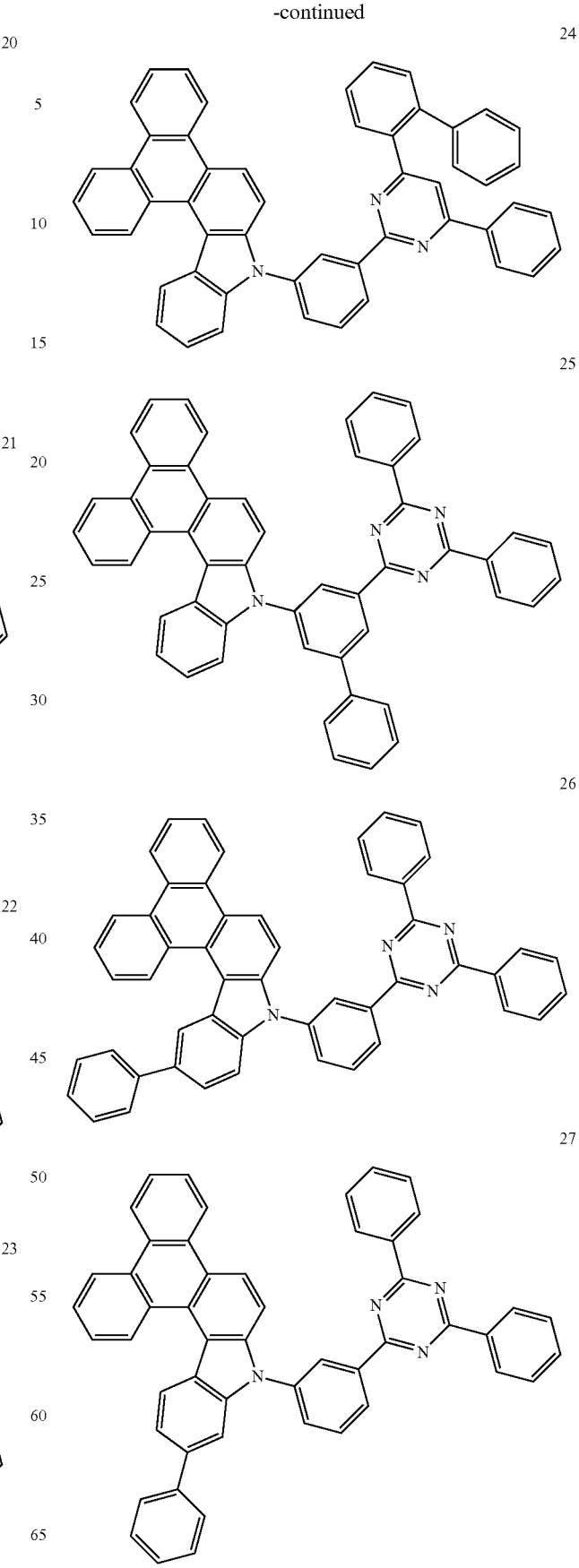

28
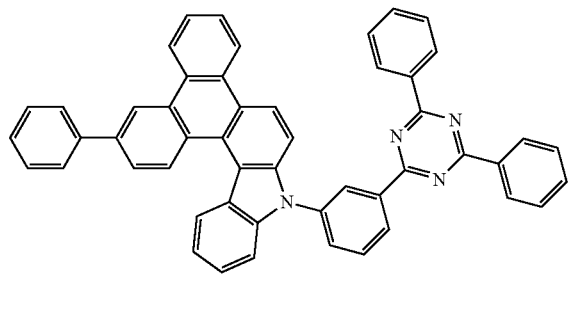
29
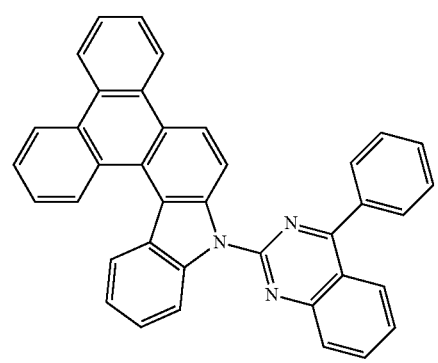
30
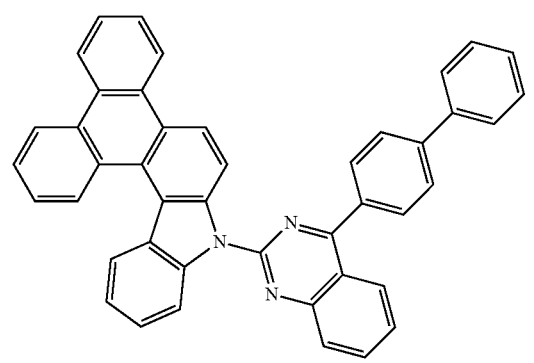
31
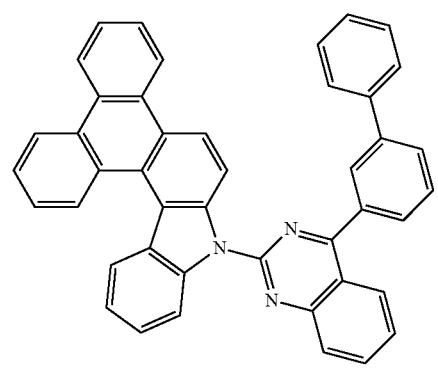
32
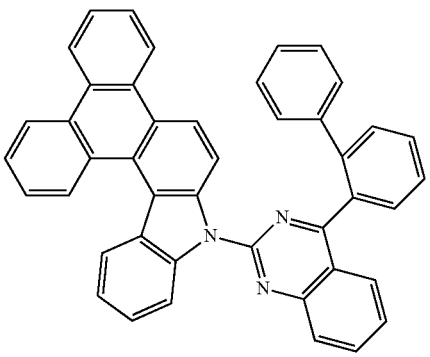
33
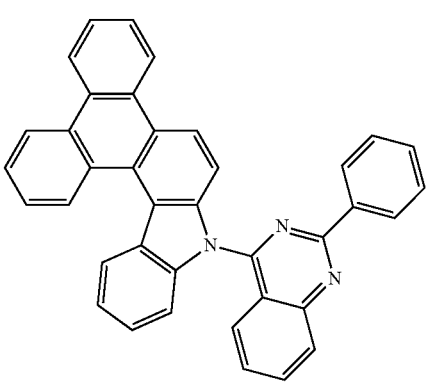
34
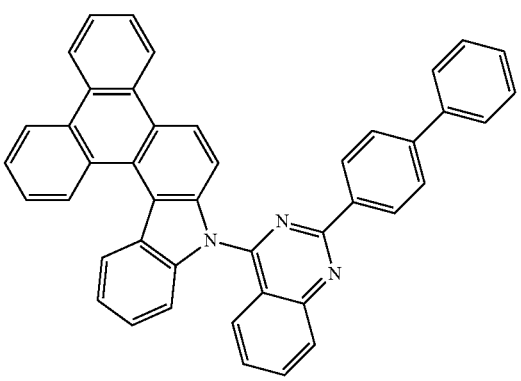
35
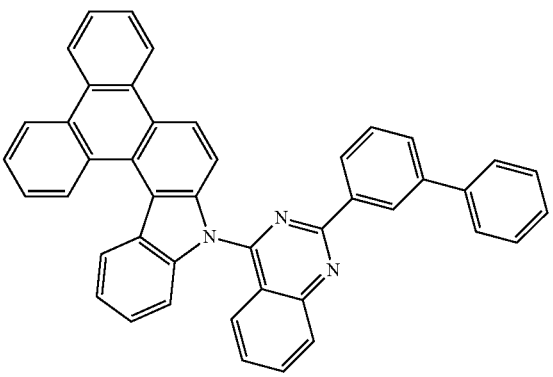

36
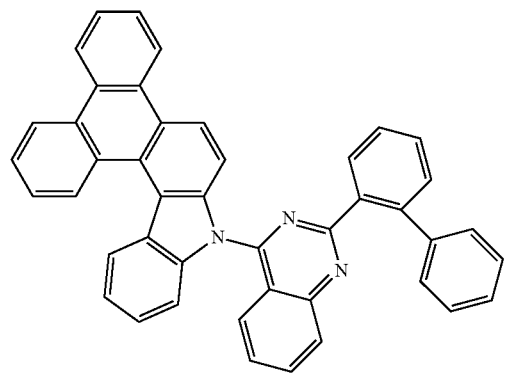
37
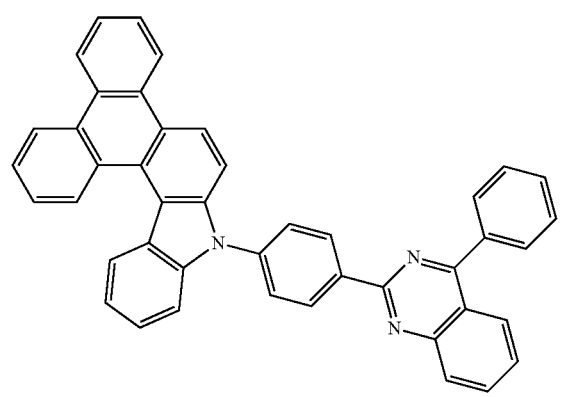
38
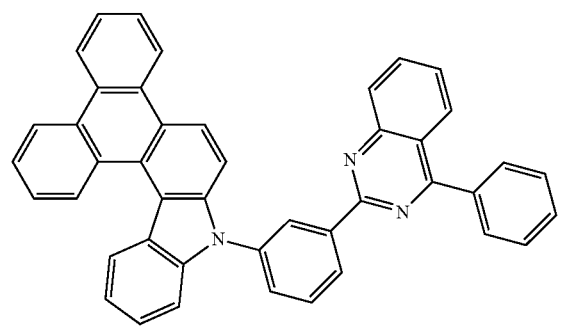
39
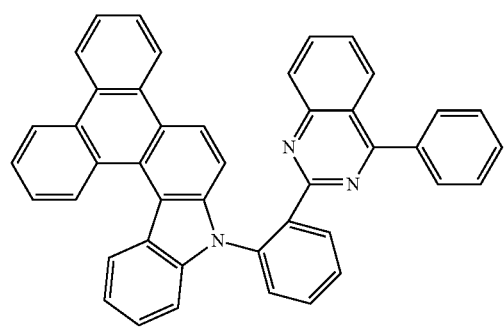
40
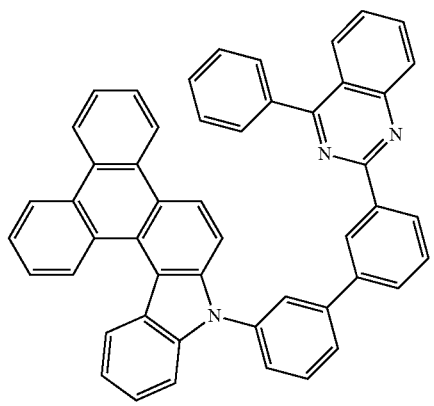
41
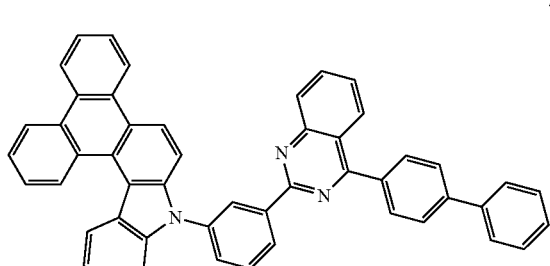
42
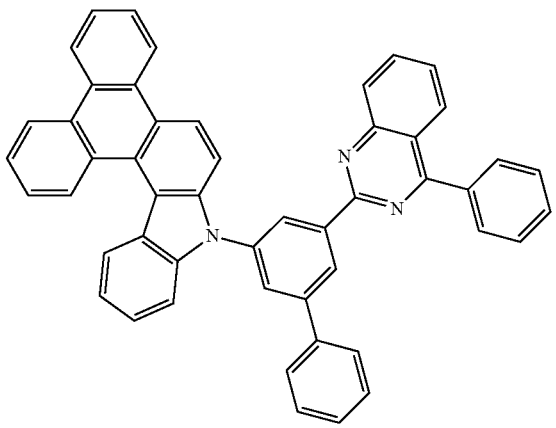
43
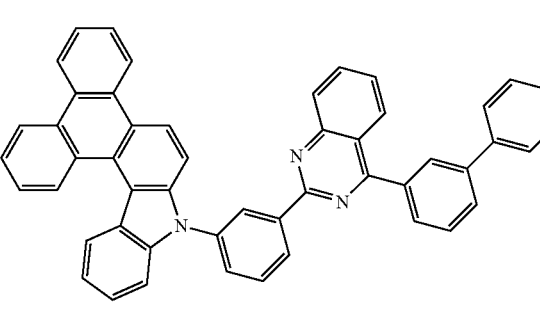

44
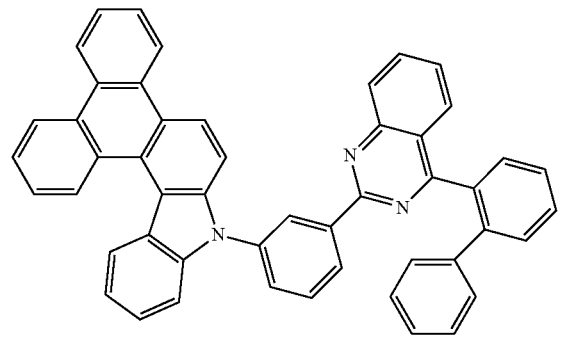
45
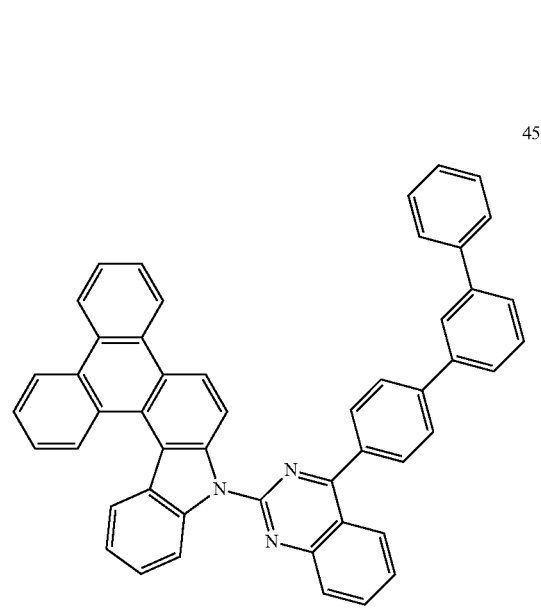
46
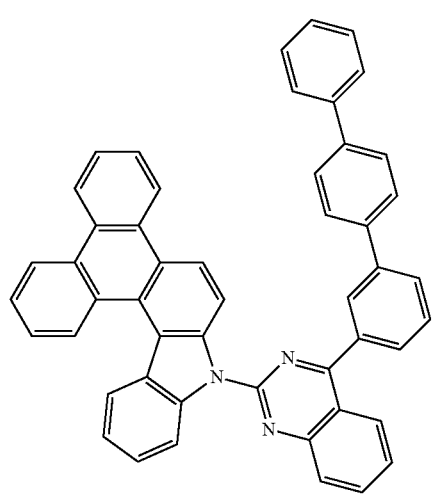
47
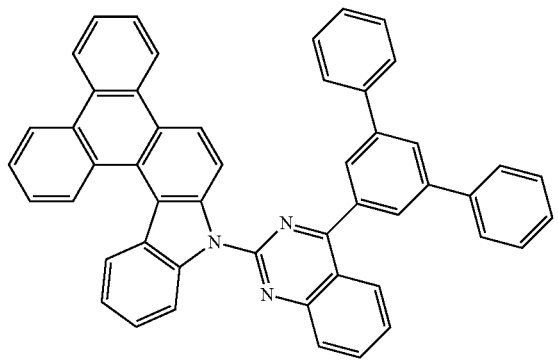
48
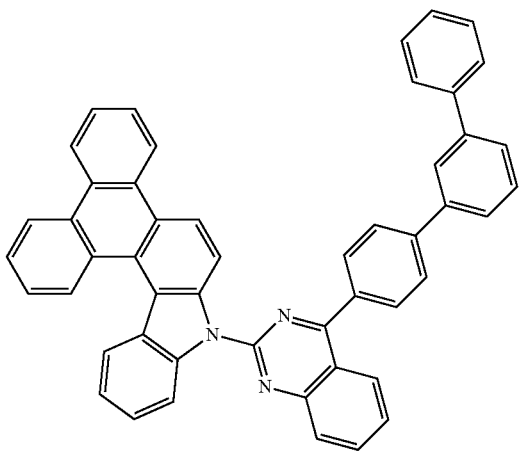
49
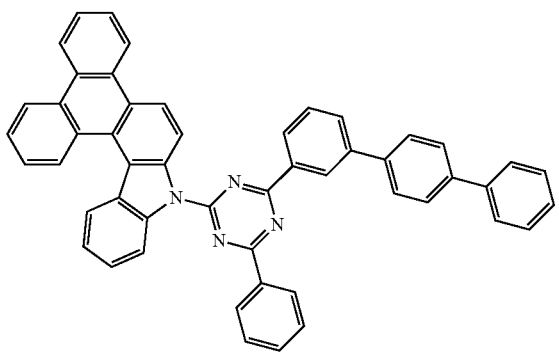
50
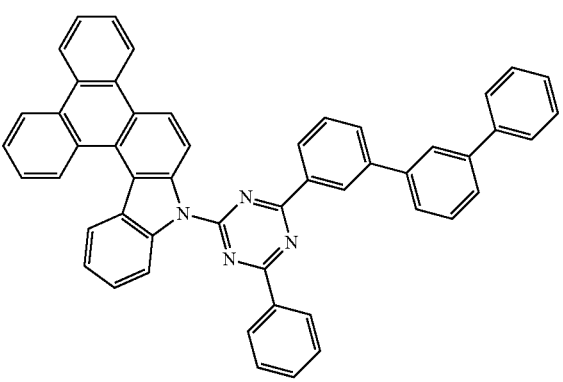

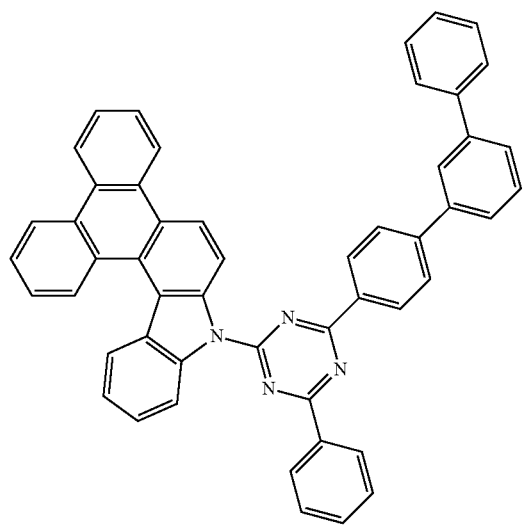
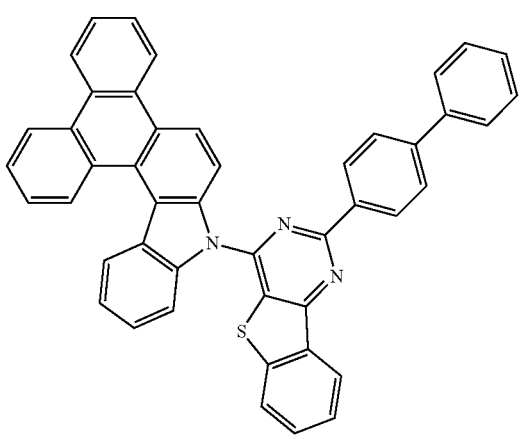
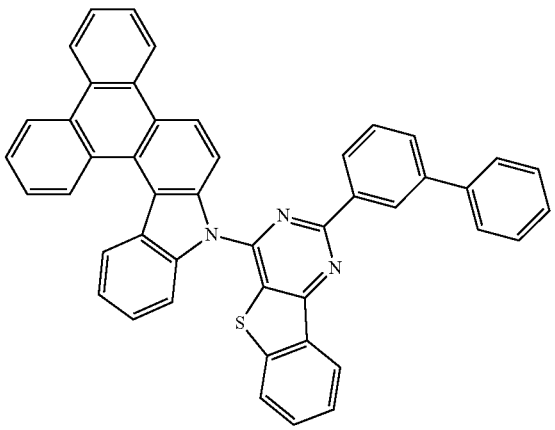
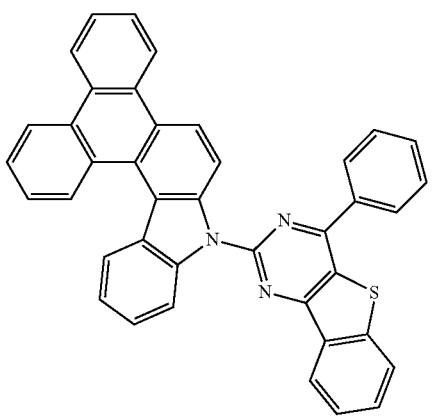

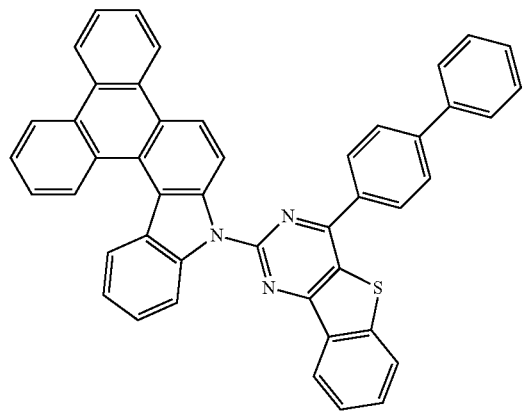
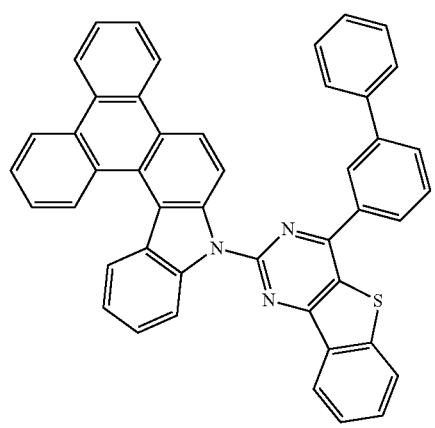
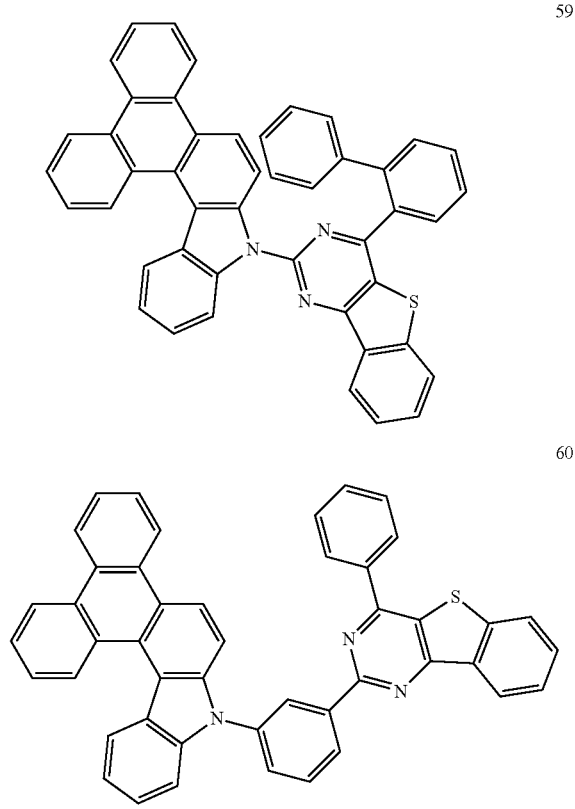
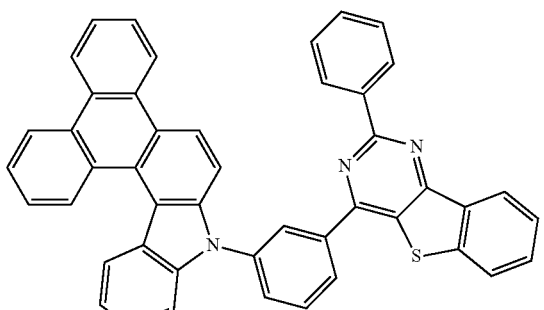
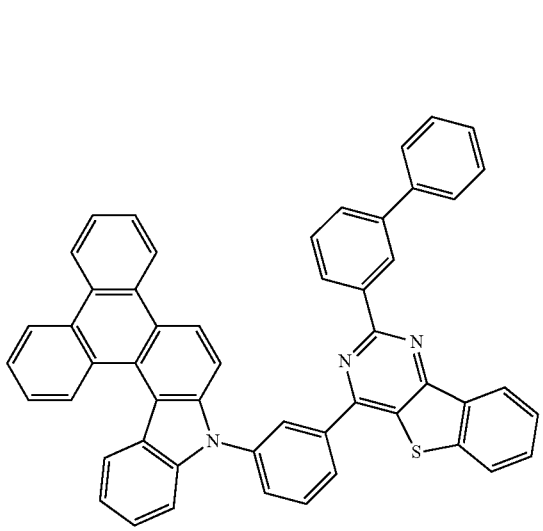

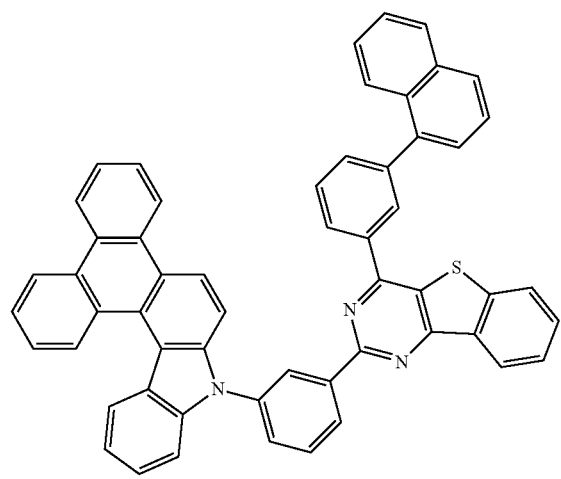
64
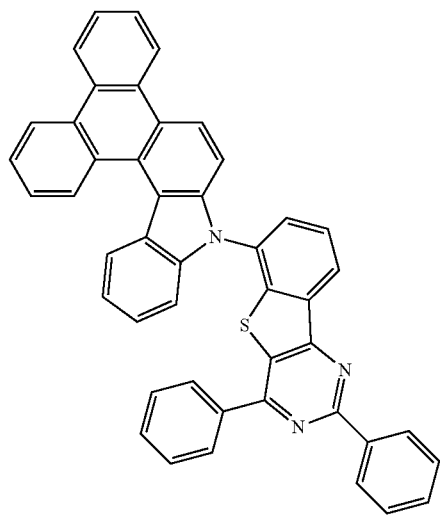
67
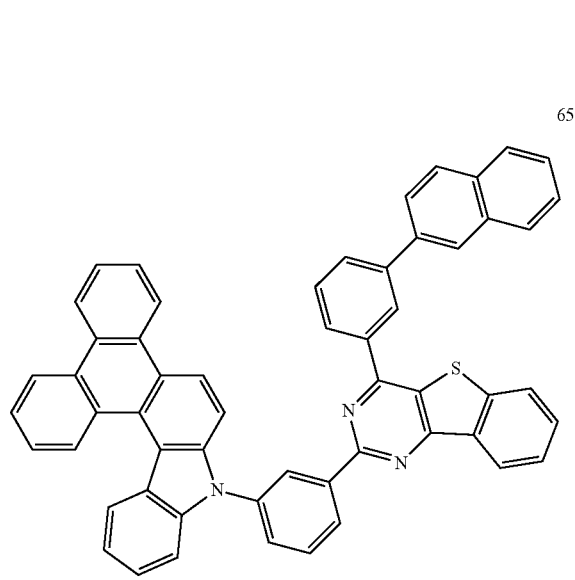
65
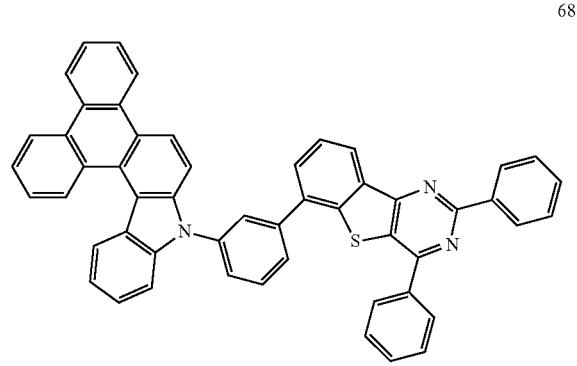
68
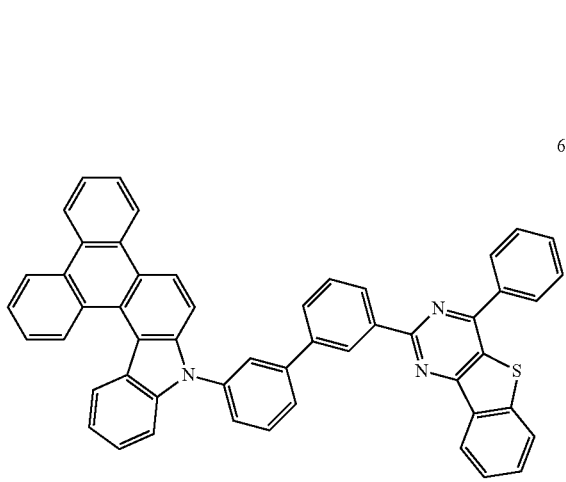
66
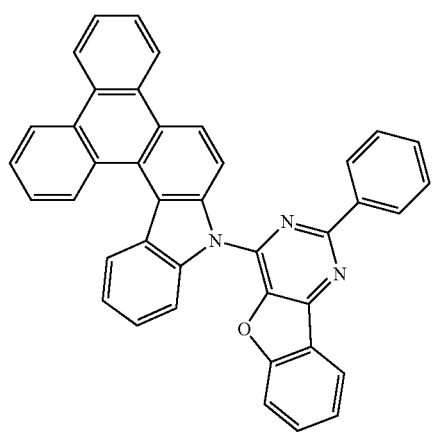
69

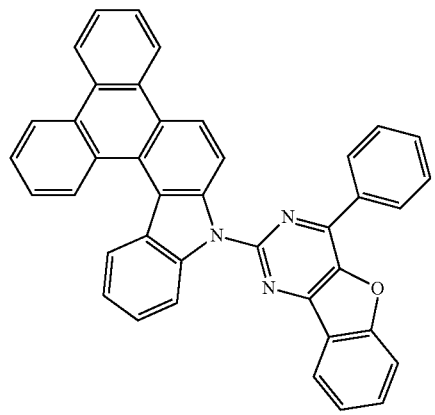

70

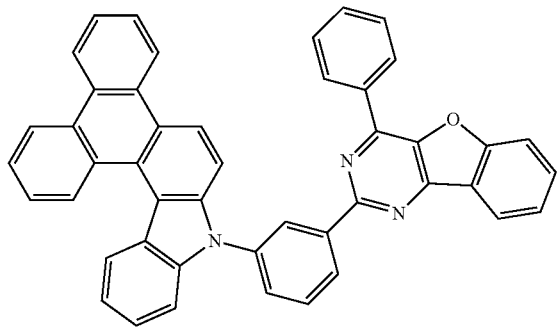

71

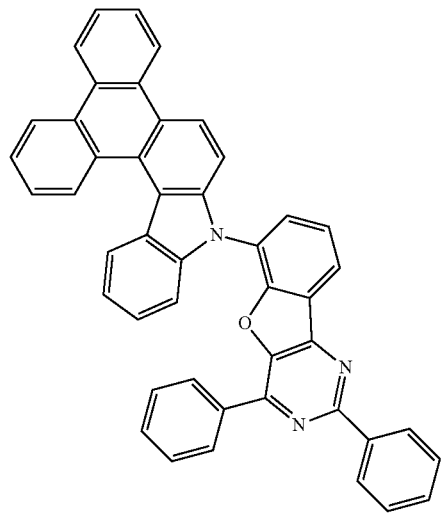

72

The compound for an organic optoelectronic device may be applied to an organic optoelectronic device and may be applied in an organic optoelectronic device alone or with other compounds for an organic optoelectronic device. When the compound for an organic optoelectronic device applied with other compounds for an organic optoelectronic device, it may be applied in a form of a composition.

Hereinafter, one example of a composition for an organic optoelectronic device including the first compound for an organic optoelectronic device is described.

The composition for an organic optoelectronic device according to another embodiment of the present disclosure includes the first compound for an organic optoelectronic device and a second compound for an organic optoelectronic device represented by Chemical Formula 2.

[Chemical Formula 2]

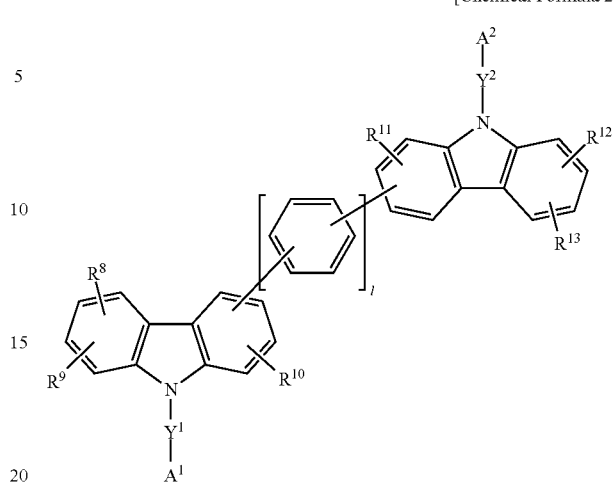

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $A^1$ and $A^2$ are independently substituted or unsubstituted C6 to C30 aryl group, a substituted or unsubstituted C2 to C30 heterocyclic group, or a combination thereof, $R^8$ to $R^{13}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and l is an integer of 0 to 2;

the "substituted" refers to replacement of at least one hydrogen by deuterium, a C1 to C4 alkyl group, a C6 to C18 aryl group, or a C2 to C30 heteroaryl group. In a specific example embodiment of the present disclosure, the "substituted" refers to replacement of at least one hydrogen by deuterium, a phenyl group, an ortho-biphenyl group, a meta-biphenyl group, a para-biphenyl group, a terphenyl group, a naphthyl group, a fluorenyl group, a triphenylene group, a pyridinyl group, a carbazolyl group, a dibenzofuranyl group, or a dibenzothiophenyl group.

In an example embodiment of the present disclosure, $Y^1$ and $Y^2$ of Chemical Formula 2 may independently be a single bond, or a substituted or unsubstituted C6 to C18 arylene group. Specifically, $Y^1$ and $Y^2$ may be a single bond, a meta-phenylene group, or a para-phenylene group.

In an example embodiment of the present disclosure, $A^1$ and $A^2$ of Chemical Formula 2 may independently be a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted triphenylene group, a substituted or unsubstituted pyridinyl group, a substituted or unsubstituted dibenzofuranyl group, a substituted or unsubstituted dibenzothiophenyl group, a substituted or unsubstituted carbazolyl group, a substituted or unsubstituted fluorenyl group, or a combination thereof. Specifically, $A^1$ and $A^2$ may be a substituted or unsubstituted phenyl group, a substituted or unsubstituted biphenyl group, a substituted or unsubstituted terphenyl group, a substituted or unsubstituted naphthyl group, a substituted or unsubstituted triphenylene group, a substituted or unsubstituted fluorenyl group, a substituted or unsubstituted carbazolyl group, a substituted or unsubstituted dibenzothiophenyl group, or a substituted or unsubstituted dibenzofuranyl group.

In an example embodiment of the present disclosure, $R^8$ to $R^{13}$ of Chemical Formula 2 may independently be hydrogen, deuterium, or a substituted or unsubstituted C6 to C12 aryl group. Specifically, $R^8$ to $R^{13}$ may be hydrogen or a phenyl group and for example, one of $R^8$ to $R^{13}$ may be a phenyl group and the rest may be hydrogen.

In an example embodiment of the present disclosure, 1 of Chemical Formula 2 may be 0 or 1.

In a specific example embodiment of the present disclosure, Chemical Formula 2 may have one of structures of Group II and *—$Y^1$-$A^1$ and *—$Y^2$-$A^2$ may be one of substituents of Group III.

[Group II]

C-1
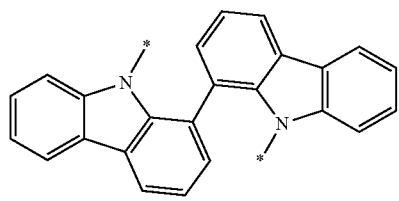

C-2
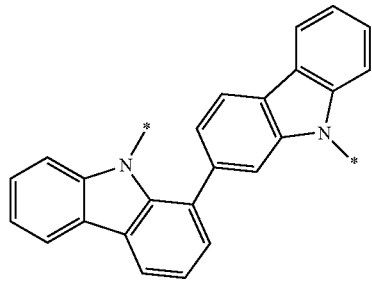

C-3
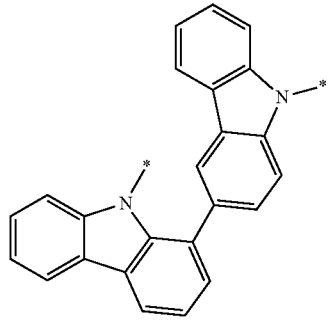

C-4
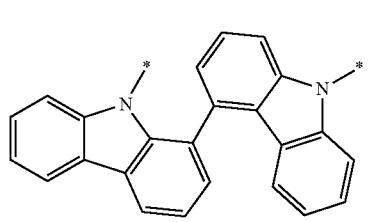

-continued

C-5
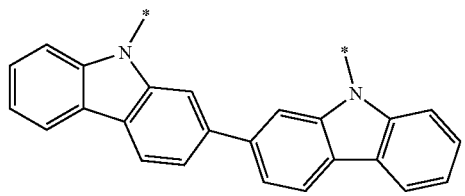

C-6
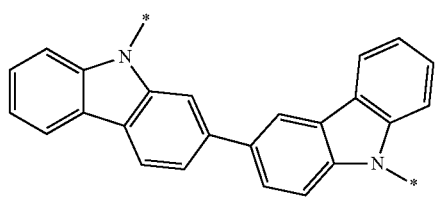

C-7
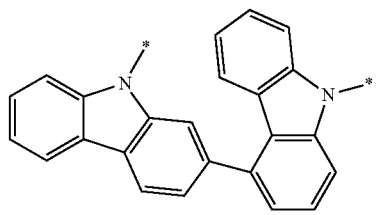

C-8
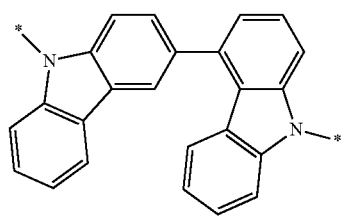

C-9
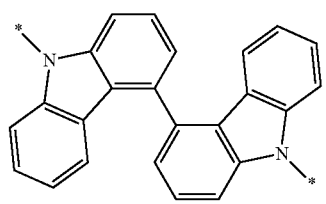

C-10

C-11
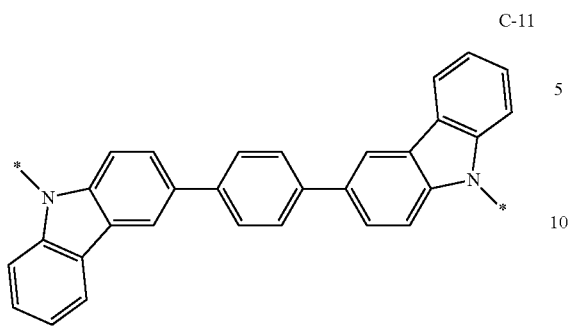
C-16
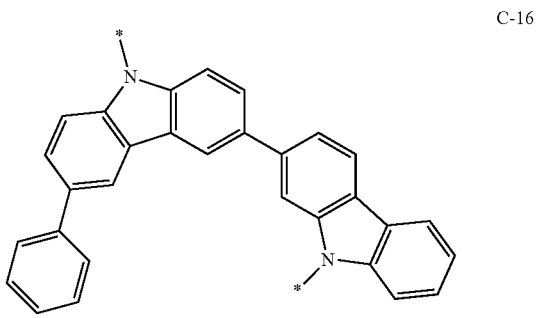
C-12
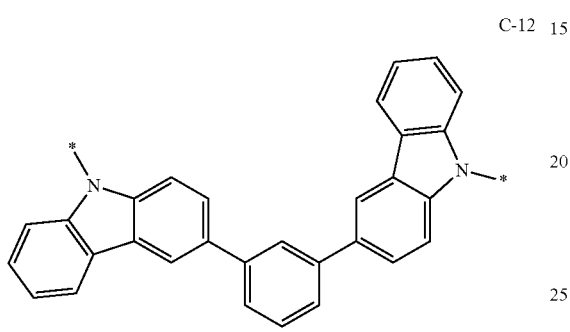
C-17
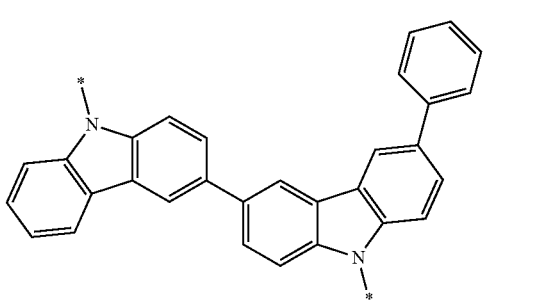
C-13
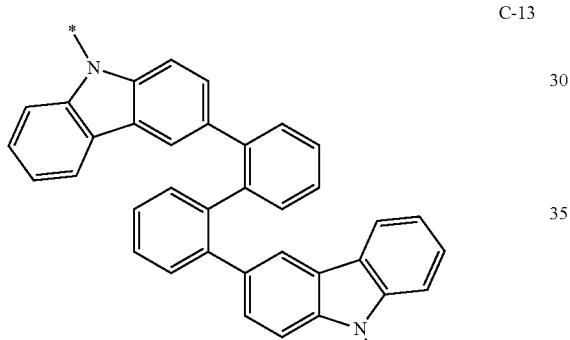
C-18
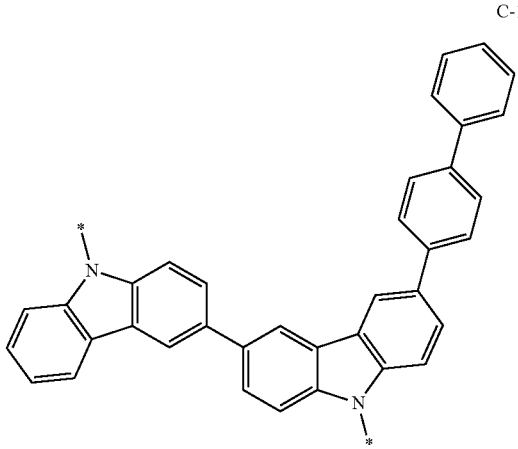
C-14
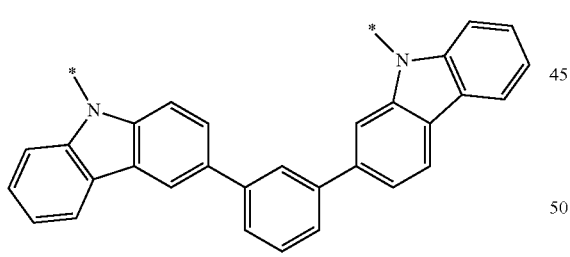
[Group III]
B-1
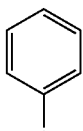
C-15
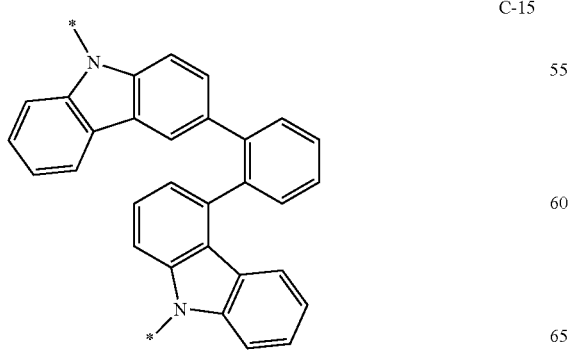
B-2
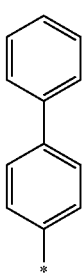

-continued
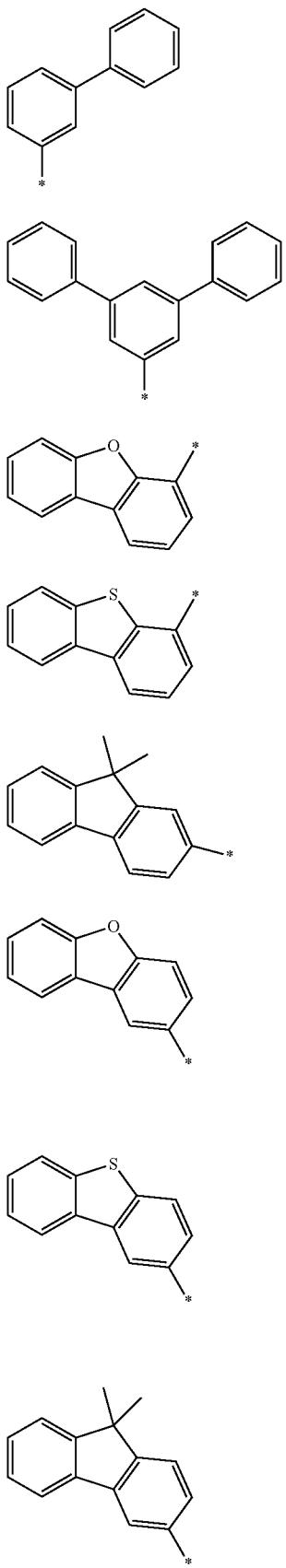
-continued
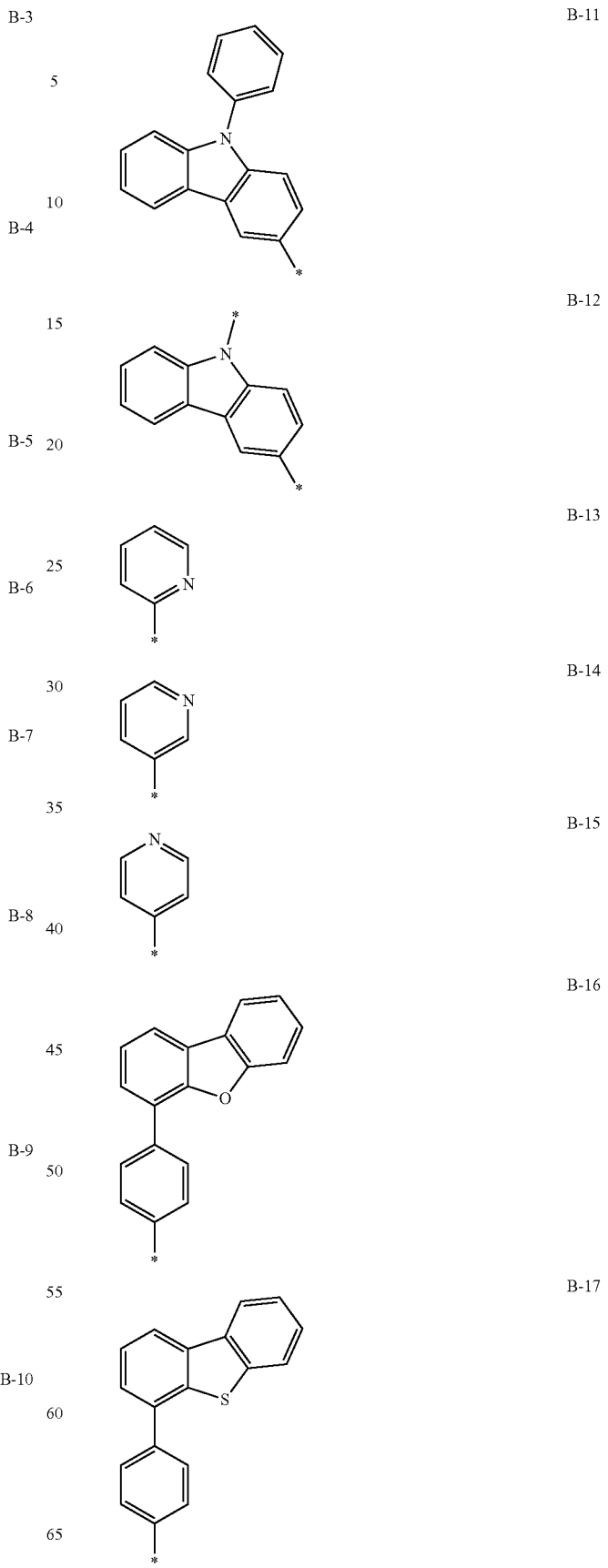

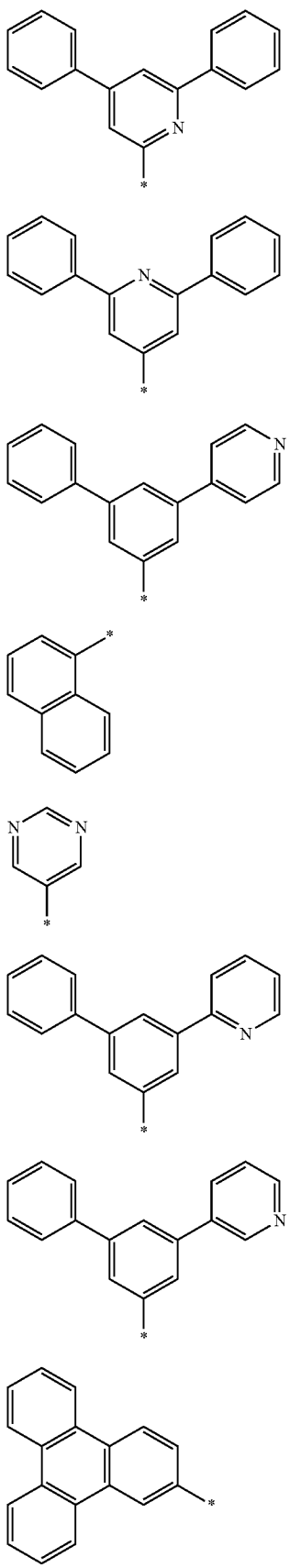
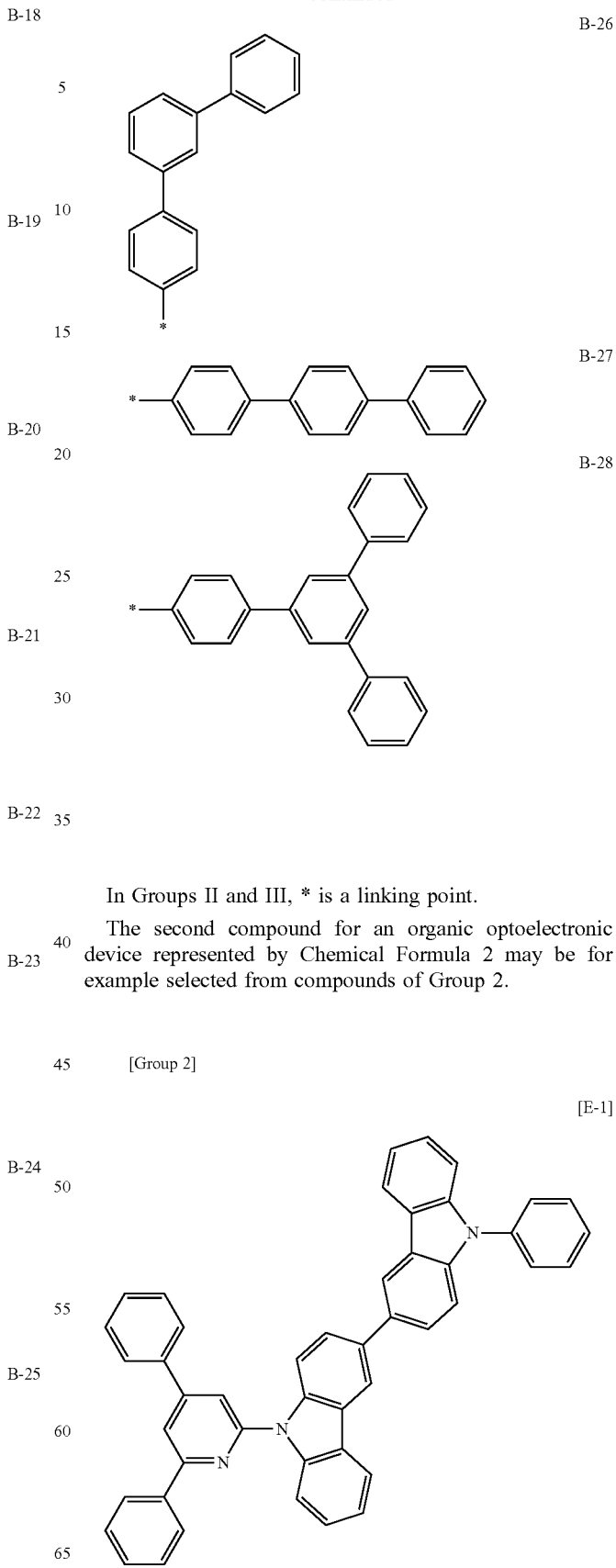
In Groups II and III, * is a linking point.
The second compound for an organic optoelectronic device represented by Chemical Formula 2 may be for example selected from compounds of Group 2.
[Group 2]
[E-1]

[E-2]
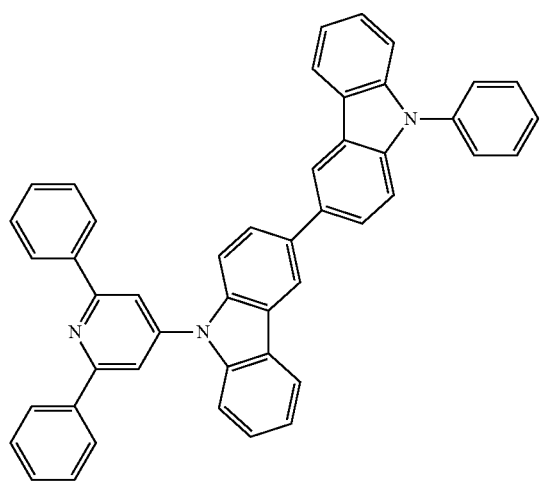
[E-3]
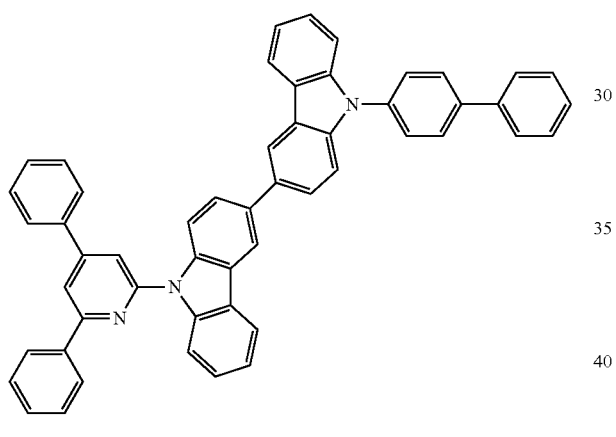
[E-4]
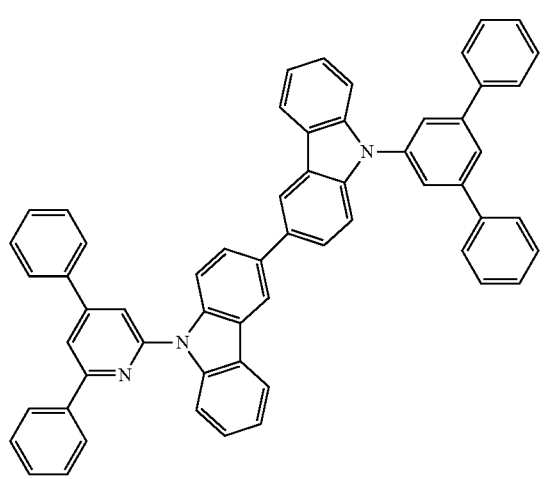
[E-5]
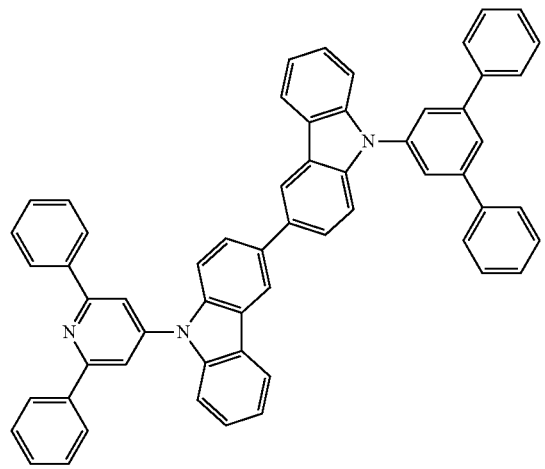
[E-6]
[E-7]
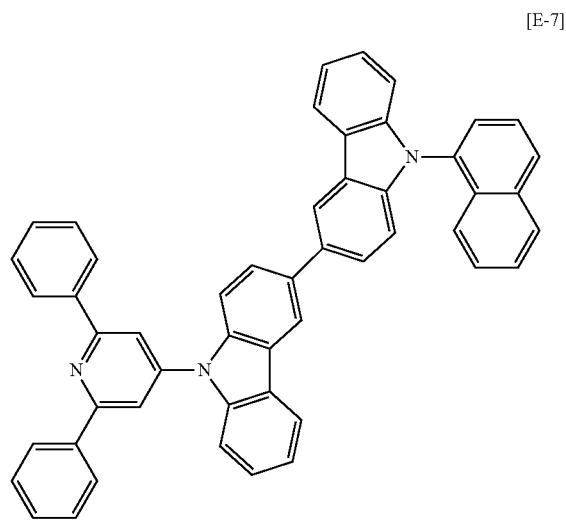

[E-8]
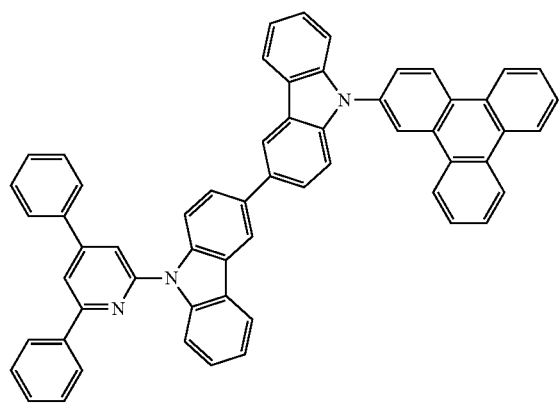
[E-9]
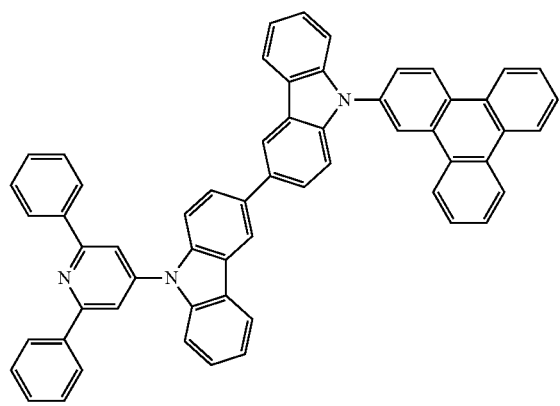
[E-10]
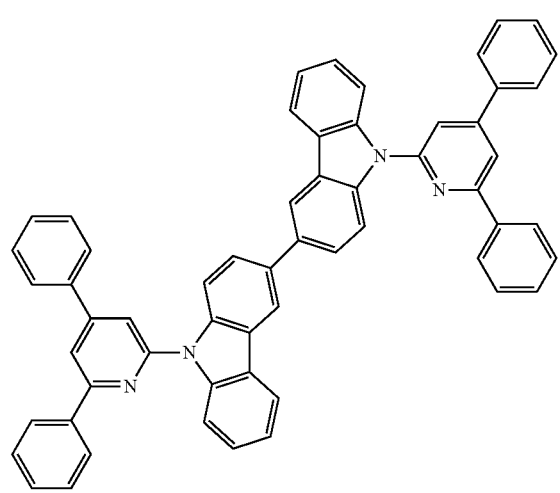
[E-11]
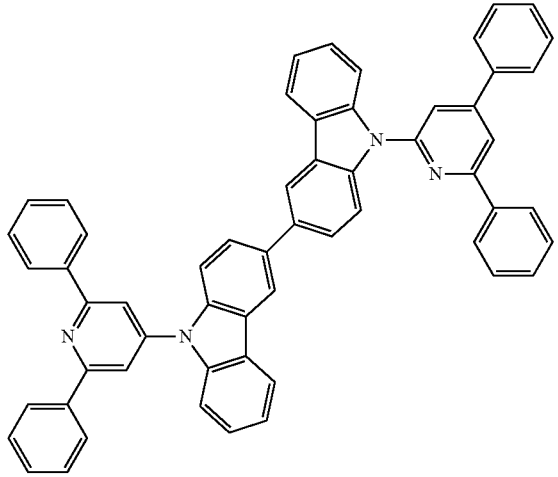
[E-12]
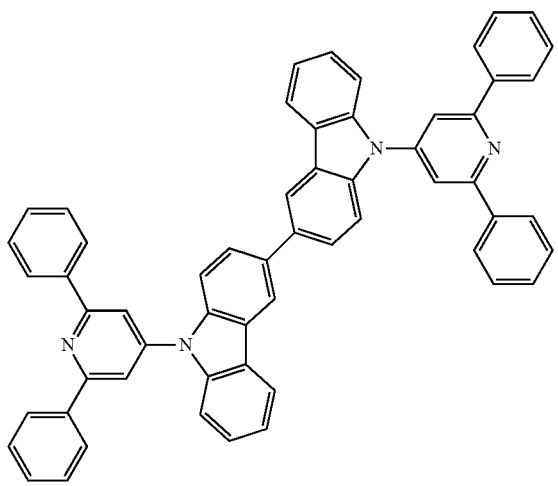
[E-13]
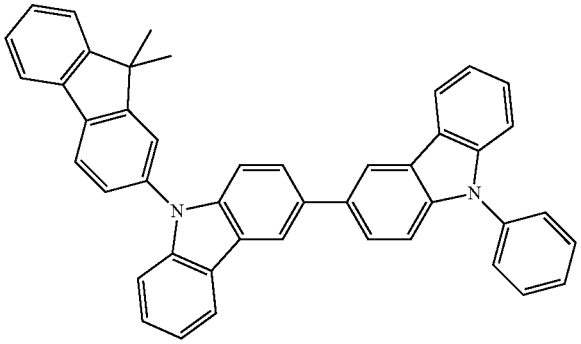

[E-14]
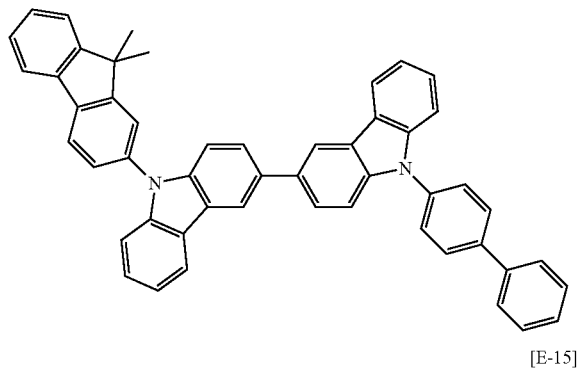
[E-15]
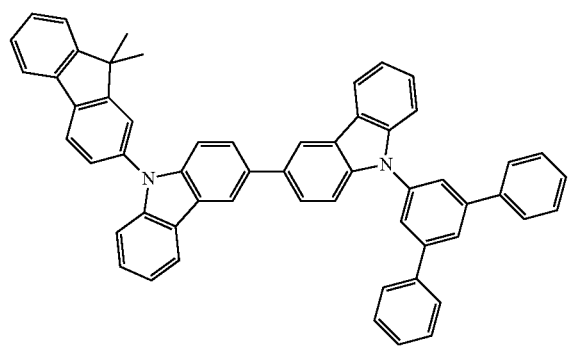
[E-16]
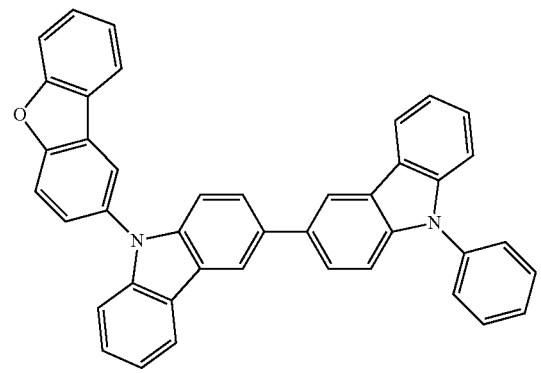
[E-17]
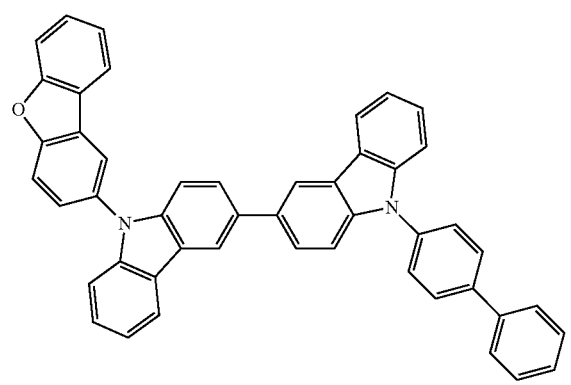
[E-18]
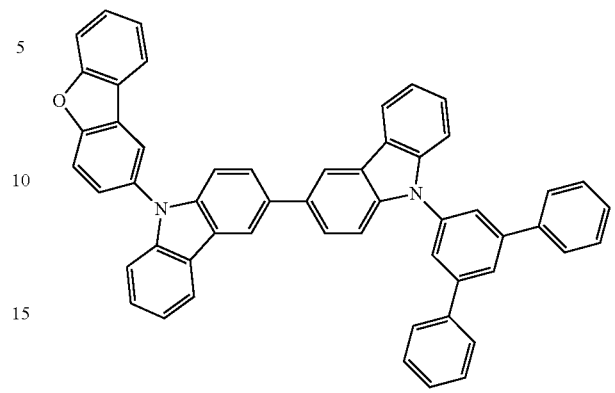
[E-19]
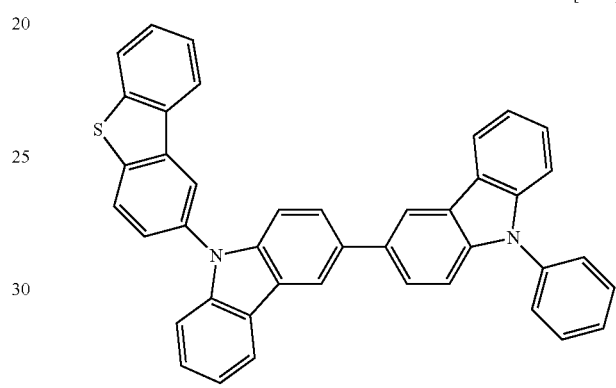
[E-20]
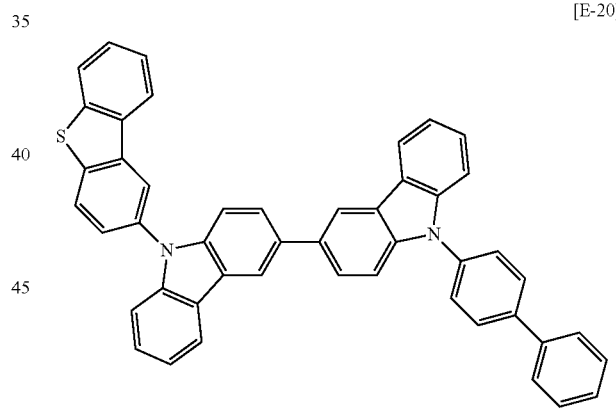
[E-21]
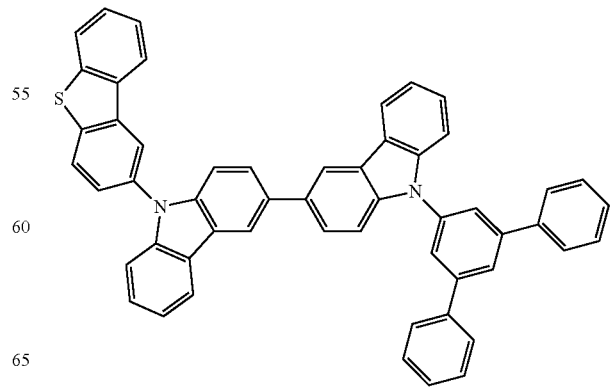

[E-22]
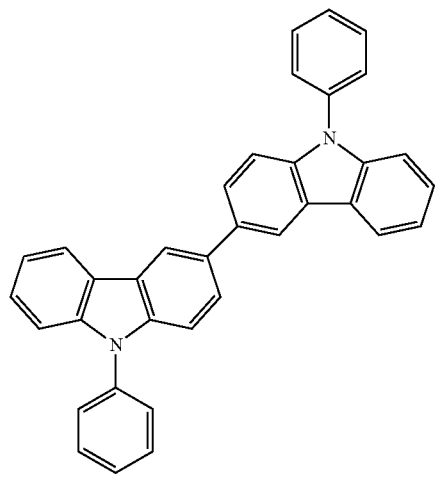
[E-23]
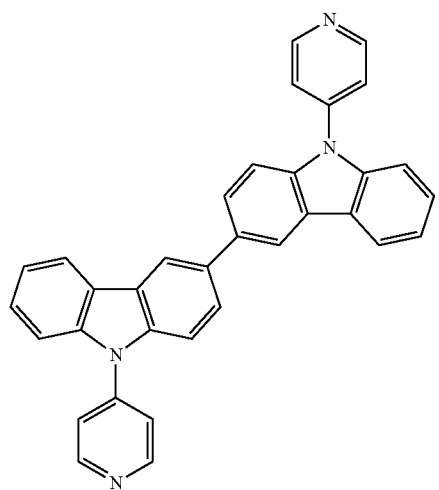
[E-24]
[E-25]
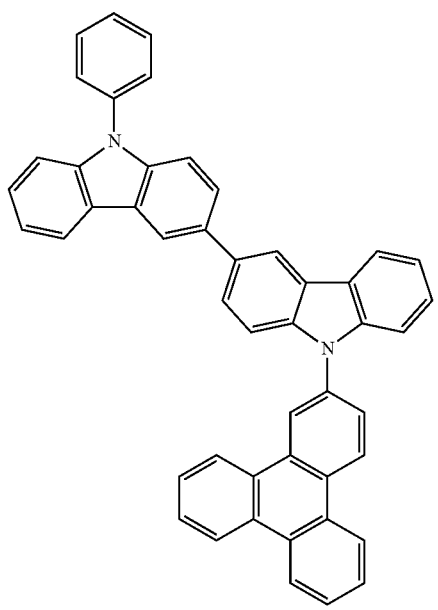
[E-26]
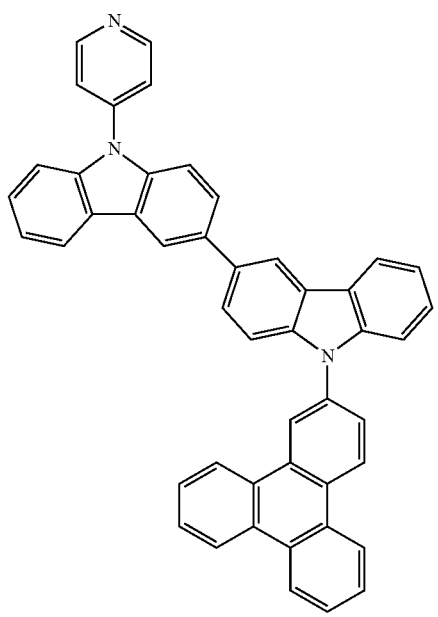

[E-27]
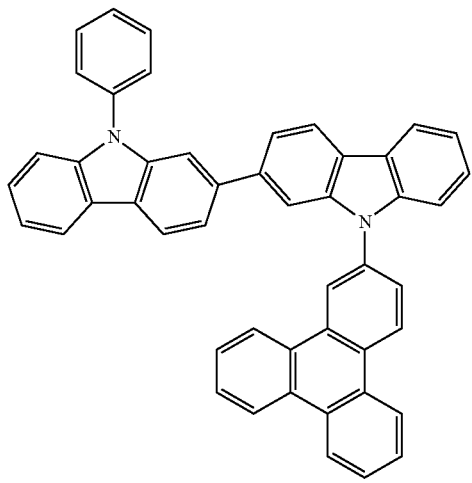
[E-28]
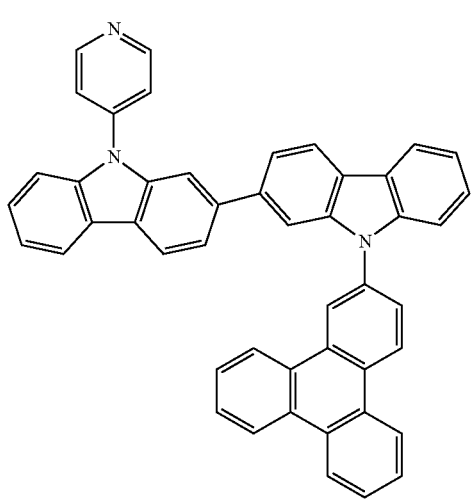
[E-29]
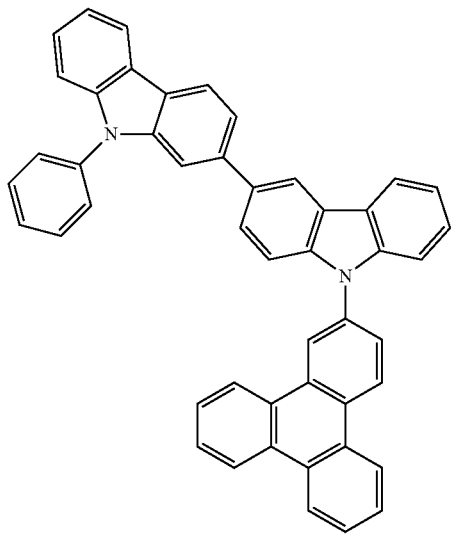
[E-30]
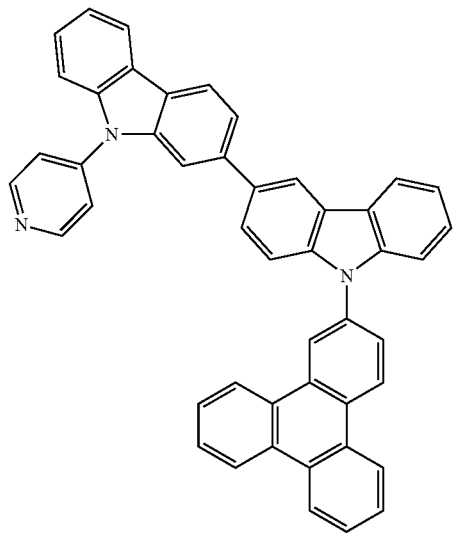
[E-31]
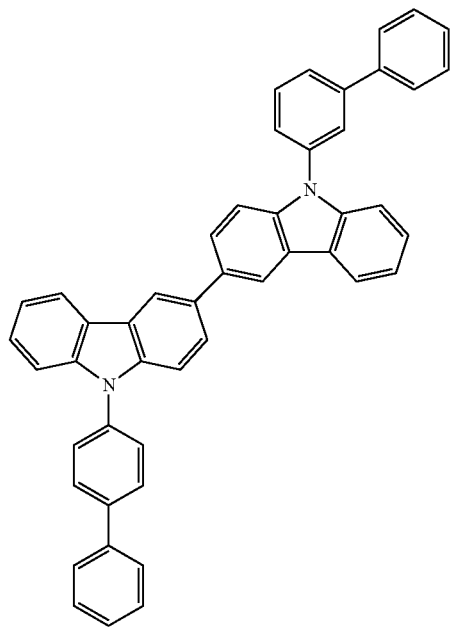

[E-32]
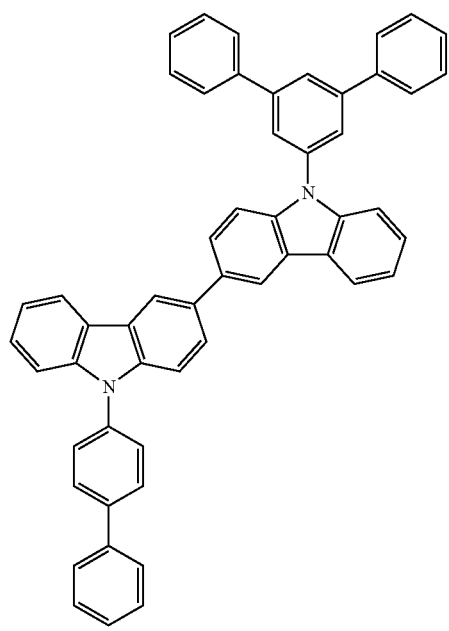
[E-33]
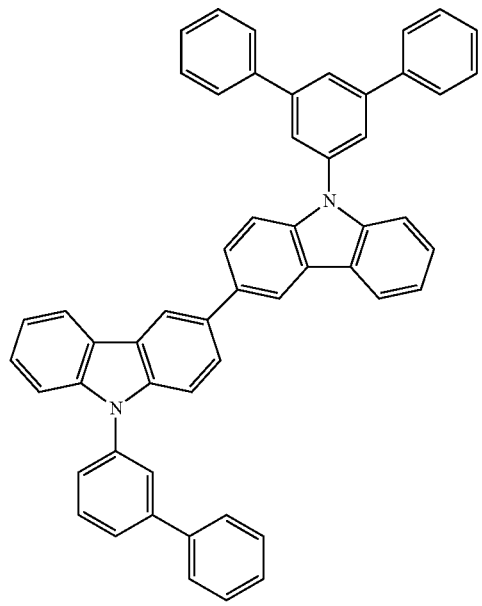
[E-34]
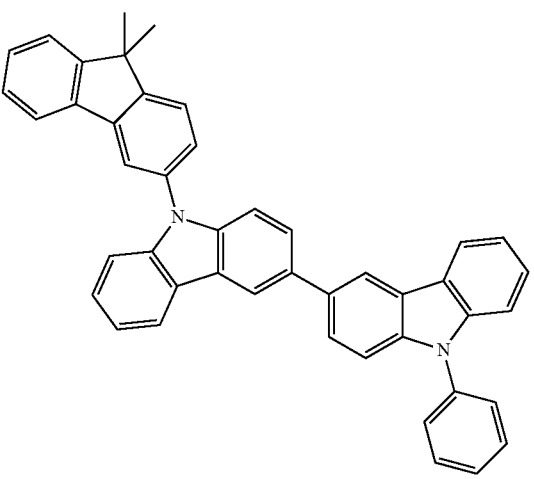
[E-35]
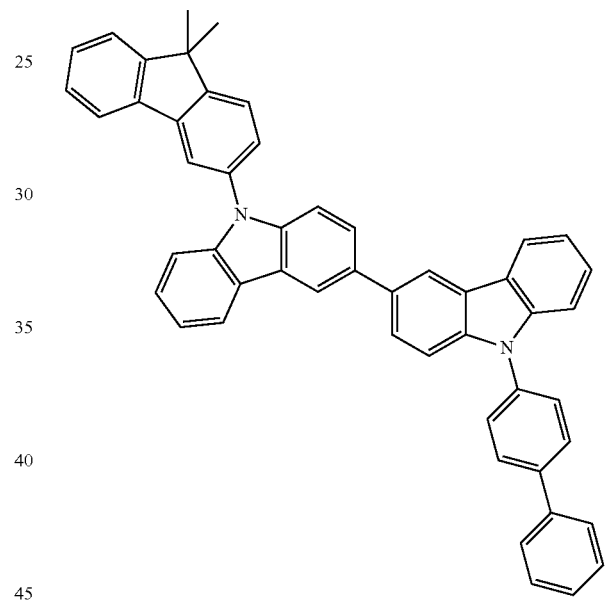
[E-36]
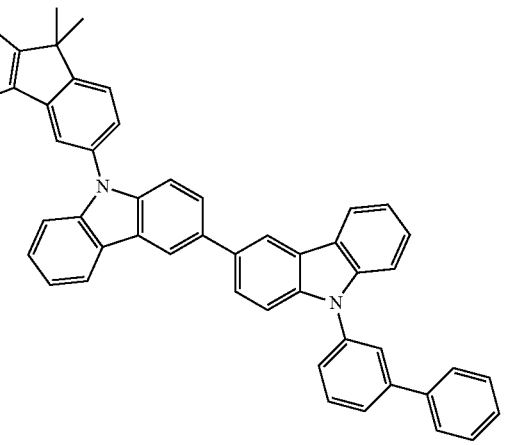

[E-37]
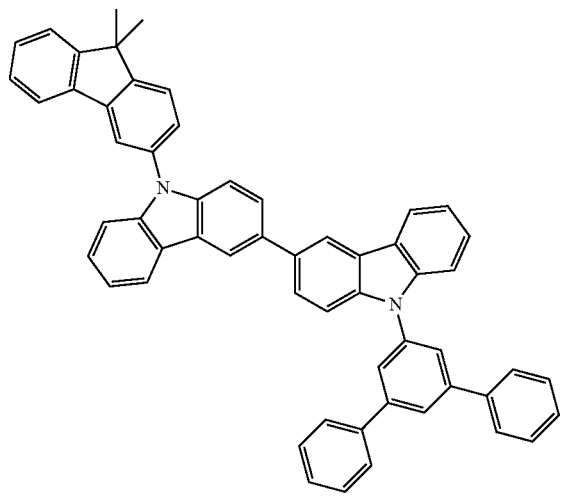
[E-38]
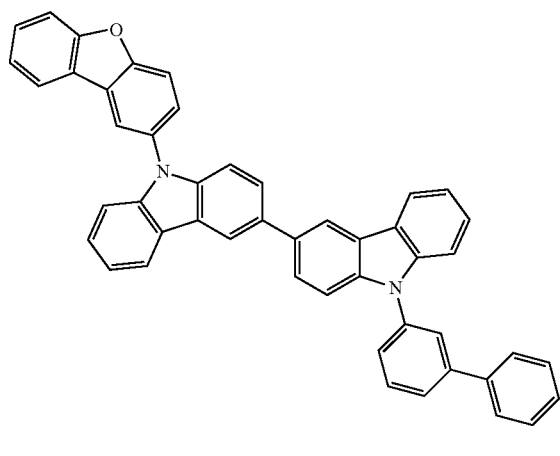
[E-39]
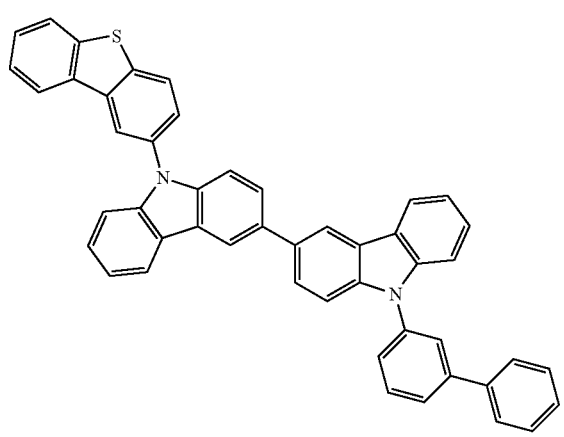
[E-40]
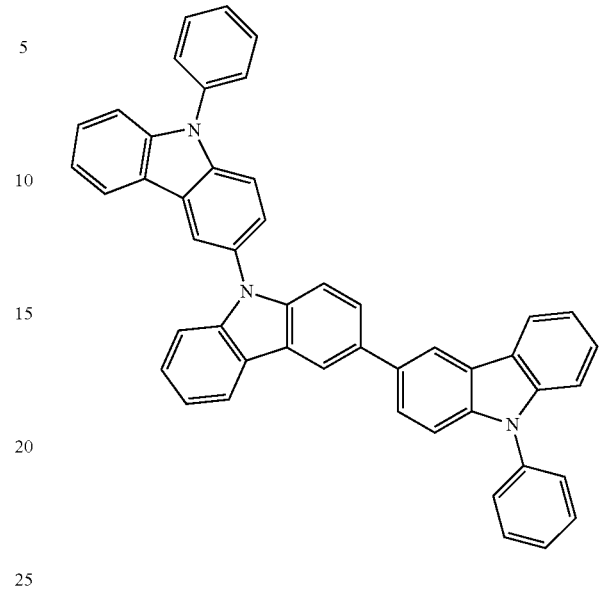
[E-41]
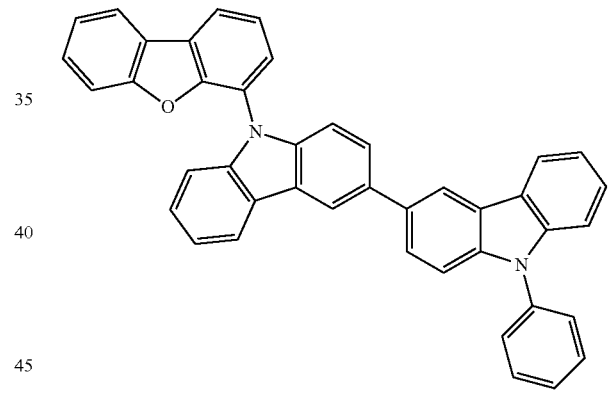
[E-42]
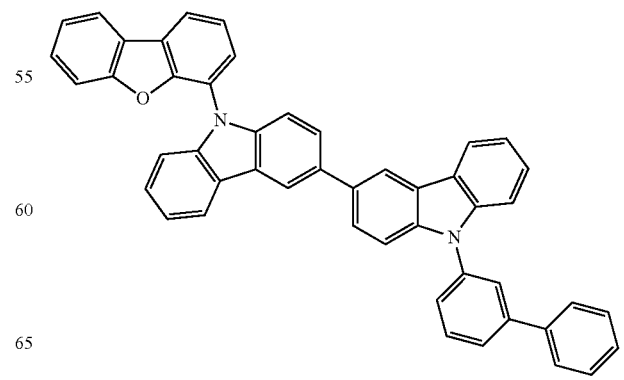

[E-43]
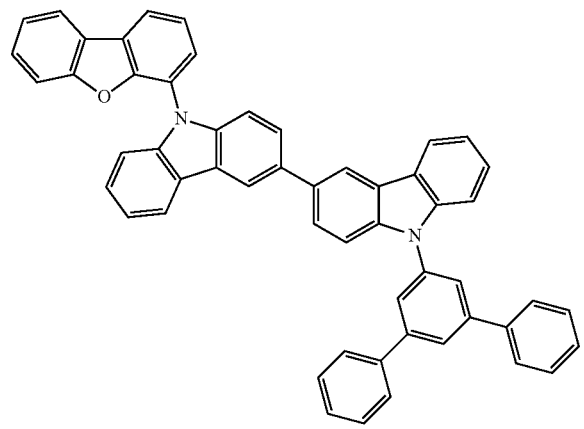
[E-46]
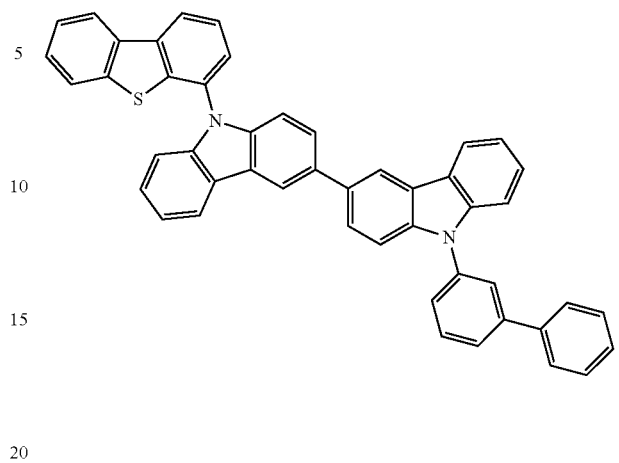
[E-44]
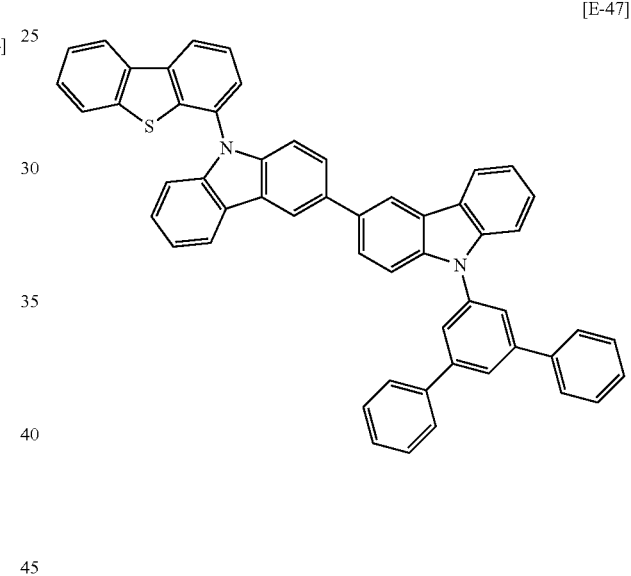
[E-47]
[E-45]
[E-48]
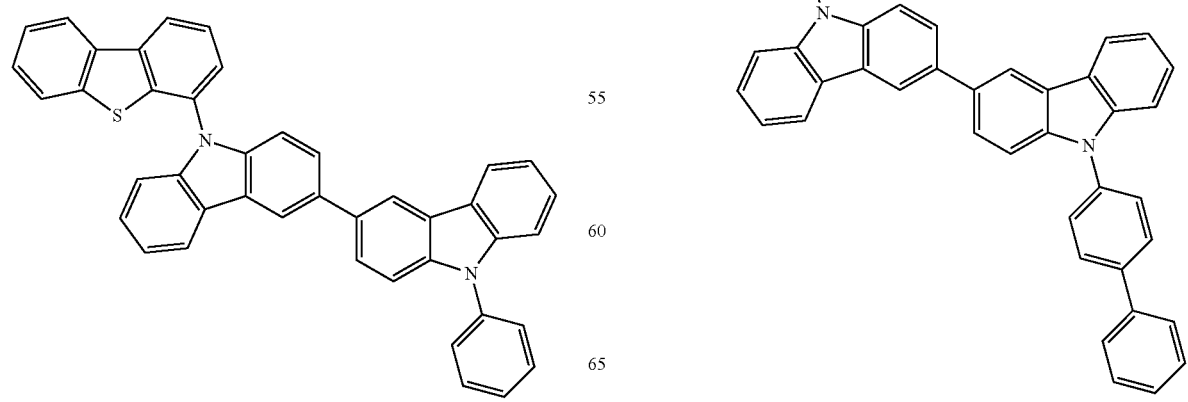

[E-49]
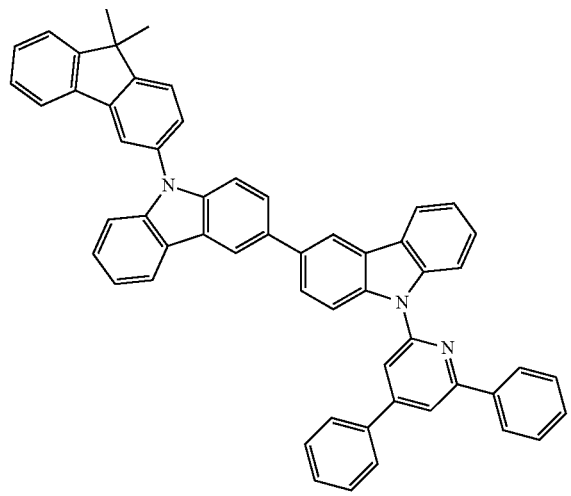
[E-50]
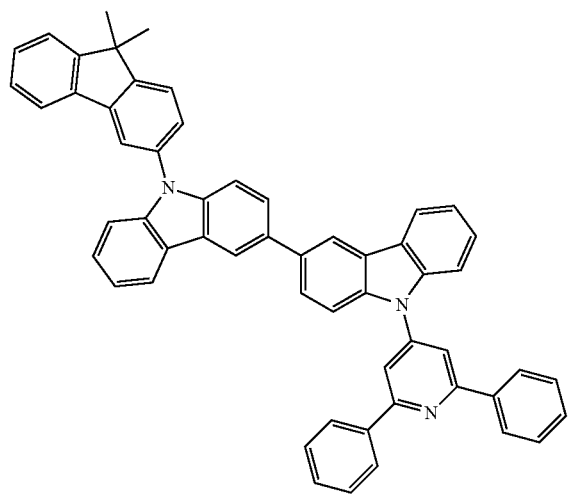
[E-51]
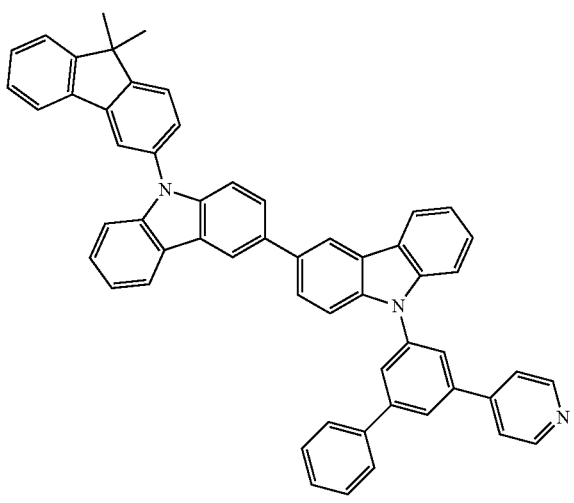
[E-52]
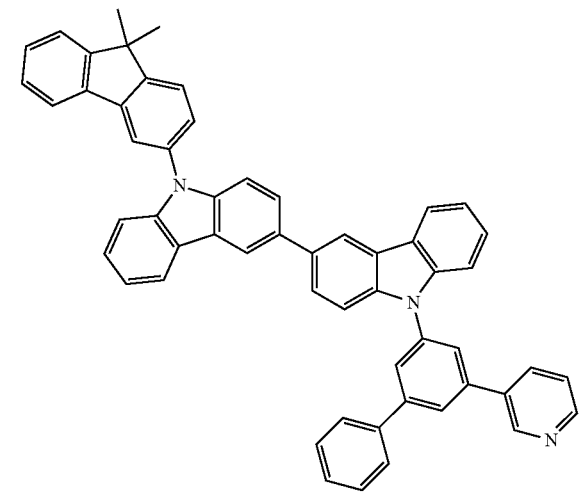
[E-53]
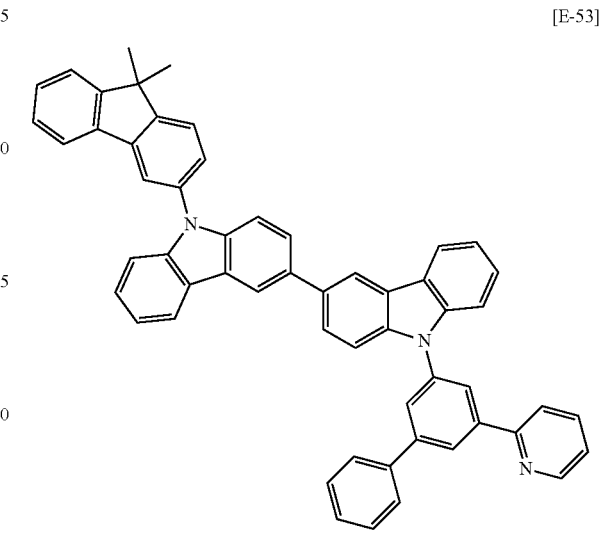
[E-54]
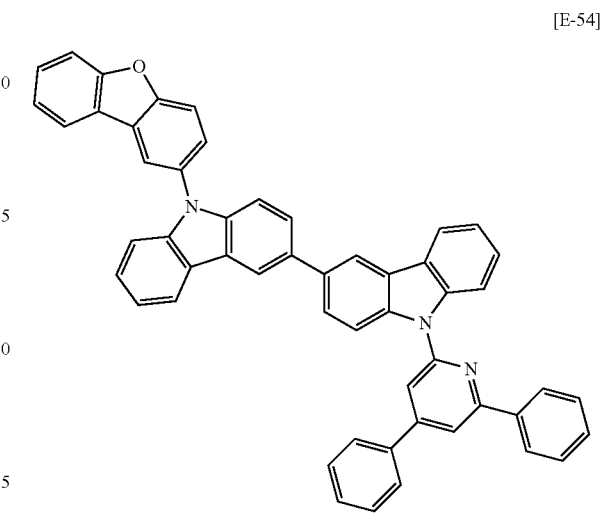

[E-55]
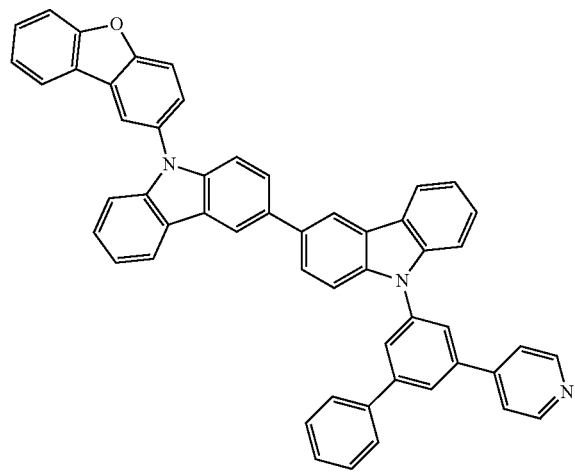
[E-58]
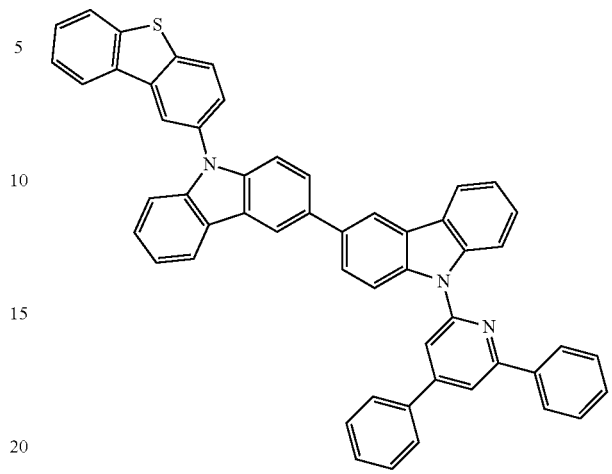
[E-56]
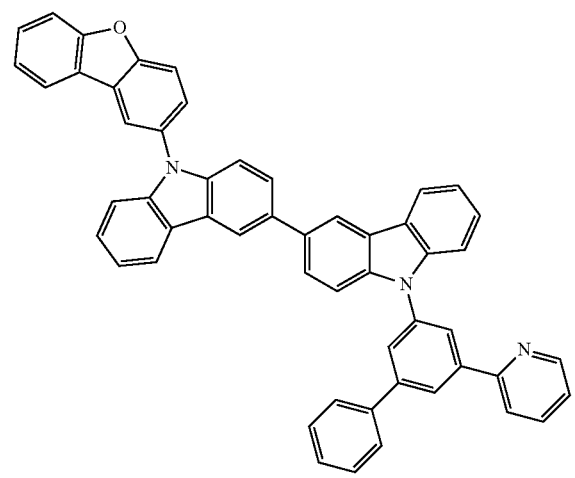
[E-59]
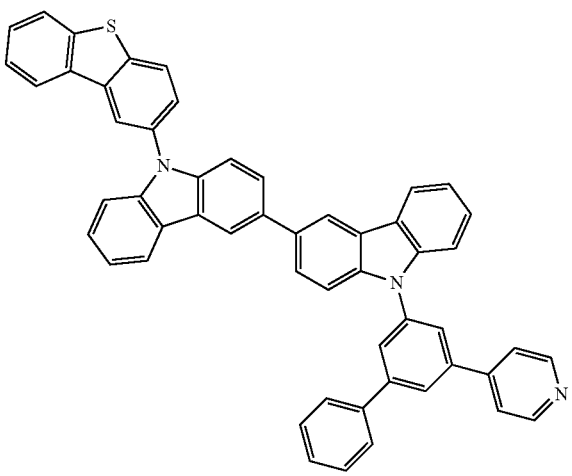
[E-57]
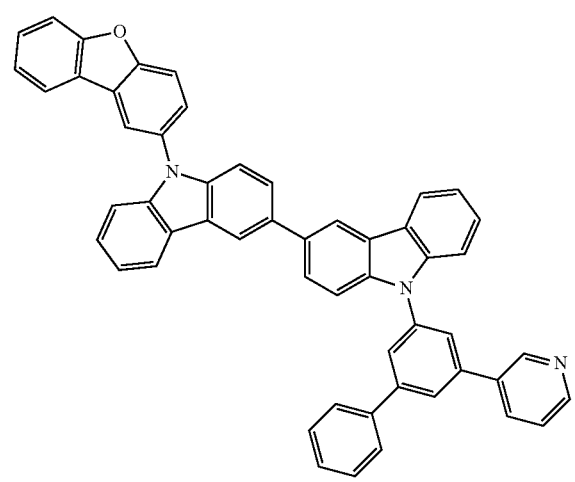
[E-60]
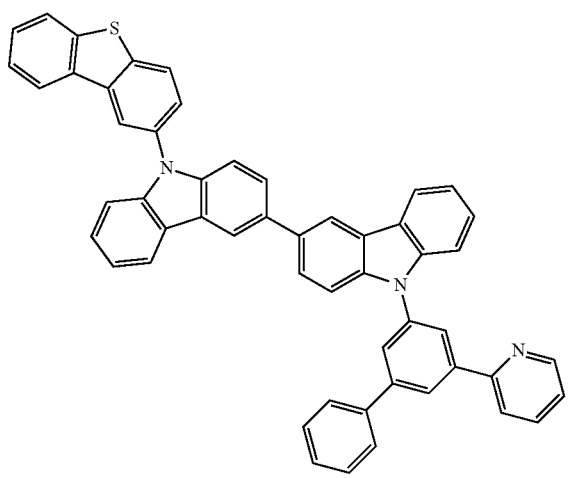

[E-61]
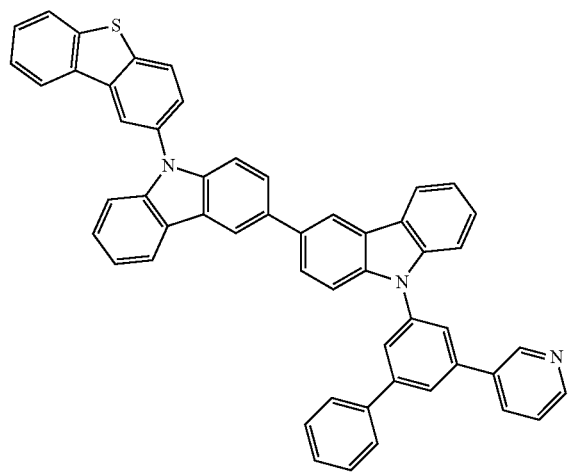
[E-62]
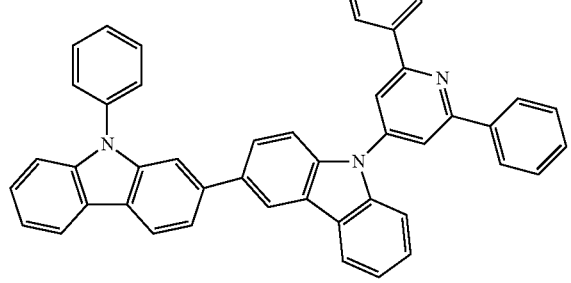
[E-63]
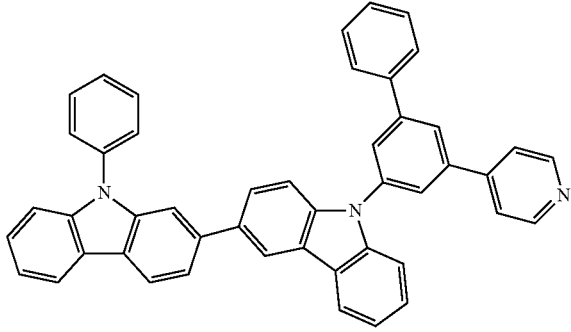
[E-64]
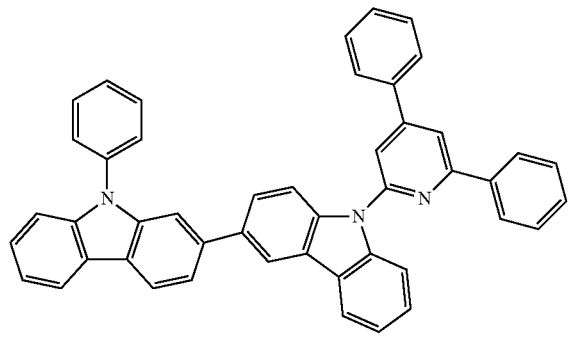
[E-65]
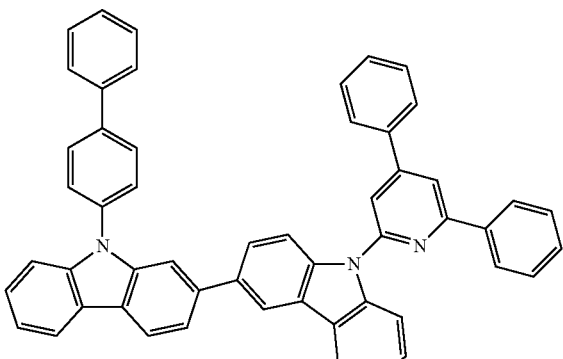
[E-66]
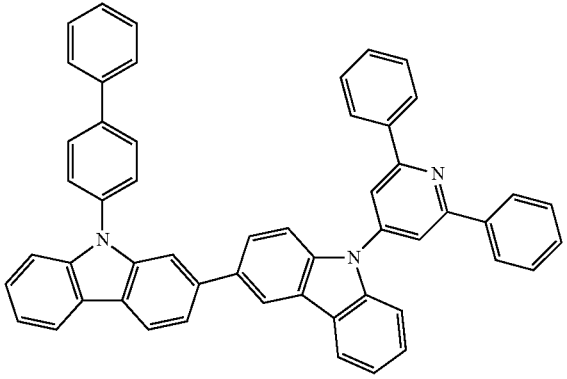
[E-67]
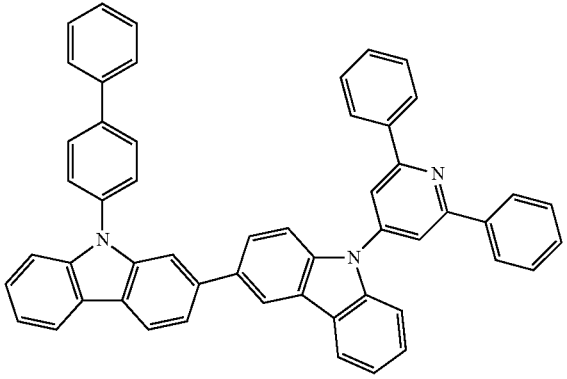
[E-68]
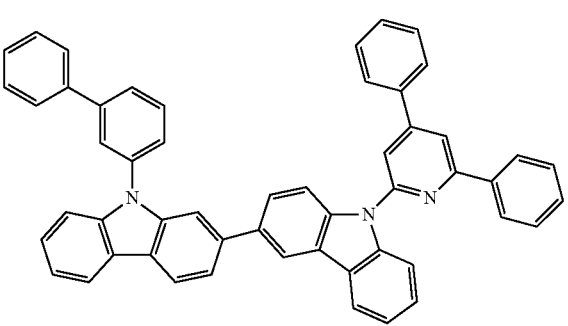

-continued
[E-69]
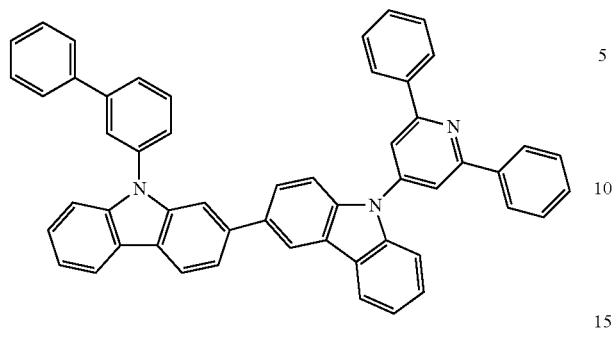
[E-70]
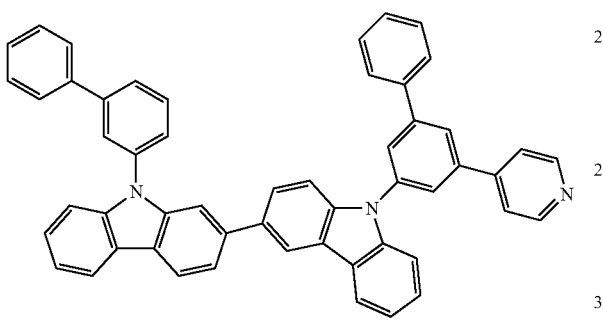
[E-71]
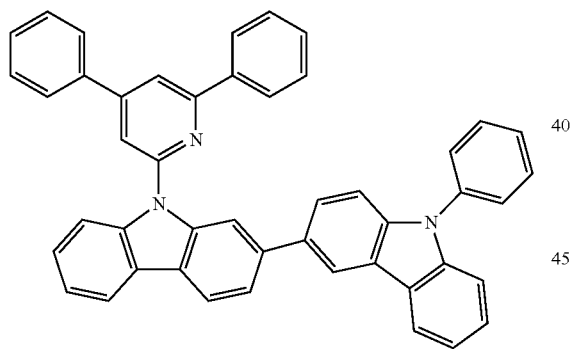
[E-72]
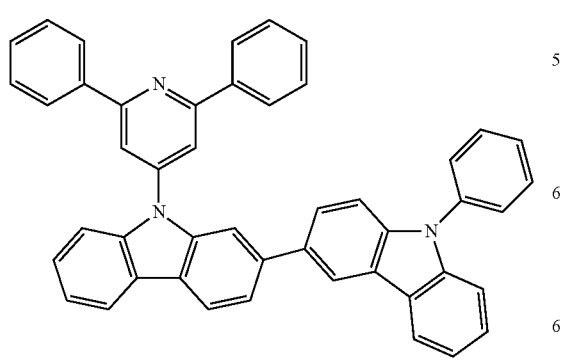
-continued
[E-73]
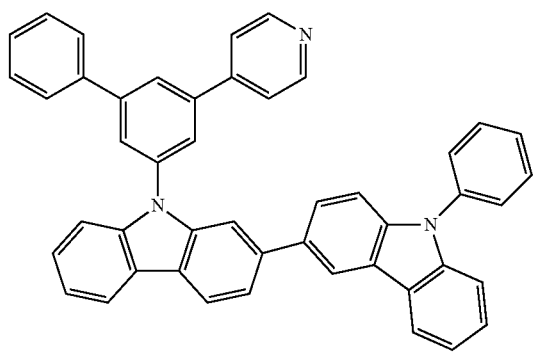
[E-74]
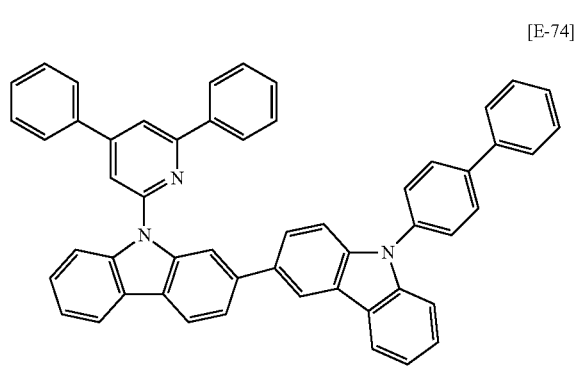
[E-75]
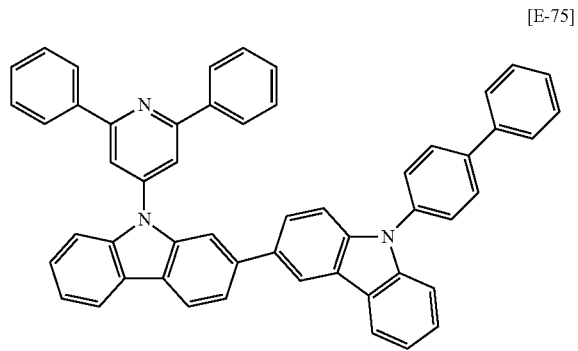
[E-76]
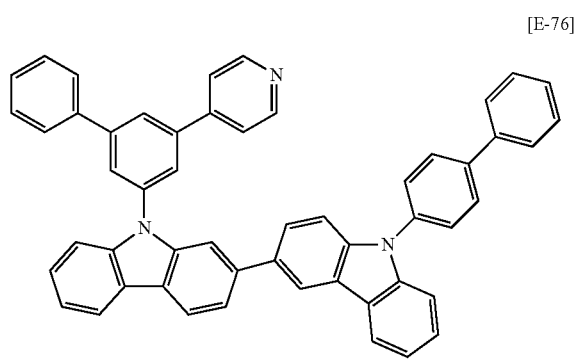

[E-77]
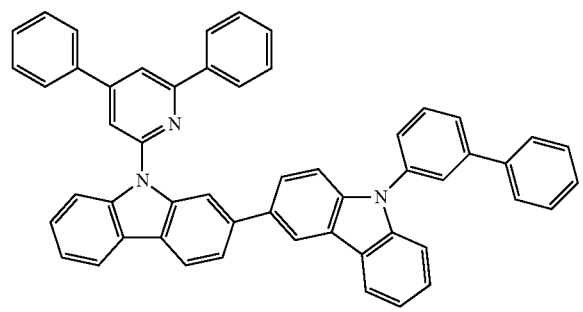
[E-78]
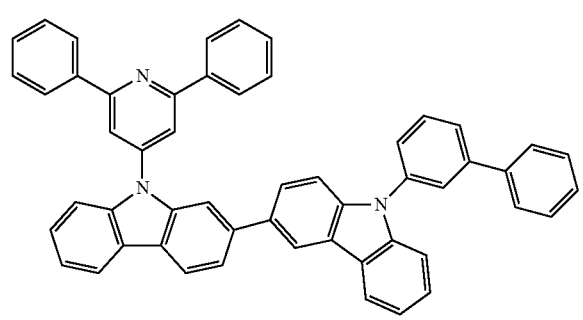
[E-79]
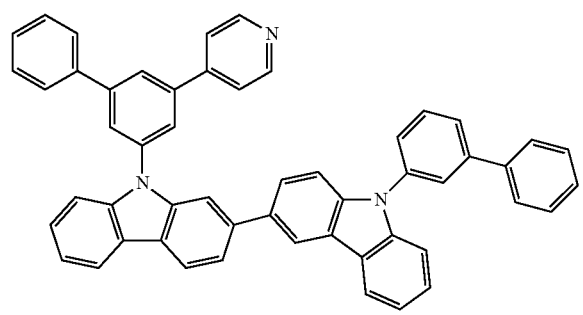
[E-80]
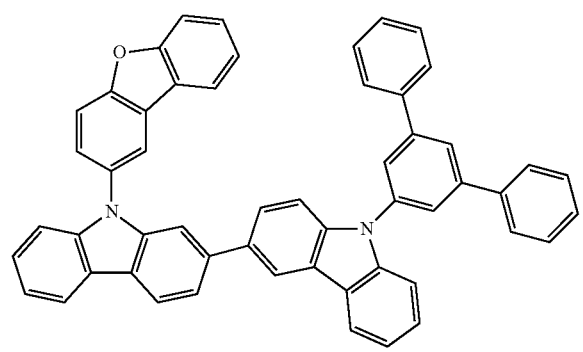
[E-81]
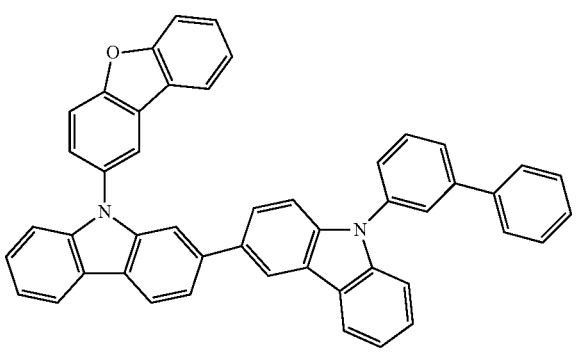
[E-82]
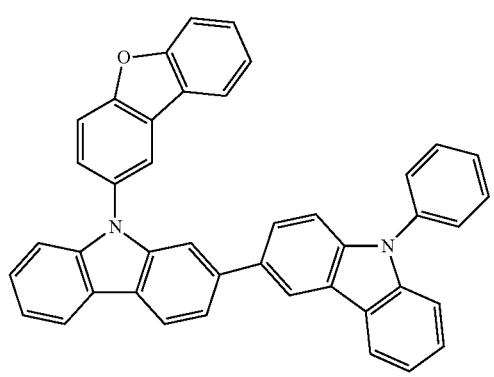
[E-83]
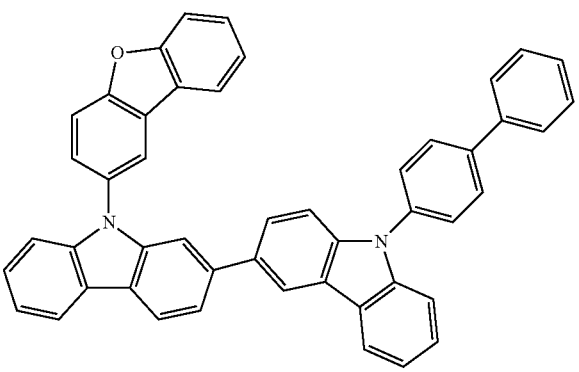
[E-84]
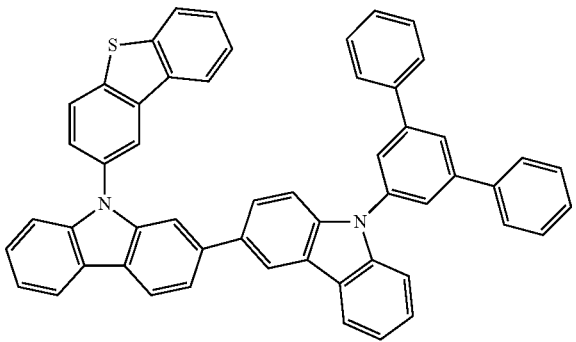

-continued
[E-85]
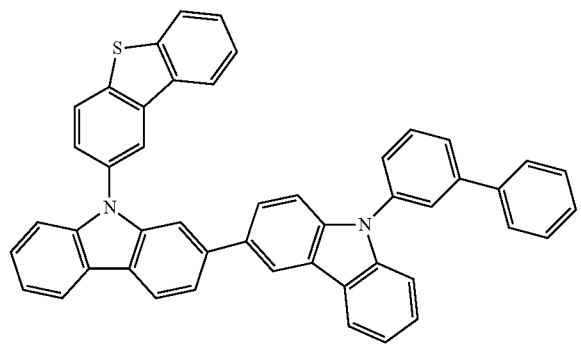
[E-86]
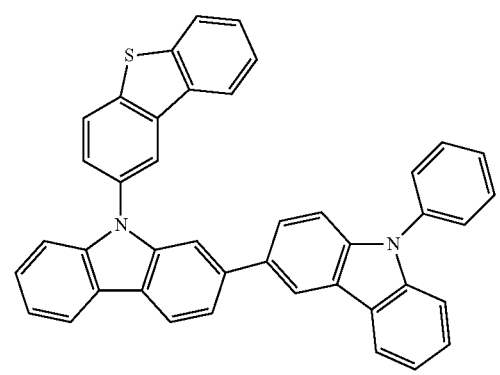
[E-87]
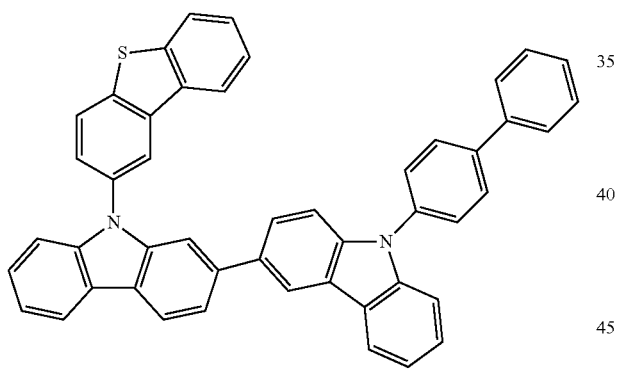
[E-88]
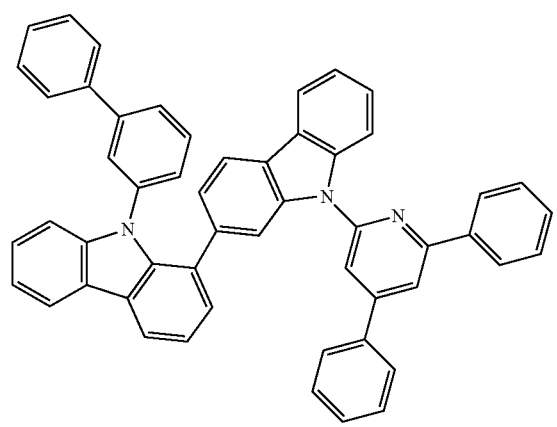
-continued
[E-89]
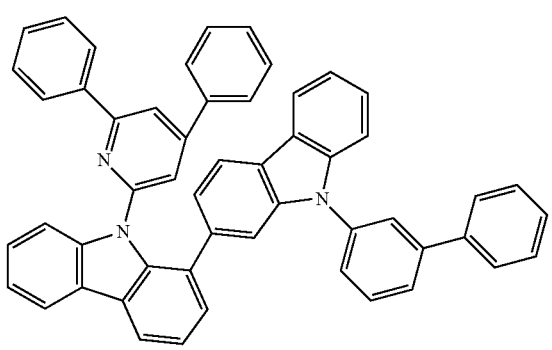
[E-90]
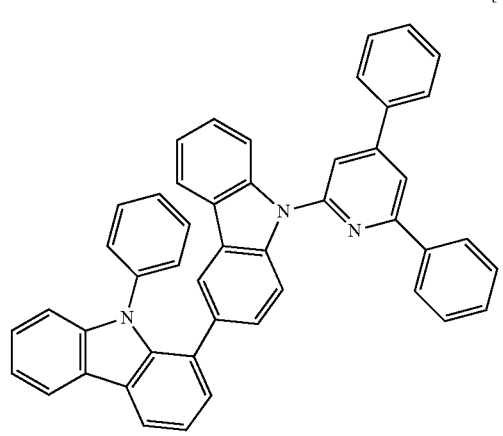
[E-91]
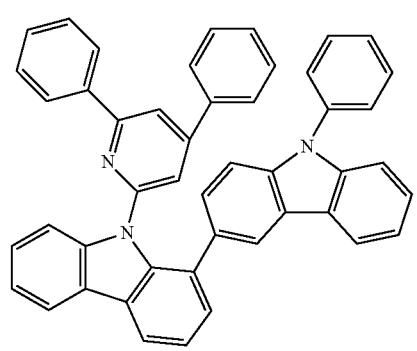
[E-92]
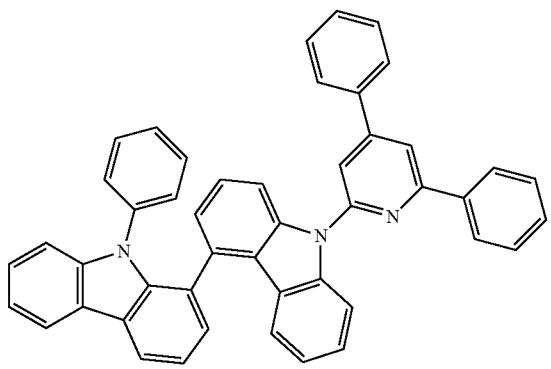

[E-93]
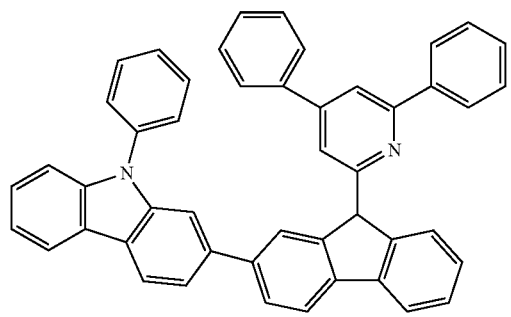
[E-94]
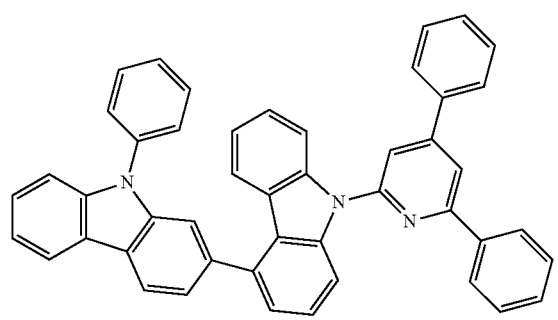
[E-95]
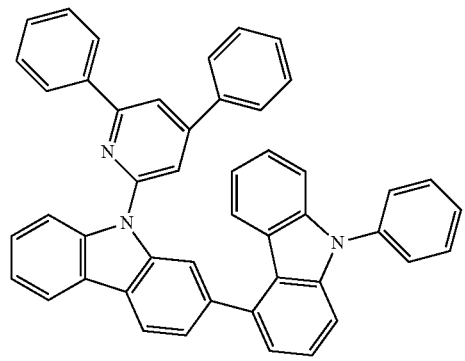
[E-96]
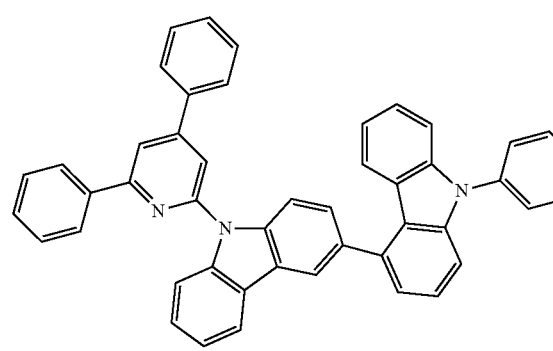
[E-97]
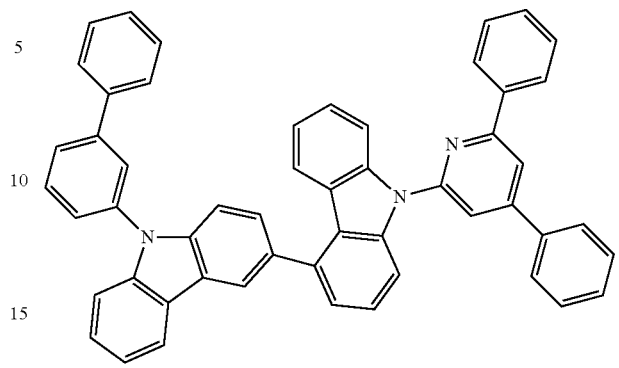
[E-98]
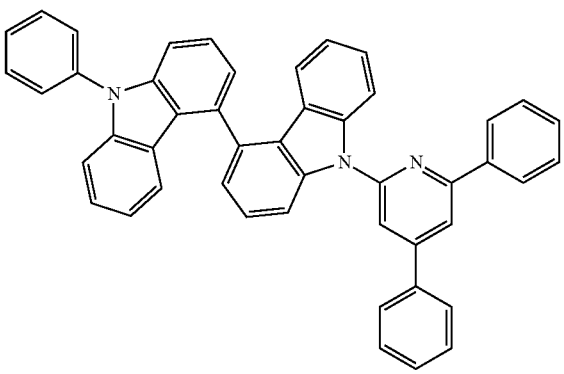
[E-99]
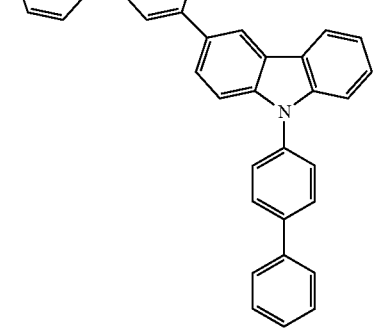

[E-100]
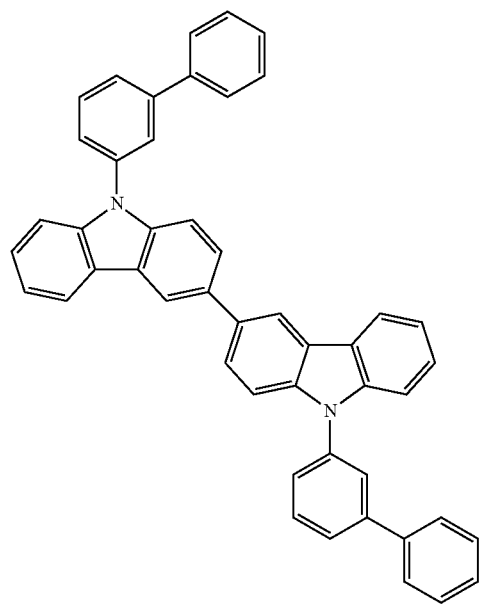
[E-101]
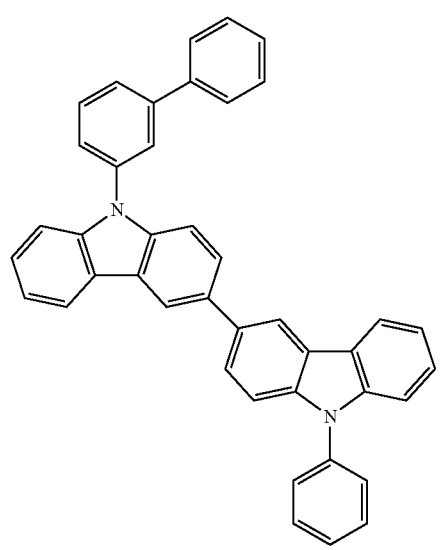
[E-102]
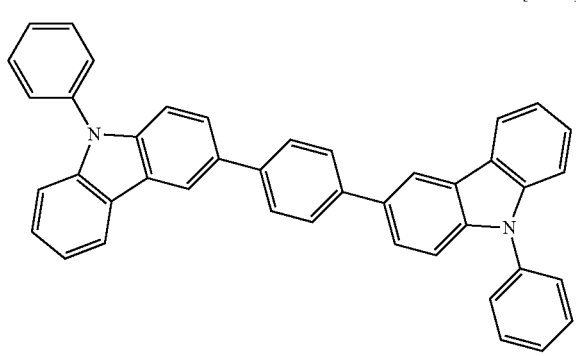
[E-103]
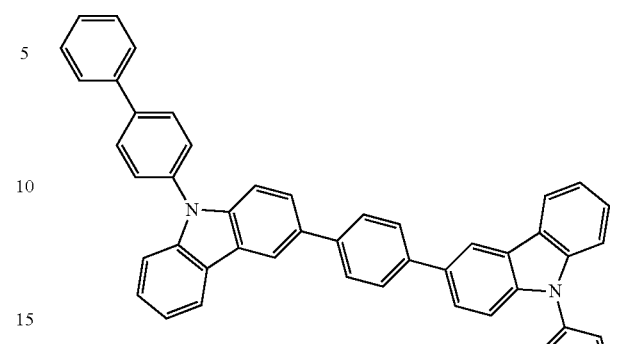
[E-104]
[E-105]
[E-106]

[E-107]
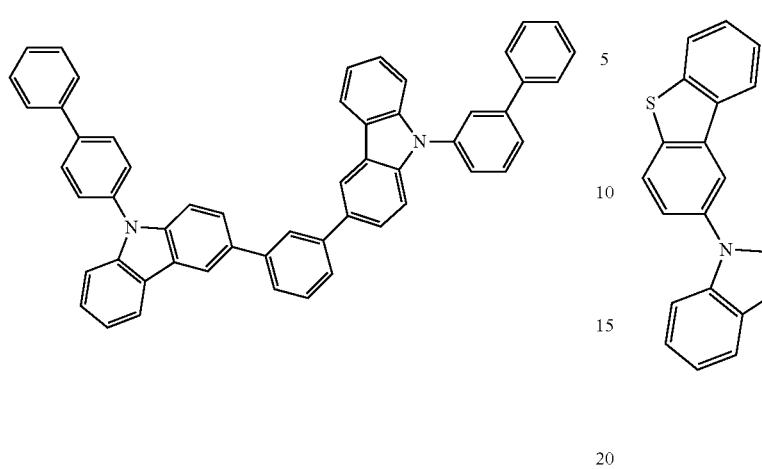
[E-110]
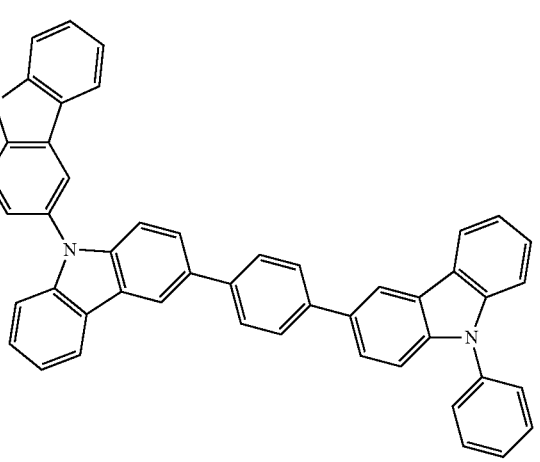
[E-108]
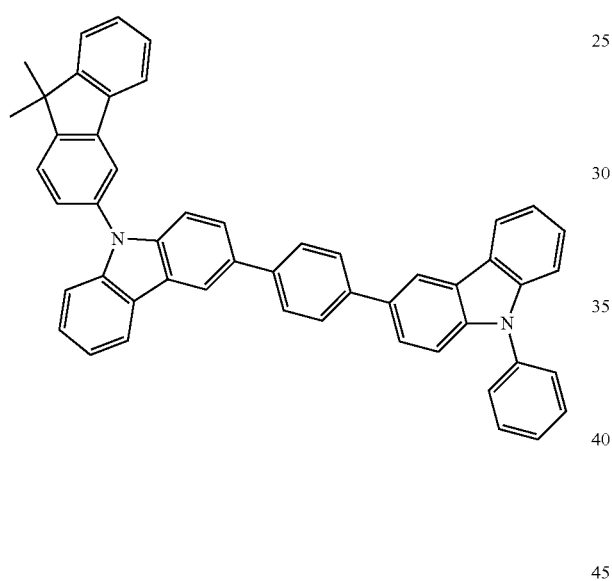
[E-111]
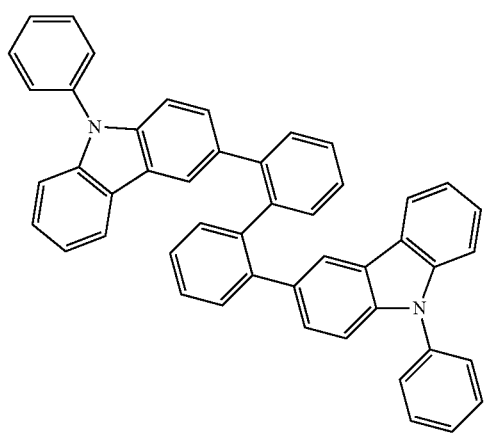
[E-109]
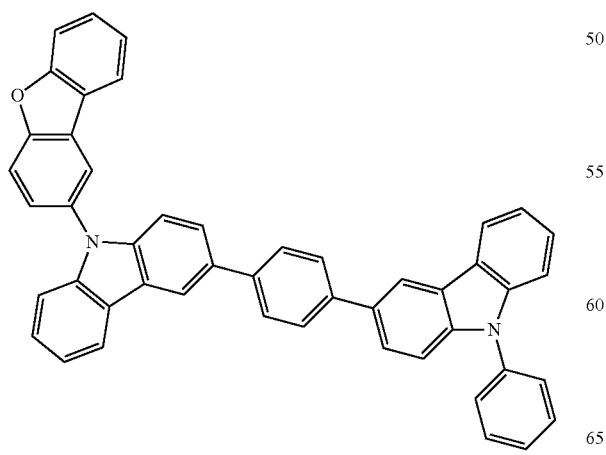
[E-112]
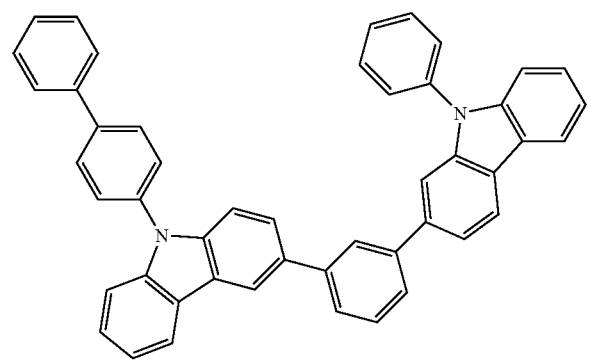

[E-113]
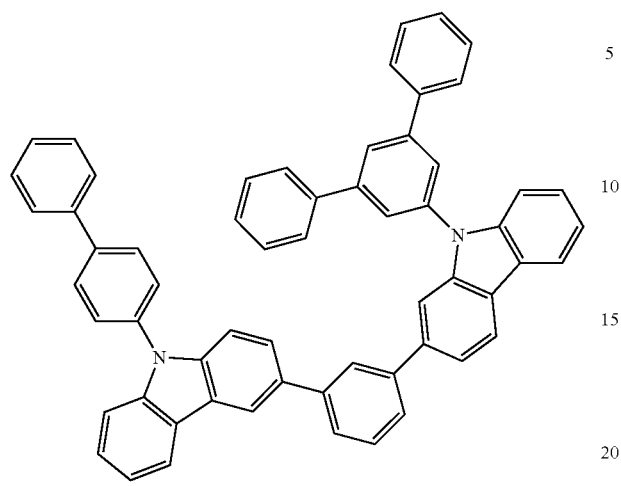
[E-114]
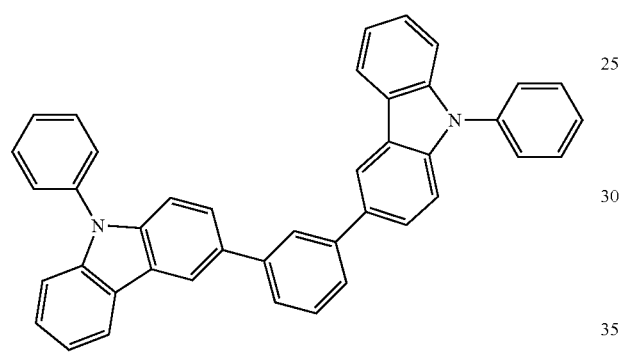
[E-115]
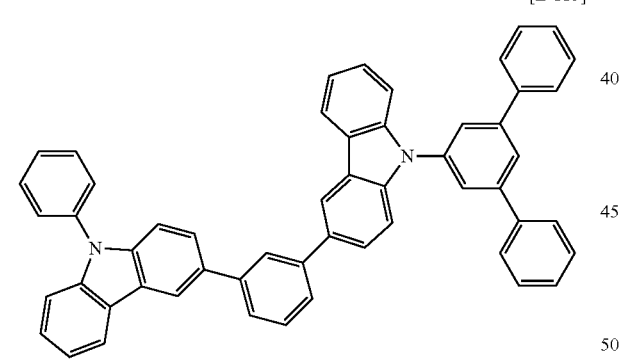
[E-116]
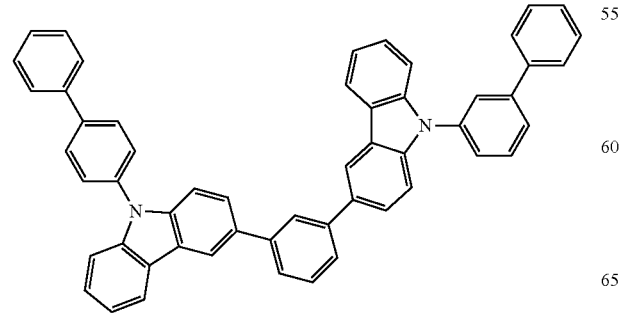
[E-117]
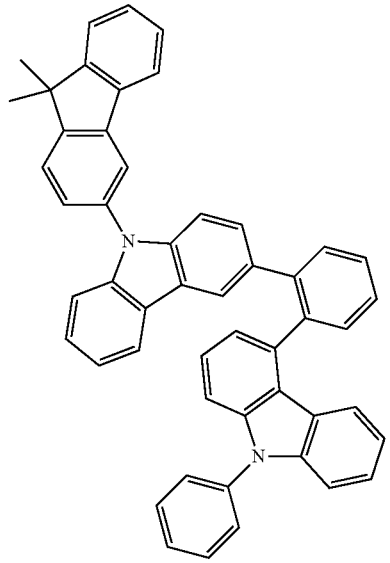
[E-118]
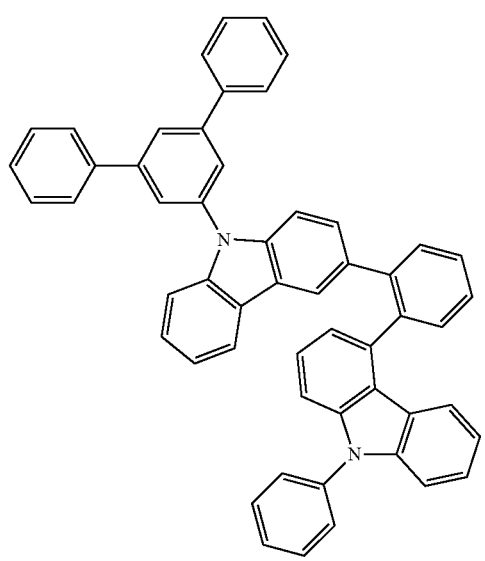

[E-119]
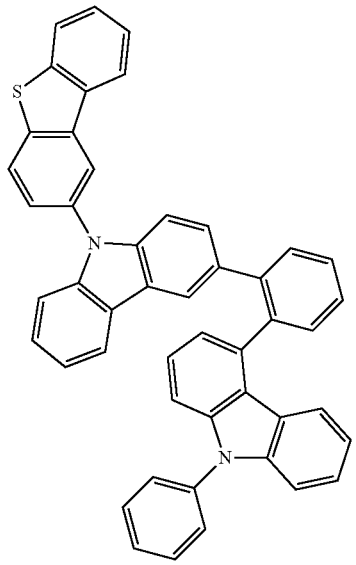
[E-120]
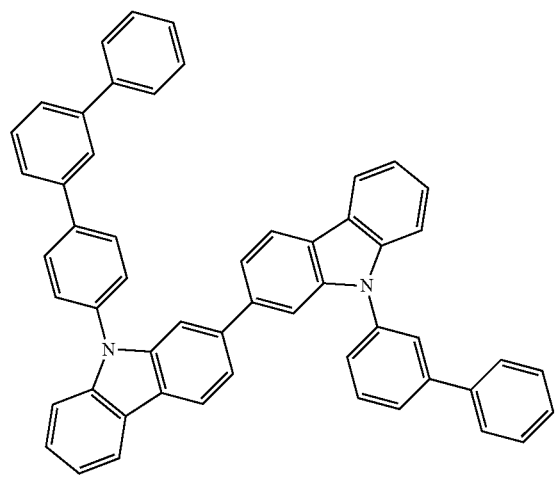
[E-121]
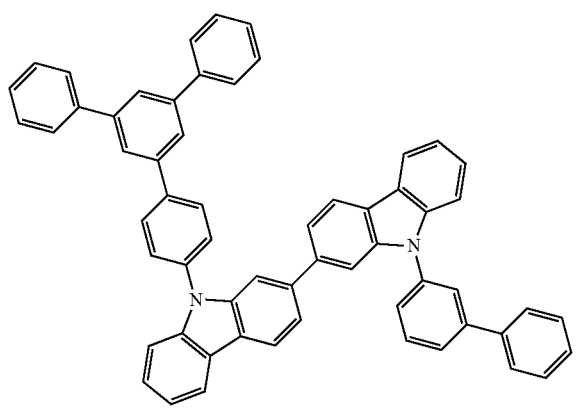
[E-122]
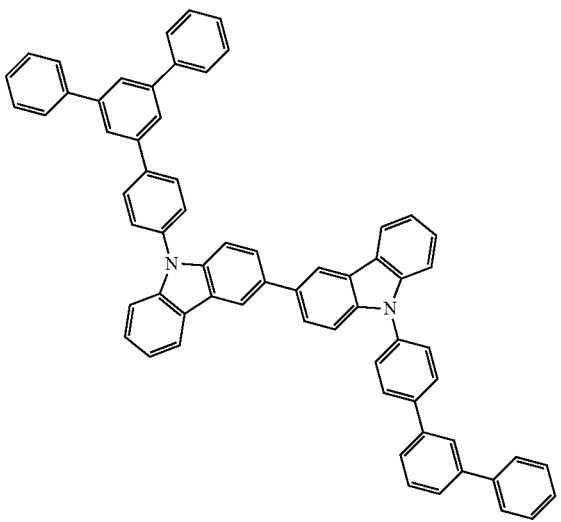
[E-123]
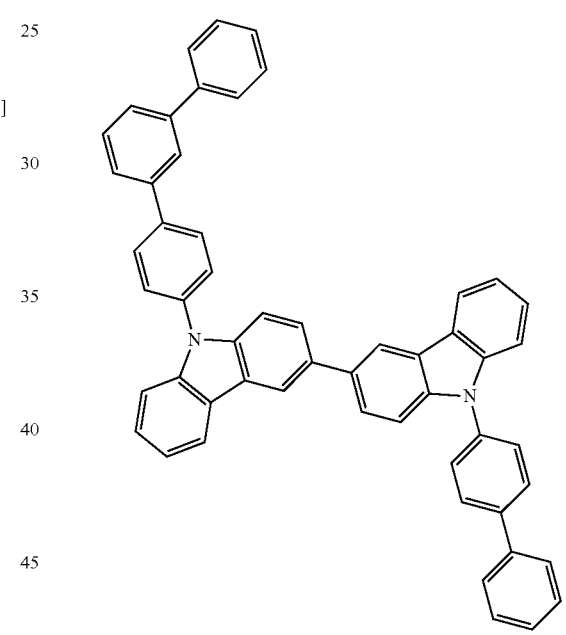
[E-124]
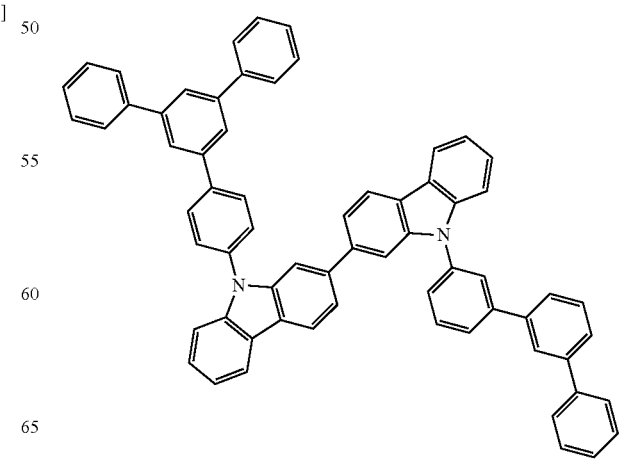

[E-125]
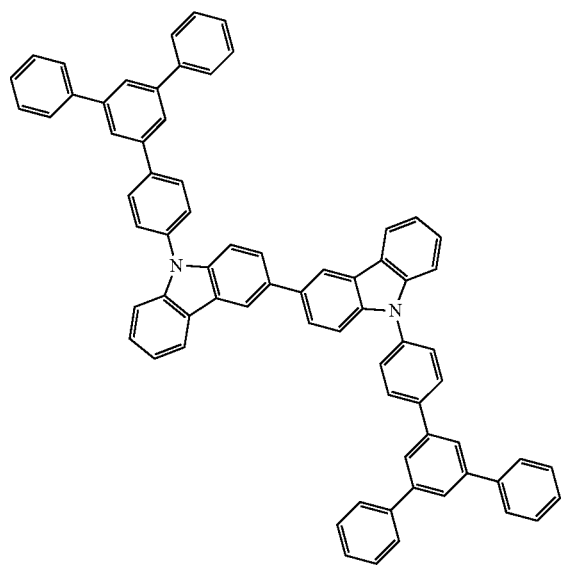
[E-126]
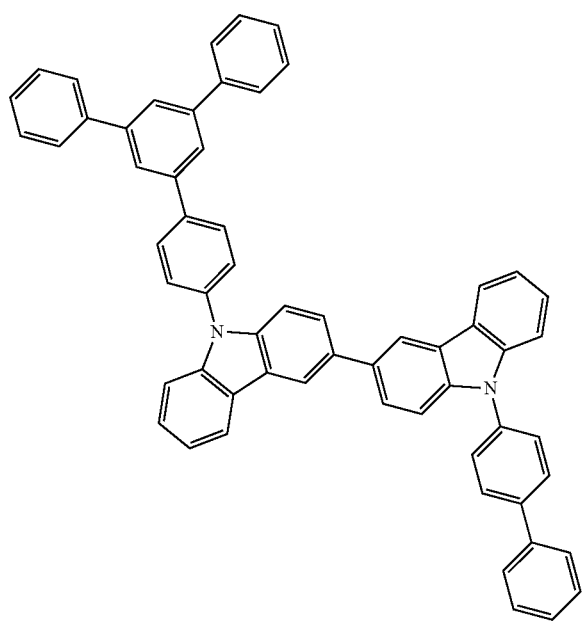
[E-127]
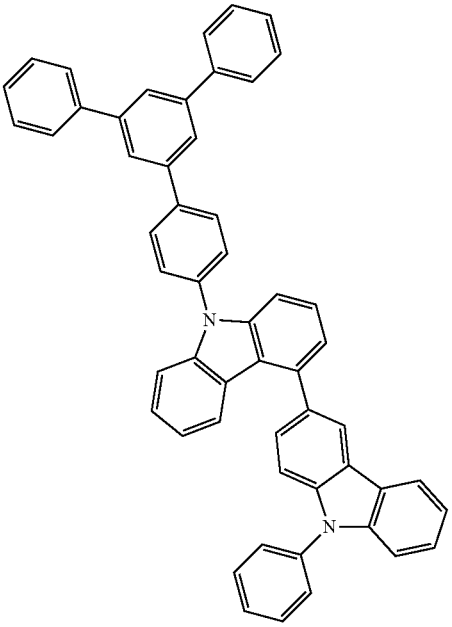
[E-128]
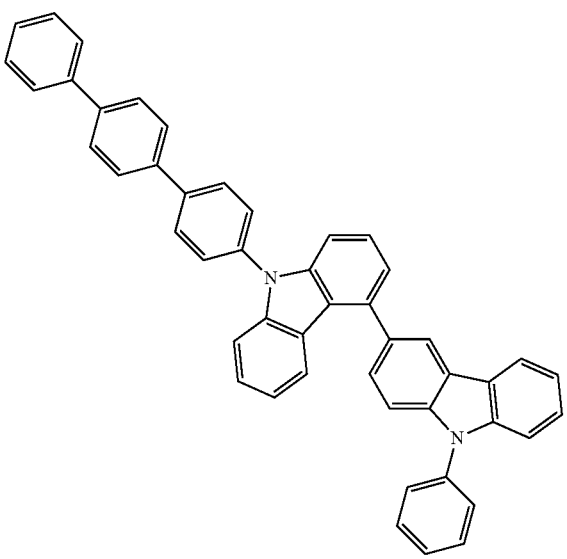

[E-129]
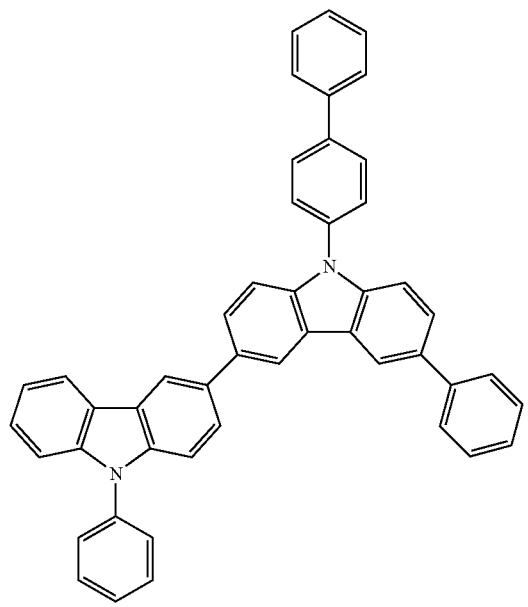
[E-130]
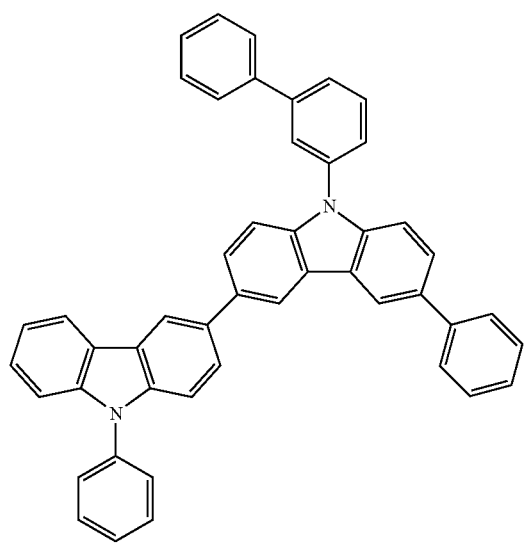
[E-131]
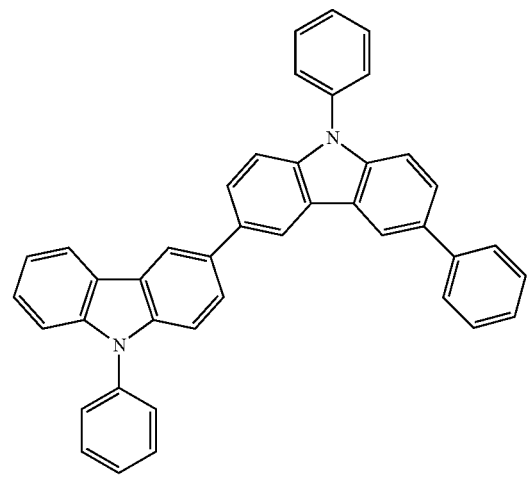
[E-132]
[E-133]
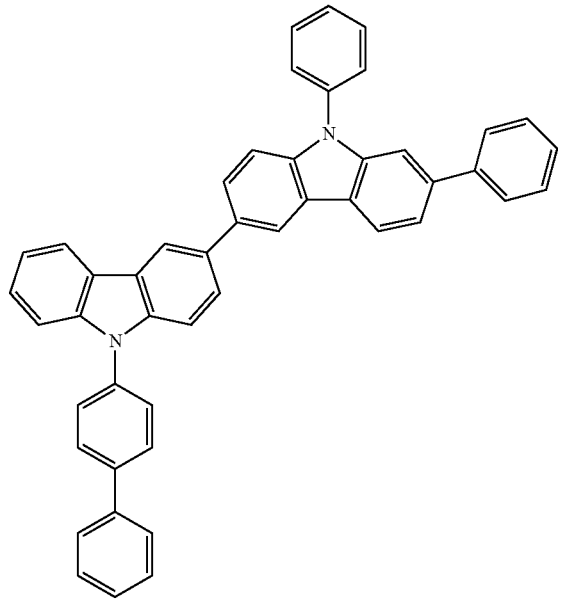

[E-134]
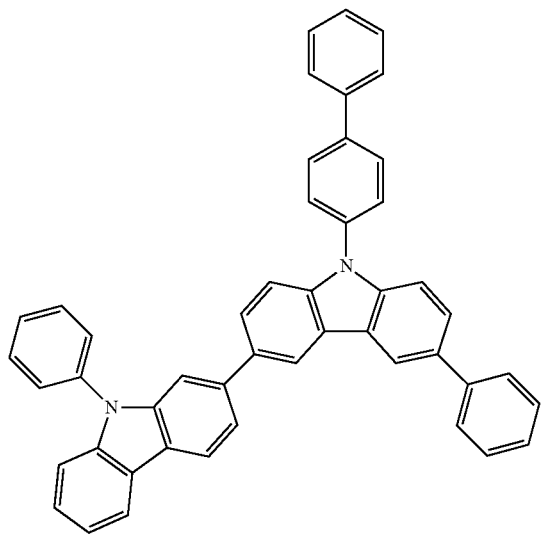

[E-135]
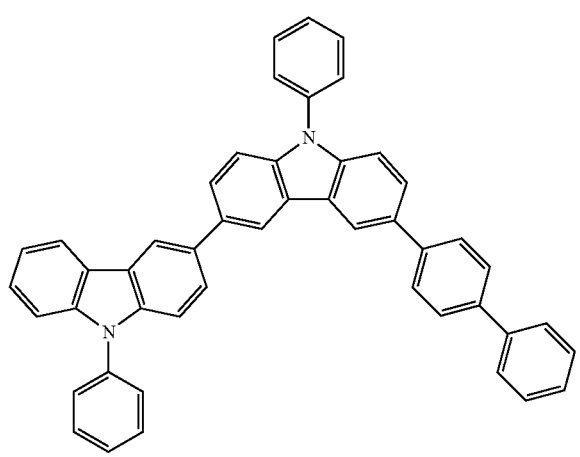

[E-136]
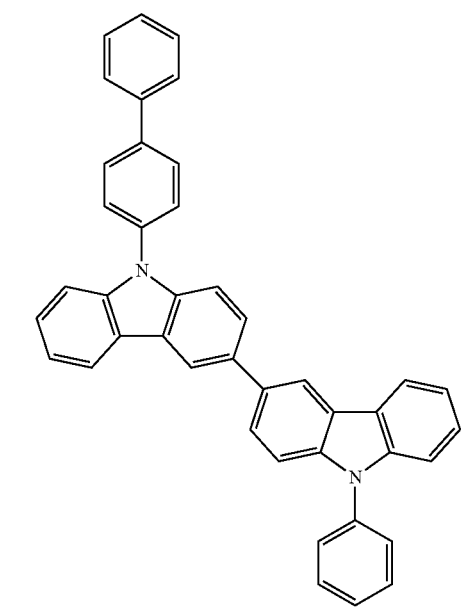

[E-137]
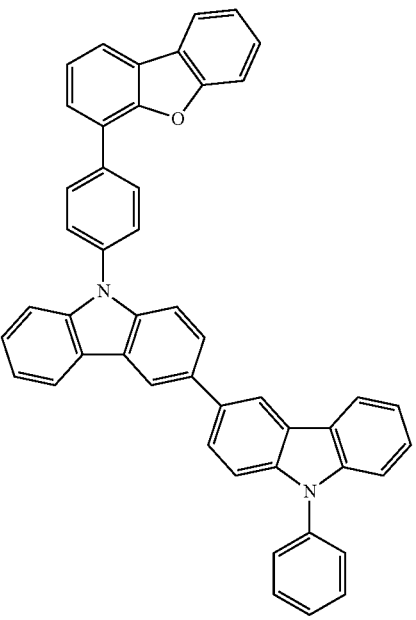

[E-138]
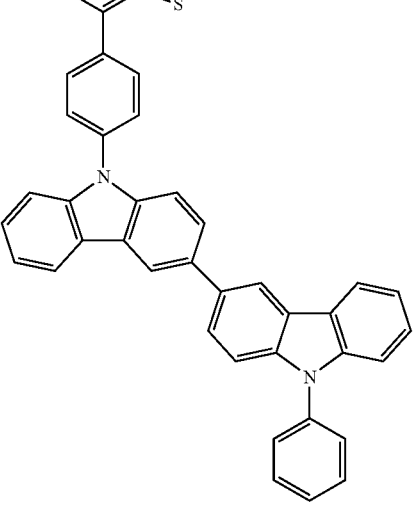

The first host compound and the second host compound may variously be combined to prepare various compositions.

A composition according to an example embodiment of the present disclosure may include a compound represented by Chemical Formula 1-I, Chemical Formula 1 II, or Chemical Formula 1-V as a first host and a compound represented by Chemical Formula C-8 or Chemical Formula C-17 of Group II as a second host.

A composition according to an example embodiment of the present disclosure may include a compound represented by Chemical Formula 1-Ia, Chemical Formula 1-II a, or Chemical Formula 1-Va as a first host and a compound represented by Chemical Formula C-8 or Chemical Formula C-17 of Group II as a second host, and *—Y$^1$-A$^1$ and *—Y$^2$-A$^2$ of Chemical Formula 2 may be selected from B-1, B-2, B-3, B-18, and B-25 of Group III.

The second compound for an organic optoelectronic device is used with the first compound for an organic optoelectronic device in the light emitting layer and increases charge mobility and stability, and thereby luminous efficiency and life-span characteristics may be improved. In addition, a ratio of the second compound for an organic optoelectronic device and the first compound for an organic optoelectronic device may be adjusted and thereby charge mobility may be controlled.

A combination ratio of the compounds, the first compound for an organic optoelectronic device and the second compound for an organic optoelectronic device in the composition of the present disclosure may be for example a weight ratio of about 1:9 to about 9:1, and specifically about 1:9 to about 8:2, about 1:9 to about 7:3, about 1:9 to about 6:4, or about 1:9 to about 5:5, and about 2:8 to about 8:2, about 2:8 to about 7:3, about 2:8 to about 6:4, or about 2:8 to about 5:5.

In addition, the first compound for an organic optoelectronic device and the second compound for an organic optoelectronic device may be included in a weight ratio of about 1:9 to about 5:5, about 2:8 to about 5:5, or about 3:7 to about 5:5. For example, the first compound for an organic optoelectronic device and the second compound for an organic optoelectronic device may be included in a weight ratio of about 5:5 or about 3:7. Within the ranges, efficiency and life-span may be simultaneously improved.

The composition may further include one or more organic compounds in addition to the first compound for an organic optoelectronic device and the second compound for an organic optoelectronic device.

The compound for an organic optoelectronic device may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$L_2MX$ [Chemical Formula Z]

In Chemical Formula Z, M is a metal, and L and X are the same or different and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

Hereinafter, an organic optoelectronic device including the compound for an organic optoelectronic device or the composition for an organic optoelectronic device is described.

An organic optoelectronic device according to another embodiment includes an anode and a cathode facing each other and at least one organic layer disposed between the anode and the cathode, wherein the organic layer includes the compound for an organic optoelectronic device or the composition for an organic optoelectronic device.

For example, the organic layer may include a light emitting layer and the light emitting layer may include the compound for an organic optoelectronic device or the composition for an organic optoelectronic device of the present disclosure.

Specifically, the compound for an organic optoelectronic device or the composition for an organic optoelectronic device may be included as a host, for example a green host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectronic device or the composition for an organic optoelectronic device.

The organic optoelectronic device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic device is described referring to drawings.

FIGS. 1 and 2 are cross-sectional views of an organic light emitting diode according to an embodiment.

Referring to FIG. 1, an organic optoelectronic diode 100 according to an embodiment includes an anode 120 and a cathode 110 and an organic layer 105 disposed between the anode 120 and the cathode 110.

The anode 120 may be made of a conductor having a large work function to help hole injection and may be for example made of a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes a light emitting layer 130 including the compound for an organic optoelectronic device.

FIG. 2 is a cross-sectional view showing an organic light emitting diode according to another embodiment.

Referring to FIG. 2, an organic light emitting diode 200 further include a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic device of the present disclosure may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there in no particular comment or were synthesized by known methods.

Preparation of Compound for Organic Optoelectronic Device

The compound as one specific examples of the present disclosure was synthesized through the following steps.

Synthesis of First Compound for Organic Optoelectronic Device

[Representative Synthesis Method]

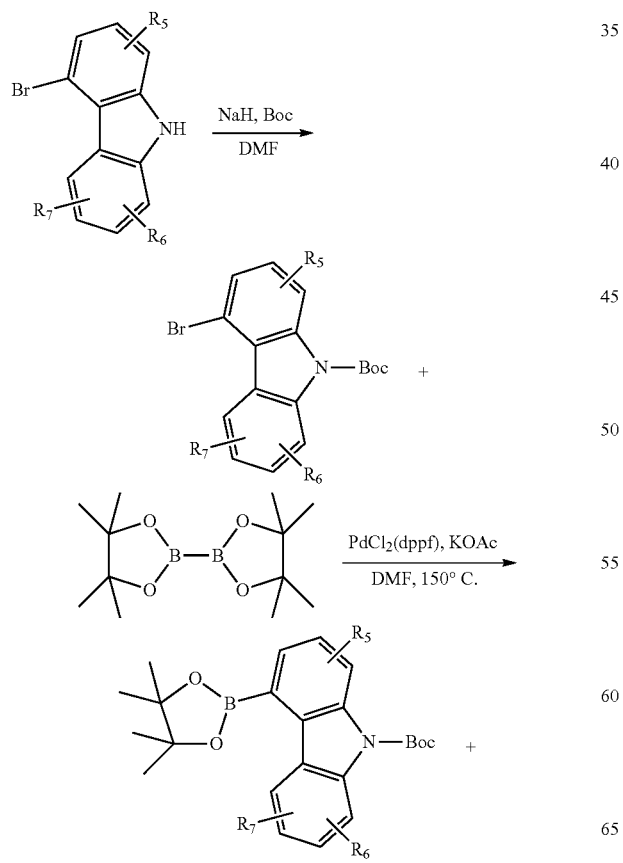
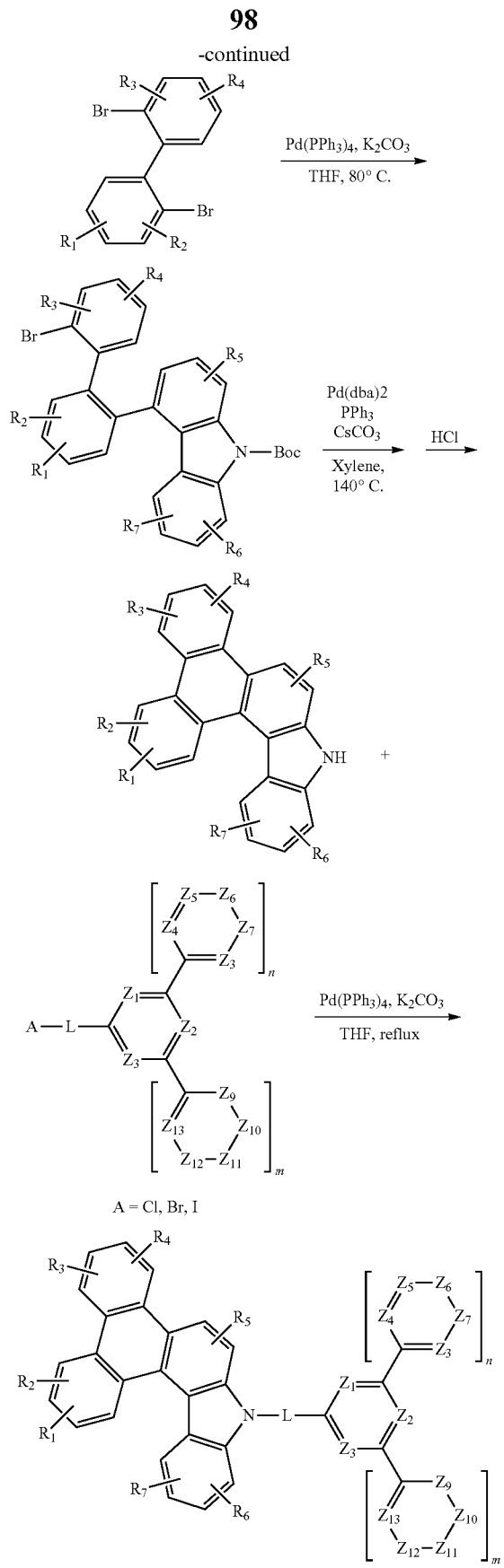

Synthesis Example 1: Synthesis of Intermediate I-1

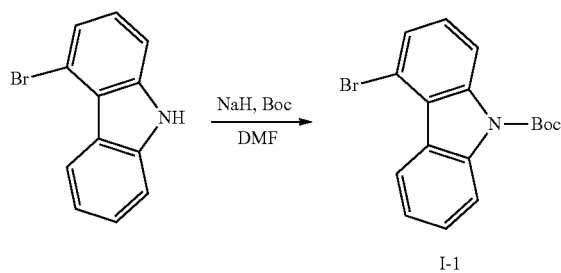

I-1

4-bromo-9H-carbazole (100 g, 406 mmol) purchased from P&H Tech Co., Ltd. (http://www.phtech.co.kr/) was dissolved in 0.5 L of dimethylformamide (DMF) under a nitrogen environment, sodium hydride (19.5 g, 813 mmol) was added thereto at 0° C., and the mixture was stirred. After 2 hours, di-tert-butyl-dicarbonate (133 g, 609 mmol) was added thereto, and the obtained mixture was stirred for 1 hour. When a reaction was complete, water was added thereto at 0° C., and an extract was obtained by using dichloromethane (DCM), treated with anhydrous magnesium sulfate to remove moisture, and then, filtered and concentrated under a reduced pressure. The obtained residue was separated and purified through flash column chromatography to obtain Intermediate I-1 (137.8 g, 98%).

HRMS (70 eV, EI+): m/z calcd for C17H16BrNO2: 345.0364, found: 345.

Elemental Analysis: C, 59%; H, 5%

Synthesis Example 2: Synthesis of Intermediate I-2

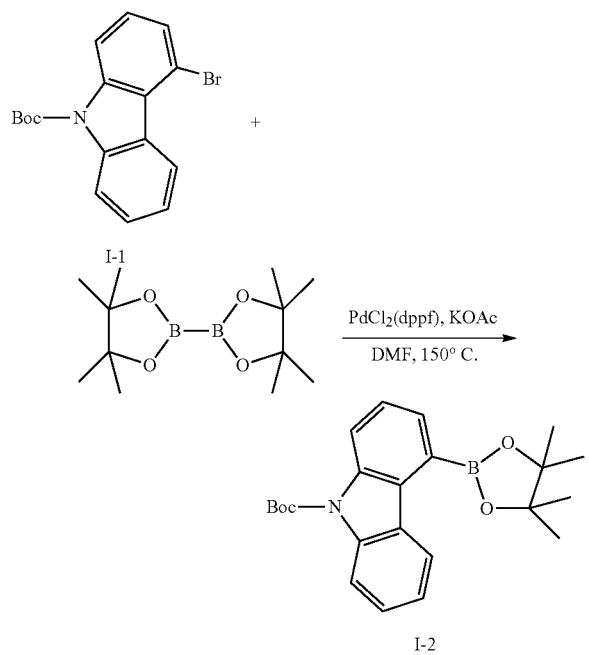

I-2

Intermediate I-1 (138 g, 398 mmol) was dissolved in 1.0 L of dimethylformamide (DMF) under a nitrogen environment, bis(pinacolato)diboron (121 g, 478 mmol) and (1,1'-bis(diphenylphosphine)ferrocene) dichloropalladium (II) (6.50 g, 7.96 mmol), and potassium acetate (117 g, 1194 mmol) were added thereto, and the mixture was heated and refluxed at 150° C. for 4 hours. When a reaction was complete, water was added thereto, and the obtained mixture was filtered and then, dried in a vacuum oven. A residue obtained therefrom was separated and purified through flash column chromatography to obtain Intermediate I-2 (88.1 g, 56%).

HRMS (70 eV, EI+): m/z calcd for C23H28BNO4: 393.2111, found: 393.

Elemental Analysis: C, 70%; H, 7%

Synthesis Example 3: Synthesis of Intermediate I-3

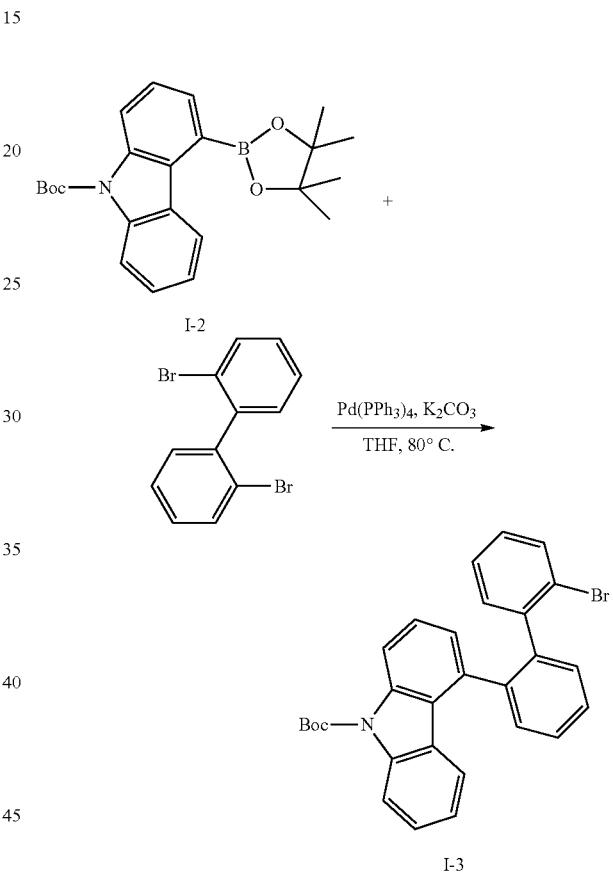

I-3

Intermediate I-2 (68 g, 173 mmol) was dissolved in 0.7 L of tetrahydrofuran (THF) under a nitrogen environment, 2,2'-dibromobiphenyl (80.9 g, 259 mmol) purchased from Mascot (Asia) Company Limited and tetrakis(triphenylphosphine)palladium (2.0 g, 1.73 mmol) were added thereto, and the obtained mixture was stirred. Potassium carbonate (59.7 g, 432 mmol) saturated in water was added thereto, and the obtained mixture was heated and refluxed at 80° C. for 12 hours. When a reaction was complete, water was added thereto, and an extract was obtained by using dichloromethane (DCM), treated with anhydrous magnesium sulfate to remove moisture, and then, filtered and concentrated under a reduced pressure. A residue obtained therefrom was separated and purified through flash column chromatography to obtain Intermediate I-3 (10.8 g, 13%).

HRMS (70 eV, EI+): m/z calcd for C29H24BrNO2: 497.0990, found: 497.

Elemental Analysis: C, 70%; H, 5%

Synthesis Example 4: Synthesis of Intermediate I-4

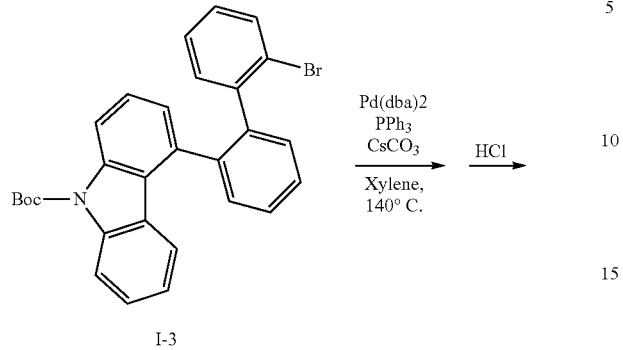

I-3

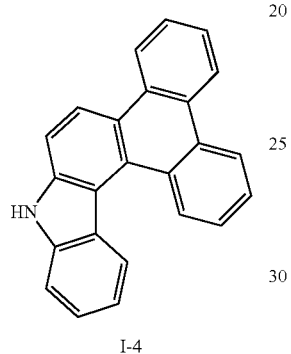

I-4

Intermediate I-3 (10.8 g, 21.6 mmol) was dissolved in 0.1 L of xylene under a nitrogen environment, bis(dibenzylideneacetone)palladium (0) (0.62 g, 1.08 mmol), triphenylphosphine (1.13 g, 4.33 mmol), and cesium carbonate (8.46 g, 26.0 mmol) were added thereto, and the mixture was heated and refluxed at 140° C. for 24 hours. When a reaction was complete, water was added thereto, and an extract was obtained by using dichloromethane (DCM), treated with anhydrous magnesium sulfate to remove moisture, and then, filtered and concentrated under a reduced pressure. A residue obtained therefrom was separated and purified through flash column chromatography to obtain Intermediate I-4 (3.79 g, 55%).

HRMS (70 eV, EI+): m/z calcd for C24H15N: 317.1204, found: 317.

Elemental Analysis: C, 91%; H, 5%

Synthesis Example 5: Synthesis of Intermediate I-5

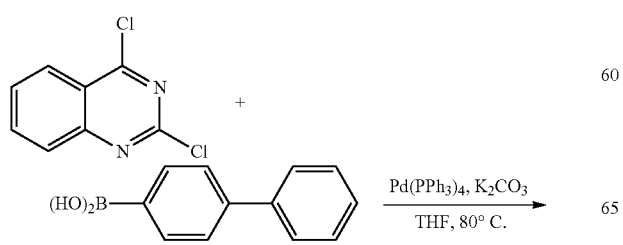

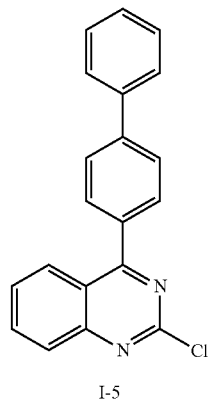

I-5

Intermediate I-5 (79.5 g, 50%) was obtained according to the same method as Synthesis Example 3 except for using 2,4-dichloroquinazoline (100 g, 502 mmol) purchased from P&H Tech Co., Ltd. (http://www.phtech.co.kr/) and biphenyl-4-boronic acid (89.5 g, 452 mmol).

HRMS (70 eV, EI+): m/z calcd for C20H13ClN2: 316.0767, found: 316.

Elemental Analysis: C, 76%; H, 4%

Synthesis Example 6: Synthesis of Intermediate I-6

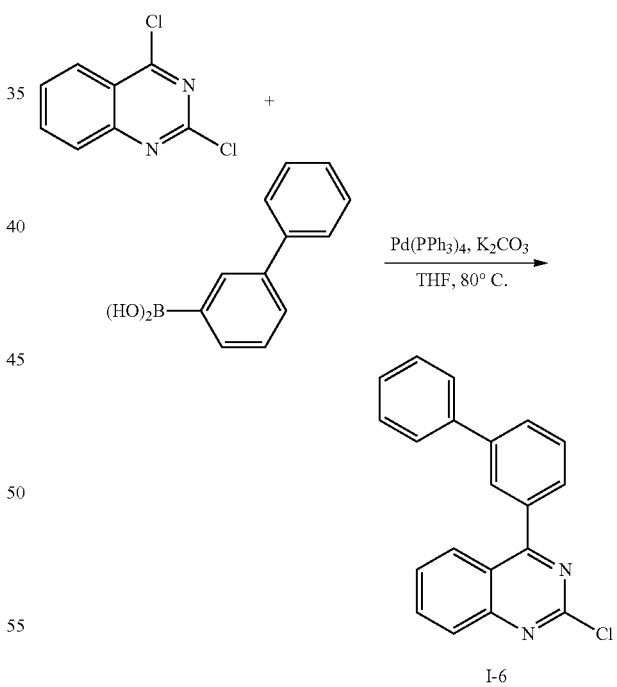

I-6

Intermediate I-6 (77.3 g, 54%) was obtained according to the same method as Synthesis Example 3 except for using 2,4-dichloroquinazoline (100 g, 502 mmol) purchased from P&H Tech Co., Ltd. (http://www.phtech.co.kr/) and biphenyl-3-boronic acid (89.5 g, 452 mmol).

HRMS (70 eV, EI+): m/z calcd for C20H13ClN2: 316.0767, found: 316.

Elemental Analysis: C, 76%; H, 4%

Synthesis Example 7: Synthesis of Compound 1

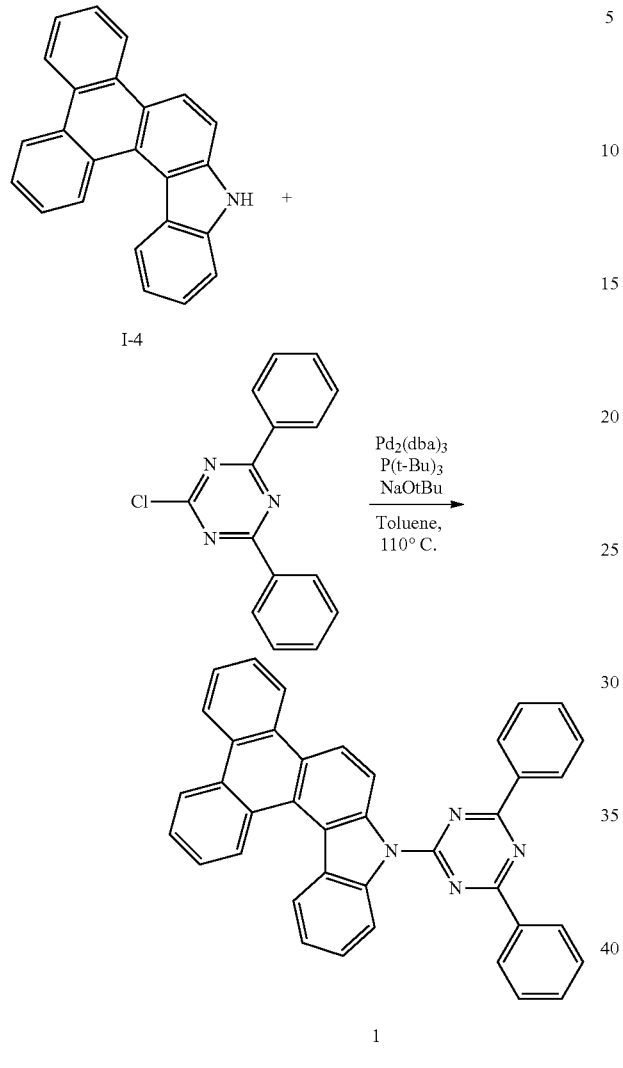

Intermediate I-4 (10 g, 31.5 mmol) was dissolved in 0.1 L of toluene under a nitrogen environment, 2-chloro-4,6-diphenyl-1,3,5-triazine (8.43 g, 31.5 mmol) purchased from Tokyo Chemical Industry, tris(diphenylideneacetone)dipalladium (0) (0.29 g, 0.32 mmol), tris-tert butylphosphine (0.32 g, 1.58 mmol), and sodium tert-butoxide (3.63 g, 37.8 mmol) were sequentially added thereto, and the mixture was heated and refluxed at 110° C. for 15 hours. When a reaction was complete, water was added thereto, and an extract was obtained by using dichloromethane (DCM), treated with anhydrous magnesium sulfate to remove moisture, and then, filtered and concentrated under a reduced pressure. A residue obtained therefrom was obtained separated and purified through flash column chromatography to obtain Compound 1 (16.4 g, 95%).

HRMS (70 eV, EI+): m/z calcd for $C_{39}H_{24}N_4$: 548.2001, found: 548.

Elemental Analysis: C, 85%; H, 4%

Synthesis Example 8: Synthesis of Compound 3

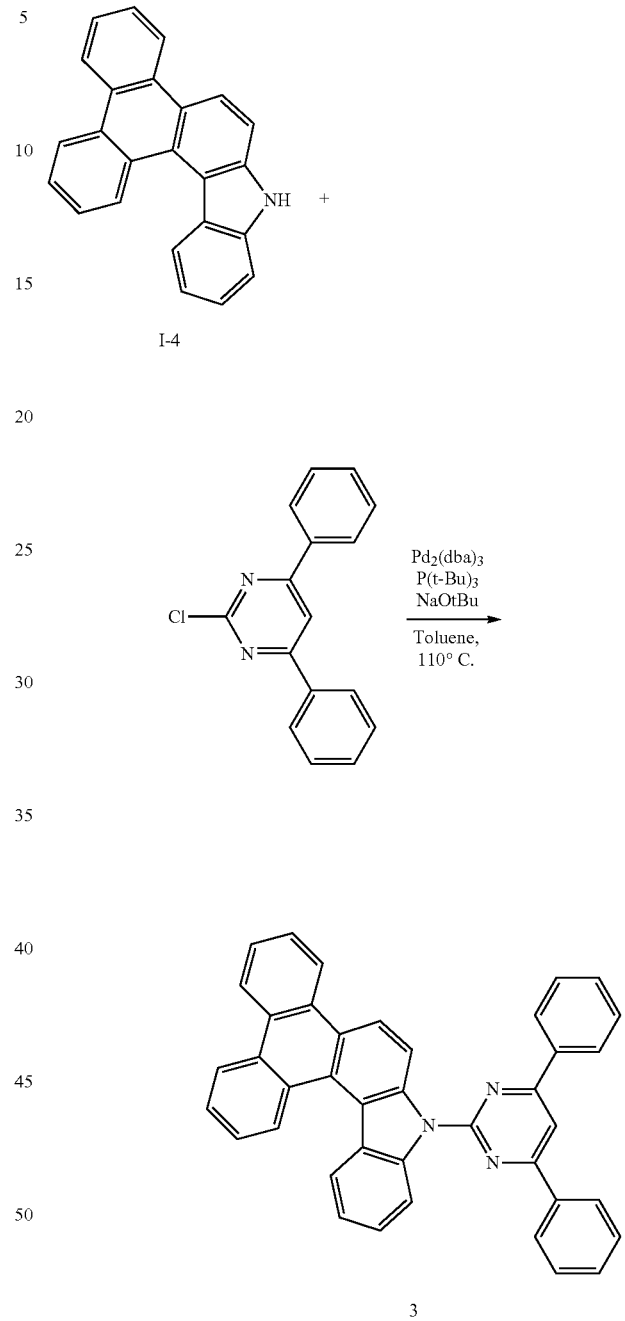

Compound 3 (15.7 g, 91%) was obtained according to the same method as Synthesis Example 7 except for using Intermediate I-4 (10 g, 31.5 mmol) and 2-chloro-4,6-diphenylpyrimidine (8.40 g, 31.5 mmol) purchased from Tokyo Chemical Industry.

HRMS (70 eV, EI+): m/z calcd for $C_{40}H_{25}N_3$: 547.2048, found: 547.

Elemental Analysis: C, 88%; H, 5%

Synthesis Example 9: Synthesis of Compound 5

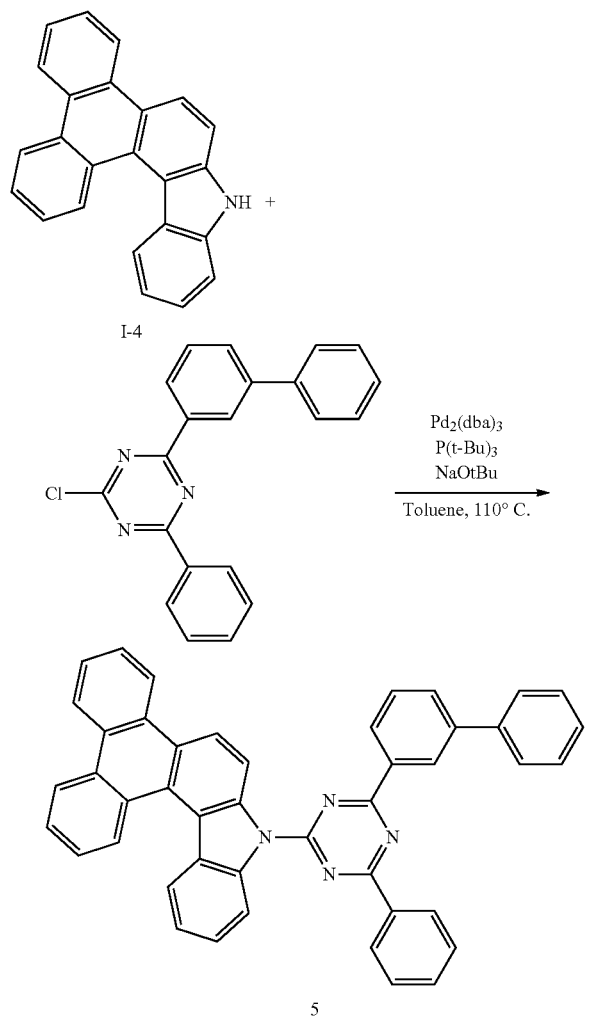

Compound 5 (17.5 g, 89%) was obtained according to the same method as Synthesis Example 7 except for using Intermediate I-4 (10 g, 31.5 mmol) and 2-(biphenyl-3-yl)-4-chloro-6-phenyl-1,3,5-triazine (10.8 g, 31.5 mmol) purchased from Richest Group Limited (http://www.richestgroup.com/).

HRMS (70 eV, EI+): m/z calcd for $C_{45}H_{28}N_4$: 624.2314, found: 624.

Elemental Analysis: C, 87%; H, 5%

Synthesis Example 10: Synthesis of Compound 6

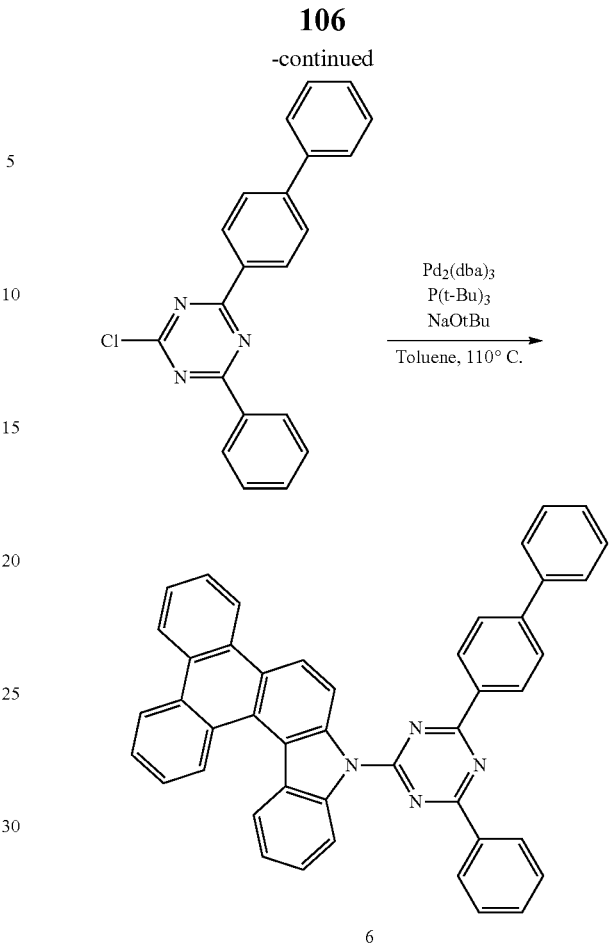

Compound 6 (17.7 g, 90%) was obtained according to the same method as Synthesis Example 7 except for using Intermediate I-4 (10 g, 31.5 mmol) and 2-(biphenyl-4-yl)-4-chloro-6-phenyl-1,3,5-triazine (10.8 g, 31.5 mmol) purchased from Richest Group Limited (http://www.richestgroup.com/).

HRMS (70 eV, EI+): m/z calcd for $C_{45}H_{28}N_4$: 624.2314, found: 624.

Elemental Analysis: C, 87%; H, 5%

Synthesis Example 11: Synthesis of Compound 13

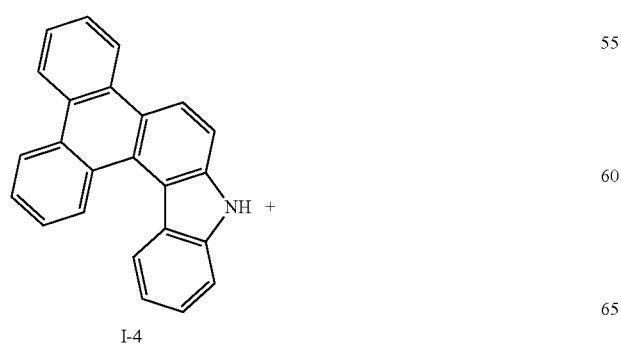

-continued

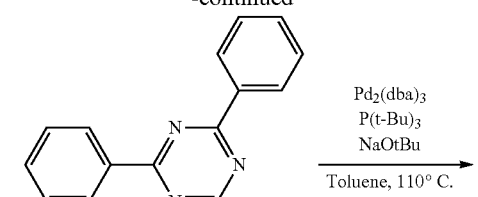

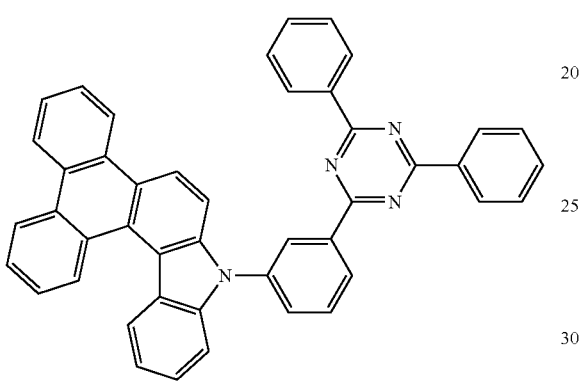

13

-continued

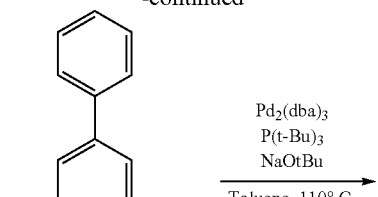

I-5

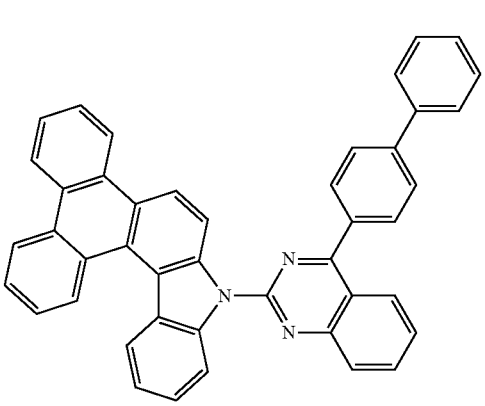

30

Compound 13 (18.9 g, 96%) was obtained according to the same method as Synthesis Example 7 except for using Intermediate I-4 (10 g, 31.5 mmol) and 2-(3-bromophenyl)-4,6-diphenyl-1,3,5-triazine (12.2 g, 31.5 mmol) purchased from Richest Group Limited (http://www.richest-group.com/).

HRMS (70 eV, EI+): m/z calcd for C45H28N4: 624.2314, found: 624.

Elemental Analysis: C, 87%; H, 5%

Synthesis Example 12: Synthesis of Compound 30

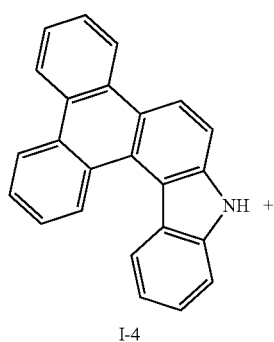

I-4

Compound 30 (16.9 g, 90%) was obtained according to the same method as Synthesis Example 7 except for using Intermediate I-4 (10 g, 31.5 mmol) and Intermediate I-5 (9.8 g, 31.5 mmol).

HRMS (70 eV, EI+): m/z calcd for C44H27N3: 597.2205, found: 597.

Elemental Analysis: C, 88%; H, 5%

Synthesis Example 13: Synthesis of Compound 31

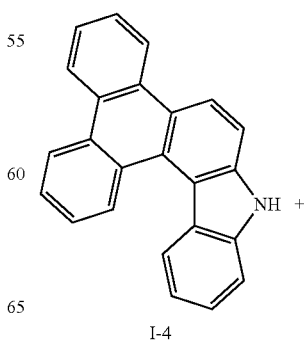

I-4

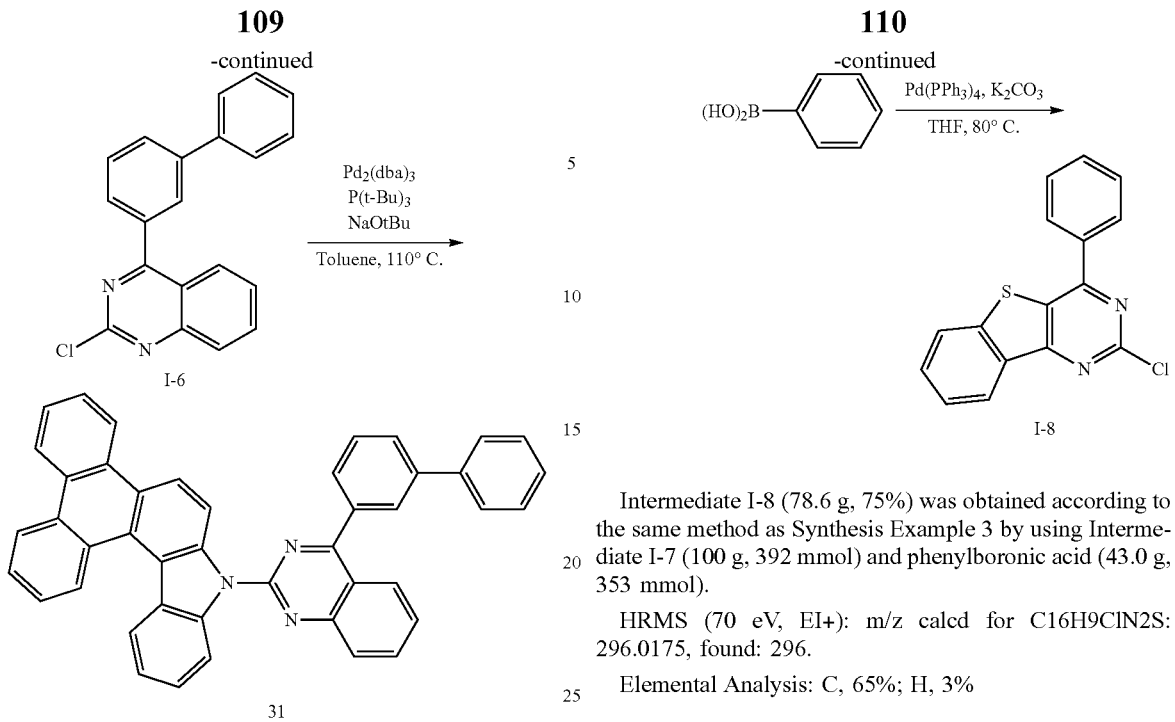

Compound 31 (17.3 g, 92%) was obtained according to the same method as Synthesis Example 7 except for using Intermediate I-4 (10 g, 31.5 mmol) and Intermediate I-6 (9.8 g, 31.5 mmol).

HRMS (70 eV, EI+): m/z calcd for C44H27N3: 597.2205, found: 597.

Elemental Analysis: C, 88%; H, 5%

Synthesis Example 14: Synthesis of Intermediate I-7

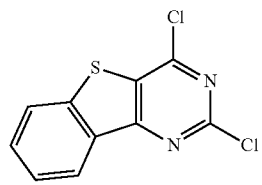

Intermediate I-7 was synthesized with a reference to a synthesis method of Patent Laid Open KR 10-2015-0083786.

HRMS (70 eV, EI+): m/z calcd for C10H4Cl2N2S: 253.9472, found: 254.

Elemental Analysis: C, 47%; H, 2%

Synthesis Example 15: Synthesis of Intermediate I-8

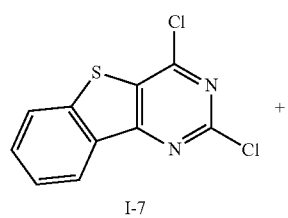

Intermediate I-8 (78.6 g, 75%) was obtained according to the same method as Synthesis Example 3 by using Intermediate I-7 (100 g, 392 mmol) and phenylboronic acid (43.0 g, 353 mmol).

HRMS (70 eV, EI+): m/z calcd for C16H9ClN2S: 296.0175, found: 296.

Elemental Analysis: C, 65%; H, 3%

Synthesis Example 16: Synthesis of Intermediate I-9

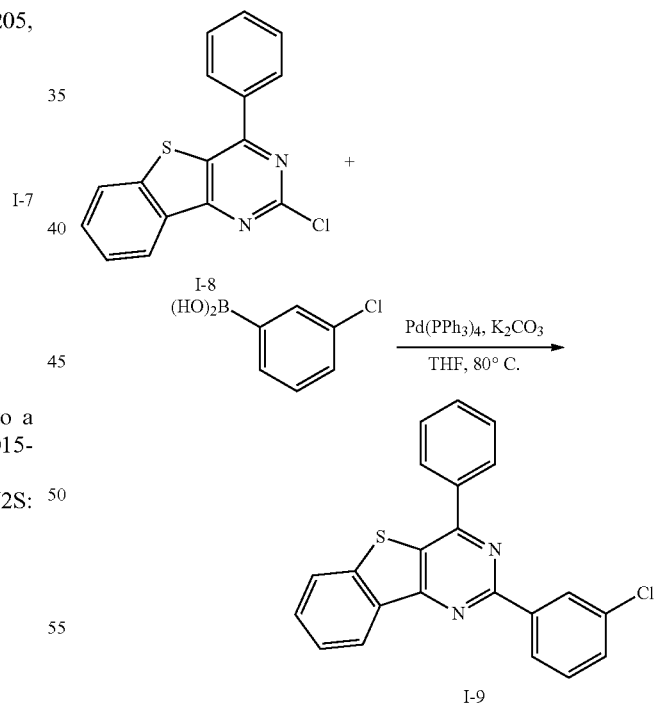

Intermediate I-9 (55.1 g, 88%) was obtained according to the same method as Synthesis Example 3 except for using Intermediate I-8 (50 g, 168 mmol) and 3-chlorophenylboronic acid (29.0 g, 185 mmol).

HRMS (70 eV, EI+): m/z calcd for C22H13ClN2S: 372.0488, found: 372.

Elemental Analysis: C, 71%; H, 4%

Synthesis Example 17: Synthesis of Compound 56

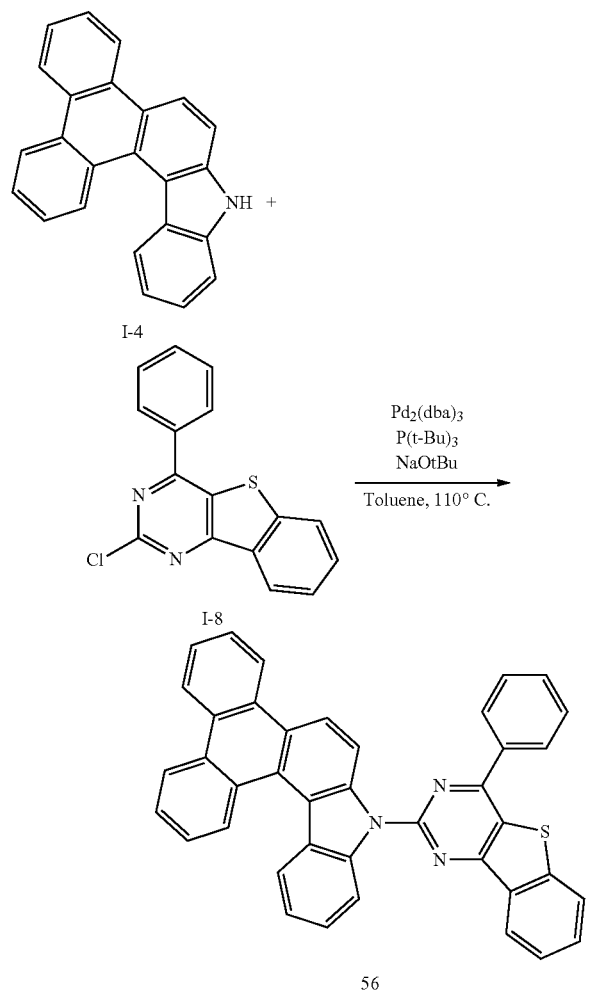

Compound 56 (17.3 g, 95%) was obtained according to the same method as Synthesis Example 7 except for using Intermediate I-4 (10 g, 31.5 mmol) and Intermediate I-8 (9.35 g, 31.5 mmol).

HRMS (70 eV, EI+): m/z calcd for C40H23N3S: 577.1613, found: 577.

Elemental Analysis: C, 83%; H, 4%

Synthesis Example 18: Synthesis of Compound 60

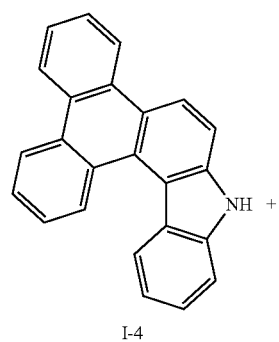

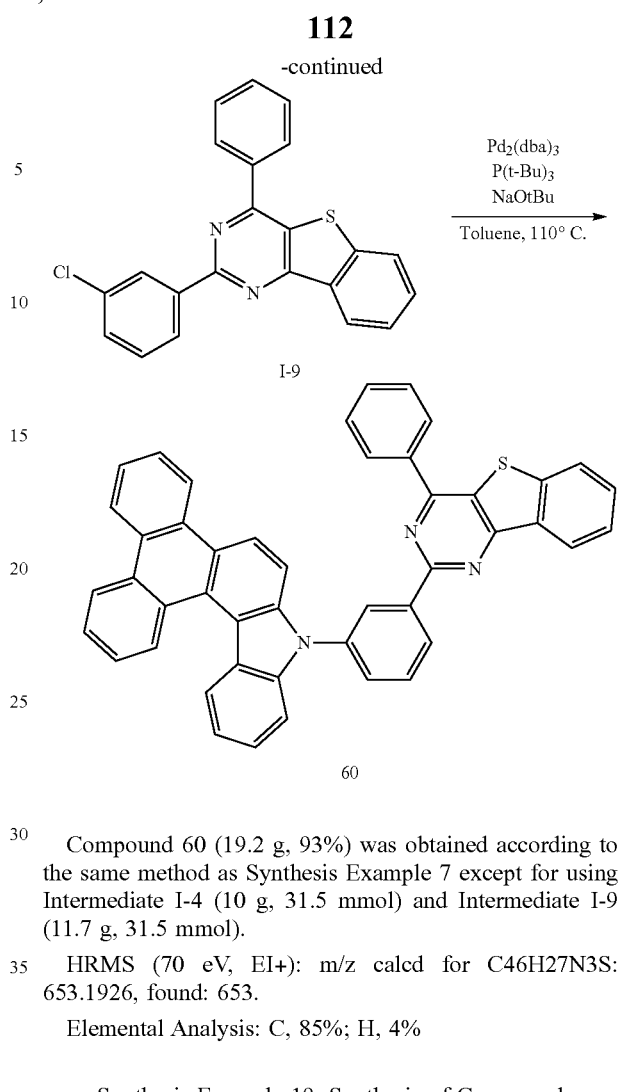

Compound 60 (19.2 g, 93%) was obtained according to the same method as Synthesis Example 7 except for using Intermediate I-4 (10 g, 31.5 mmol) and Intermediate I-9 (11.7 g, 31.5 mmol).

HRMS (70 eV, EI+): m/z calcd for C46H27N3S: 653.1926, found: 653.

Elemental Analysis: C, 85%; H, 4%

Synthesis Example 19: Synthesis of Compound Host 1

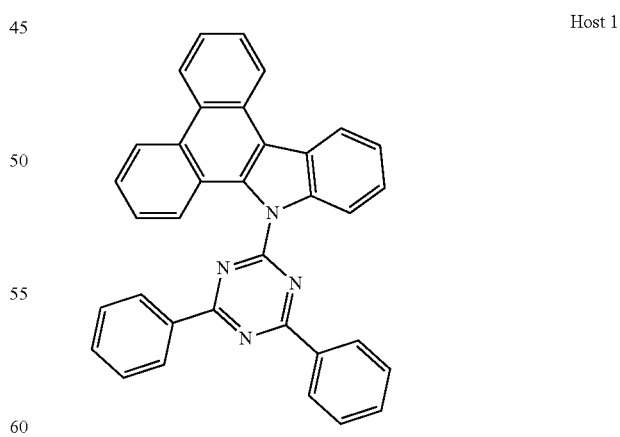

Compound Host 1 was synthesized with a reference to a synthesis method of Patent KR 10-1219481.

HRMS (70 eV, EI+): m/z calcd for C35H22N4: 498.1844, found: 498.

Elemental Analysis: C, 84%; H, 4%

Synthesis Example 20: Synthesis of Compound Host 2

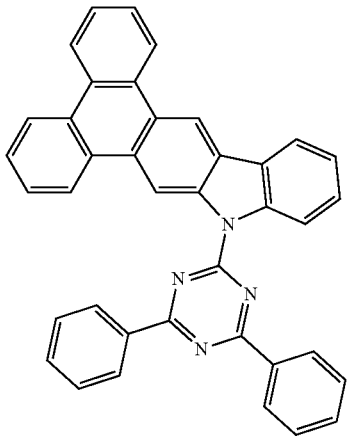
Host 2

Compound Host 2 was synthesized with a reference to a synthesis method of Patent KR 2012-0072784.

HRMS (70 eV, EI+): m/z calcd for $C_{39}H_{24}N_4$: 548.2001, found: 548.

Elemental Analysis: C, 85%; H, 4%

Synthesis Example 21: Synthesis of Compound Host 3

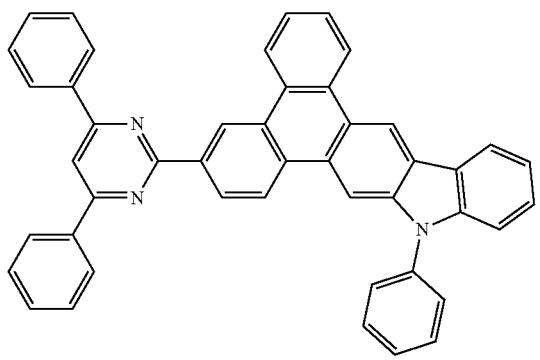
Host 3

Compound Host 3 was synthesized with a reference to a synthesis method of Patent KR 10-119693.

HRMS (70 eV, EI+): m/z calcd for $C_{46}H_{29}N_3$: 623.2361, found: 623.

Elemental Analysis: C, 89%; H, 5%

Manufacture of Organic Light Emitting Diode (Green)

Example 1

An organic light emitting diode was manufactured by using Compound 1 according to Synthesis Example 7 as a host and $Ir(PPy)_3$ as a dopant.

A 1000 Å-thick ITO was used as an anode and a 1000 Å-thick aluminum (Al) as a cathode. Specifically, the organic light emitting diode was manufactured in a method of cutting an ITO glass substrate having sheet resistance of 15 $\Omega/cm^2$ into a size of 50 mm×50 mm×0.7 mm, ultrasonic wave-cleaning it in acetone, isopropyl alcohol, and pure water respectively for 15 minutes and UV ozone-cleaning it for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of $650 \times 10^{-7}$ Pa at a deposition rate of 0.1 to 0.3 nm/s. Subsequently, a 300 Å-thick film as a light emitting layer was formed by using the compound 1 according to Synthesis Example 7 under the same vacuum deposition condition as above, and $Ir(PPy)_3$ as a phosphorescent dopant was simultaneously deposited. Herein, the phosphorescent dopant was deposited in an amount of 7 wt % based on 100 wt % of the total amount of the light emitting layer by adjusting the deposition rate.

On the light emitting layer, a 50 Å-thick film as a hole blocking layer was formed by depositing bis(2-methyl-8-quinolinolate)-4-(phenylphenolato)aluminum (BAlq) under the same vacuum deposition condition as above. Subsequently, a 200 Å-thick film as an electron transport layer was formed by depositing Alq3 under the same vacuum deposition condition as above. On the electron transport layer, LiF and Al were sequentially deposited as a cathode, manufacturing the organic light emitting diode.

A structure of the organic light emitting diode was ITO/NPB (80 nm)/EML (Compound 1 (93 wt %)+$Ir(PPy)_3$ (7 wt %), 30 nm)/BAlq (5 nm)/$Alq_3$ (20 nm)/LiF (1 nm)/Al (100 nm).

Examples 2 to 7

Each organic light emitting diode of Examples 2 to 7 was manufactured according to the same method as Example 1 by using the hosts as shown in Table 1.

Comparative Examples 1 to 4

An organic light emitting diode of Comparative Example 1 was manufactured according to the same method as Example 1 by using 4,4'-di(9-carbazol-9-yl)biphenyl (CBP) instead of Compound 1 of Synthesis Example 7 and each organic light emitting diode of Comparative Examples 2 to 4 was manufactured according to the same method as Example 1 by using the hosts as shown in Table 1.

Evaluation

Current density change, luminance change, and luminous efficiency of each organic light emitting diode according to Examples 1 to 7 and Comparative Examples 1 to 4 were measured.

Specific measurement methods are as follows, and the results are shown in Table 1.

(1) Measurement of Current Density Change Depending on Voltage Change

Current values flowing in the unit device of the obtained organic light emitting diodes were measured, while increasing the voltage from 0 V to 10 V using a current-voltage meter (Keithley 2400), and the measured current values were divided by areas to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-span

The results were obtained by measuring a time when current efficiency (cd/A) was decreased down to 90%, while luminance (cd/m$^2$) was maintained to be 5000 cd/m$^2$.

(5) Measurement of Driving Voltage

A driving voltage of each diode was measured using a current-voltage meter (Keithley 2400) at 15 mA/cm$^2$.

TABLE 1

| Nos. | Compounds | Driving voltage (V) | Color (EL color) | Efficiency (cd/A) | 90% life-span (h) at 5000 cd/m$^2$ |
| --- | --- | --- | --- | --- | --- |
| Example 1 | 1 | 3.86 | Green | 58.1 | 1,250 |
| Example 2 | 3 | 4.01 | Green | 63.5 | 800 |
| Example 3 | 5 | 3.90 | Green | 59.3 | 1,560 |
| Example 4 | 6 | 3.88 | Green | 60.2 | 1,490 |
| Example 5 | 13 | 3.75 | Green | 61.8 | 1,750 |
| Example 6 | 56 | 3.95 | Green | 57.9 | 1,200 |
| Example 7 | 60 | 4.00 | Green | 59.0 | 1,450 |
| Comparative Example 1 | CBP | 4.81 | Green | 31.4 | 40 |
| Comparative Example 2 | Host 1 | 4.52 | Green | 40.5 | 100 |
| Comparative Example 3 | Host 2 | 4.25 | Green | 45.8 | 550 |
| Comparative Example 4 | Host 3 | 4.77 | Green | 45.0 | 50 |

According to the results of Table 1, diodes of Example 1 to Example 7 may realize a low driving voltage, high efficiency, and long life-span compared with those of Comparative Example 1 to Comparative Example 4.

(Energy Level System Using Gaussian Tool)

An energy level of each material was calculated by a B3LYP/6-31G** method using program Gaussian 09 with Super Computer GAIA (IBM power 6), and the results are shown in Table 2 and Table 3.

TABLE 2

| types | HOMO (eV) | LUMO (eV) | ΔE S1 | ΔE T1 |
| --- | --- | --- | --- | --- |
| A type | −5.354 | −1.173 | 3.537 | 2.652 |
| B type | −5.199 | −1.185 | 3.445 | 2.641 |
| C type | −5.197 | −1.167 | 3.457 | 2.652 |

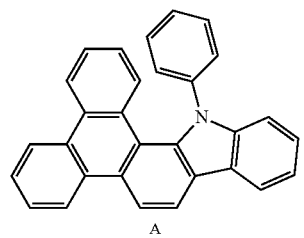

A

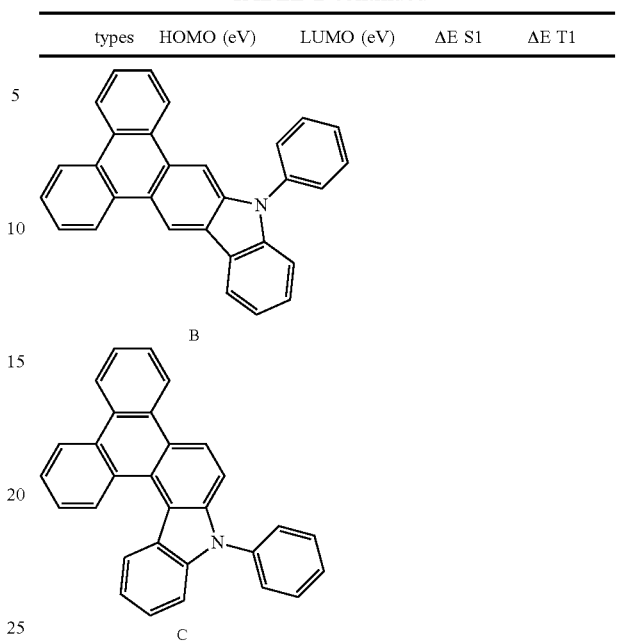

B

C

Triphenylene and carbazole may be fused into the above three type structures. Among these structures, a C type has the most shallow HOMO and thus may be the most advantageous for a hole flow. In addition, an A type and the C type are more bended and thus have higher T1 than a B type and resultantly, may realize high efficiency in a phosphorescence green device. This fact is ensured from the device results of Table 1.

TABLE 3

| Compounds | HOMO (eV) | LUMO (eV) |
| --- | --- | --- |
| 1 | −5.484 | −1.972 |
| 5 | −5.482 | −1.978 |
| 13 | −5.212 | −2.025 |
| Host 2 | −5.520 | −1.959 |

Comparing energy levels of Compounds 1, 5, and 13 in which C type fused triphenylene and triazine are linked and Compound Host 2 in which B type fused triphenylene and triazine are linked, Compounds 1, 5, and 13 have shallow HOMO but deep LUMO, and thus organic light emitting diodes respectively including Compounds 1, 5, and 13 may be expected to have a low driving voltage and high efficiency compared with an organic light emitting diode including Compound Host 2, as shown in Table 1.

Manufacture of Organic Light Emitting Diode (Red)

Example 8

An organic light emitting diode was manufactured by using Compound 30 according to Synthesis Example 12 as a host and acetylacetonato bis(2-phenylquinolinato)iridium (Ir(pq)$_2$acac) as a dopant.

A 1500 Å-thick ITO was used as an anode and a 1000 Å-thick aluminum (Al) as a cathode. Specifically, the organic light emitting diode was manufactured in a method of cutting an ITO glass substrate having sheet resistance of 15 Ω/cm$^2$ into a size of 50 mm×50 mm×0.7 mm, ultrasonic wave-cleaning it in acetone, isopropyl alcohol, and pure water respectively for 15 minutes and UV ozone-cleaning it for 30 minutes.

On the substrate, a 600 Å-thick hole injection layer was formed by depositing 4,4'-bis[N-[4-{N,N-bis(3-methylphenyl)amino}-phenyl]-N-phenylamino]biphenyl [DNTPD] under a vacuum degree of 650×10$^{-7}$ Pa at a deposition rate of 0.1 to 0.3 nm/s. Subsequently, a 300 Å-thick hole transport layer was formed by depositing HT-1 (N-(biphenyl-4-yl)-N-(4-(9-phenyl-9H-carbazol-3-yl)phenyl)biphenyl-4-amine) under the same vacuum deposition condition. Then, a 300 Å-thick light emitting layer was formed by using Compound 30 according to Synthesis Example 12 under the same vacuum deposition condition as above, wherein a phosphorescent dopant, acetylacetonato bis(2-phenylquinolinato)iridium (Ir(pq)$_2$acac) was simultaneously deposited. Herein, the phosphorescent dopant was deposited in an amount of 7 wt % based on 100 wt % of the total amount of the light emitting layer by adjusting a deposition rate.

On the light emitting layer, a 50 Å-thick hole blocking layer was formed by depositing bis(2-methyl-8-quinolinolate)-4-(phenylphenolato)aluminum (BAlq) under the same vacuum deposition condition as above. Subsequently, a 250 Å-thick electron transport layer was formed by depositing tris(8-hydroxyquinolinato)aluminum (Alq$_3$) under the same vacuum deposition condition as above. On the electron transport layer, LiF and Al were sequentially deposited as a cathode, manufacturing the organic photoelectric device.

A structure of the organic light emitting diode was ITO/DNTPD (60 nm)/HT-1 (30 nm)/EML (Compound 30 (93 wt %)+Ir(pq)$_2$acac (7 wt %), 30 nm)/Balq (5 nm)/Alq$_3$ (25 nm)/LiF (1 nm)/Al (100 nm).

Example 9

An organic light emitting diode was manufactured according to the same method as Example 8 except for using Compound 31 of Synthesis Example 13 instead of Compound 30 of Synthesis Example 12.

Comparative Example 5

An organic light emitting diode was manufactured according to the same method as Example 8 except for using 4,4'-di(9-carbazol-9-yl)biphenyl (CBP) instead of Compound 30 of Synthesis Example 12.
Evaluation Current density changes, luminance changes, and luminous efficiency depending on a voltage of each organic light emitting diode according to Examples 8, 9, and Comparative Example 5 were measured.

Specific measurement methods are as follows, and the results are shown in Table 4.

(1) Measurement of Current Density Change Depending on Voltage Change

Current values flowing in the unit device of the obtained organic light emitting diodes were measured, while increasing the voltage from 0 V to 10 V using a current-voltage meter (Keithley 2400), and the measured current values were divided by areas to provide the results.

(2) Measurement of Luminance Change Depending on Voltage Change Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm2) were calculated by using the luminance, current density, and voltages (V) from the items (1) and (2).

(4) Measurement of Driving Voltage

A driving voltage of each diode was measured using a current-voltage meter (Keithley 2400) at 15 mA/cm$^2$.

TABLE 4

| Nos. | Compounds | Driving voltage (V) | Color (EL color) | Luminous efficiency (cd/A) |
|---|---|---|---|---|
| Example 8 | 30 | 4.38 | Red | 42.8 |
| Example 9 | 31 | 4.40 | Red | 45.1 |
| Comparative Example 5 | CBP | 7.4 | Red | 37.2 |

Referring to Table 4, the organic light emitting diodes according to Examples 8 and 9 exhibited remarkably improved luminous efficiency and driving voltage characteristics compared with the organic light emitting diode according to Comparative Example 5.

(Synthesis of Second Compound for Organic Optoelectronic Device)

Synthesis Example 22: Synthesis of Intermediate I-10

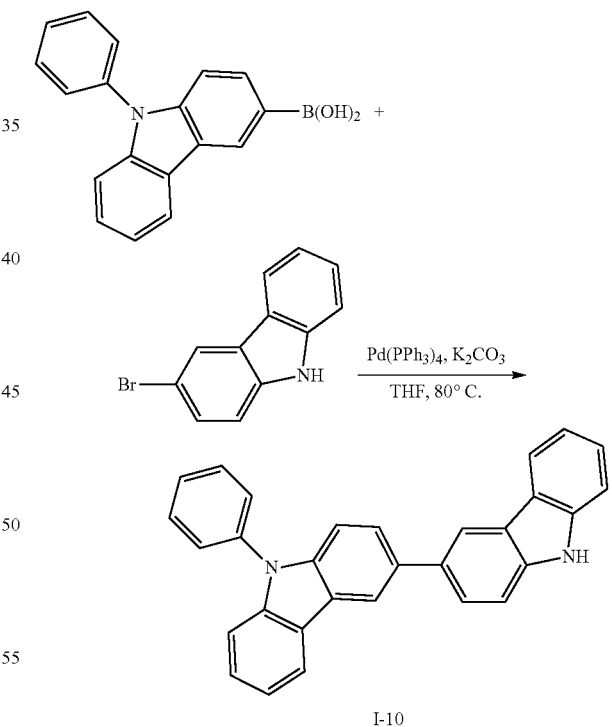

I-10

Intermediate I-10 (85.3 g, 60%) was obtained according to the same method as Synthesis Example 3 except for using 9-phenyl-9H-carbazol-3-ylboronic acid (100 g, 348 mmol) and 3-bromo-9H-carbazole (85.6 g, 348 mmol).

HRMS (70 eV, EI+): m/z calcd for C30H20N2: 408.1626, found: 408.

Elemental Analysis: C, 88%; H, 5%

Synthesis Example 23: Synthesis of Intermediate I-11

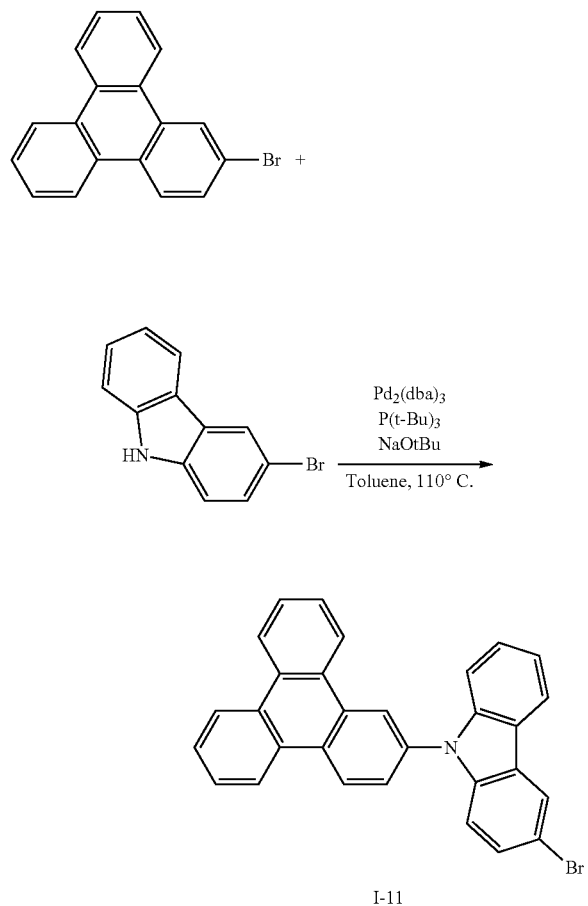

Intermediate I-11 (109 g, 71%) was obtained according to the same method as Synthesis Example 7 except for using 2-bromotriphenylene (100 g, 326 mmol) and 3-bromo-9H-carbazole (80.1 g, 326 mmol).

HRMS (70 eV, EI+): m/z calcd for C30H18BrN: 471.0623, found: 471.

Elemental Analysis: C, 76%; H, 4%

Synthesis Example 24: Synthesis of Compound E-1

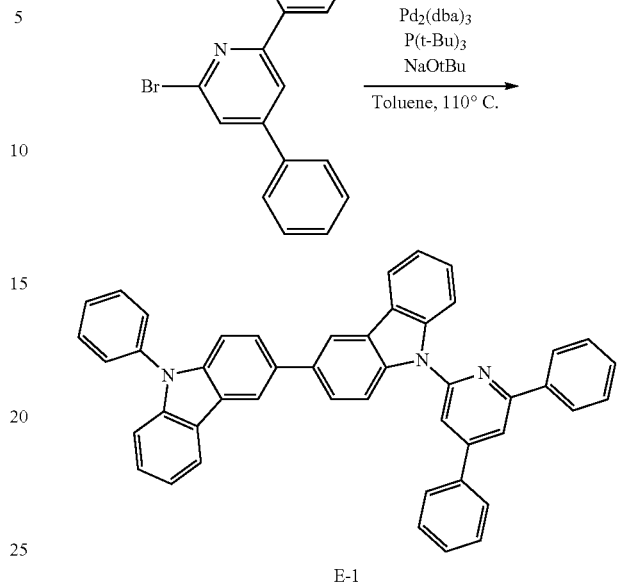

Compound E-1 (31.3 g, 77%) was obtained according to the same method as Synthesis Example 7 except for using Intermediate I-10 (20 g, 49.0 mmol) and 2-bromo-4,6-diphenylpyridine (15.1 g, 49.0 mmol) purchased from Amadis Chemical Co., Ltd. (http://www.amadischem.com/).

HRMS (70 eV, EI+): m/z calcd for C47H31N3: 637.2518, found: 637.

Elemental Analysis: C, 89%; H, 5%

Synthesis Example 25: Synthesis of Compound E-25

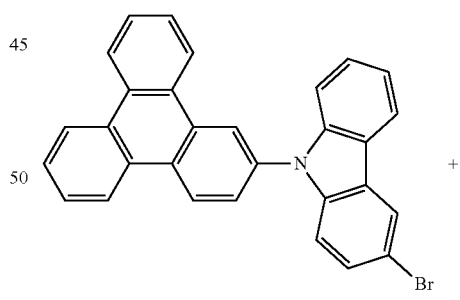

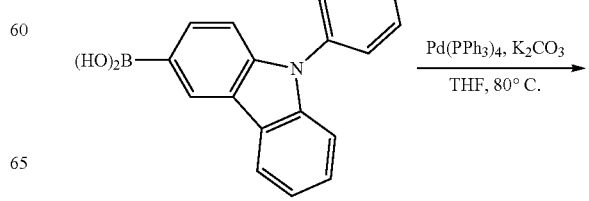

-continued

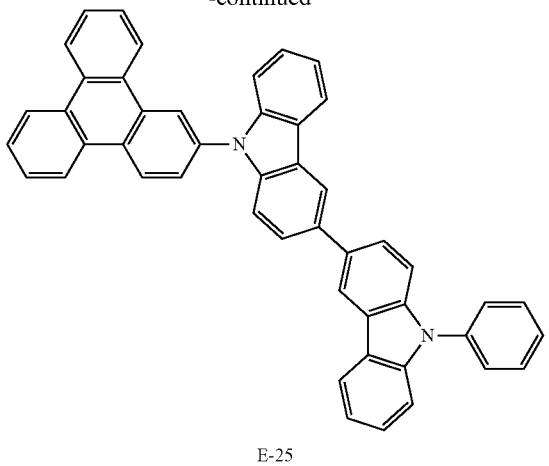

E-25

Compound E-25 (22.8 g, 85%) was obtained according to the same method as Synthesis Example 3 except for using Intermediate I-11 (20 g, 42.3 mmol) and 9-phenylcarbazol-3-ylboronic acid (12.1 g, 42.3 mmol).

HRMS (70 eV, EI+): m/z calcd for $C_{48}H_{30}N_2$: 634.2409, found: 634.

Elemental Analysis: C, 91%; H, 5%

Manufacture of Organic Light Emitting Diode

Example 10

ITO (indium tin oxide) was coated to be 1500 Å thick on a glass substrate, and the coated glass was ultrasonic wave-washed with a distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, N4,N4'-diphenyl-N4,N4'-bis(9-phenyl-9H-carbazol-3-yl)biphenyl-4,4'-diamine (Compound A) was vacuum-deposited on the ITO substrate to form a 700 Å-thick hole injection layer, 1,4,5,8,9,11-hexaazatriphenylene-hexacarbonitrile (HAT-CN) (Compound B) was deposited to be 50 Å thick on the injection layer, and N-(biphenyl-4-yl)-9,9-dimethyl-N-(4-(9-phenyl-9H-carbazol-3-yl)phenyl)-9H-fluoren-2-amine (Compound C) was deposited to be 1020 Å thick to form a hole transport layer. A 400 Å-thick light emitting layer was formed on the hole transport layer by vacuum-depositing Compound 1 of Synthesis Example 7 and Compound E-1 of Synthesis Example 24 simultaneously as a host and 10 wt % of tris(2-phenylpyridine)iridium (III) [Ir(ppy)$_3$] as a dopant. Herein, Compound 1 and Compound E-1 were used in a 1:1 ratio. Subsequently, 8-(4-(4,6-di(naphthalen-2-yl)-1,3,5-triazin-2-yl)phenyl)quinolone (Compound D) and Liq were vacuum-deposited simultaneously in a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically a structure of ITO/Compound A (700 Å)/Compound B (50 Å)/Compound C (1020 Å)/EML [Compound 1:Compound E-1:Ir(ppy)$_3$=X: X:10%] 400 Å/Compound D:Liq (300 Å)/Liq (15 Å)/Al (1200 Å). (X=weight ratio)

Examples 11 to 20

Each organic light emitting diode of Examples 11 to 20 was manufactured according to the same method as Example 10 by respectively using the first hosts and the second hosts shown in Table 5.

Comparative Examples 6 to 10

An organic light emitting diode of Comparative Example 6 was manufactured according to the same method as Example 10 by using 4,4'-di(9-carbazol-9-yl)biphenyl (CBP) instead of Compound 1 and each organic light emitting diode of Comparative Examples 7 to 10 was manufactured according to the same method as Example 10 by using the first hosts and the second hosts as shown in Table 5.

Evaluation 2

Luminous efficiency and life-span characteristics of each organic light emitting diode according to Examples 10 to 20 and Comparative Examples 6 to 10 were evaluated.

Specific measurement methods are as follows, and the results are shown in Table 5.

(1) Measurement of Current Density Change Depending on Voltage Change

Current values flowing in the unit device of the obtained organic light emitting diodes were measured, while increasing the voltage from 0 V to 10 V using a current-voltage meter (Keithley 2400), and the measured current values were divided by areas to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

The results were obtained by measuring time taken until current efficiency (cd/A) decreased down to 97% while luminance (cd/m2) was maintained at 6000 cd/m$^2$.

(5) Measurement of Driving Voltage

A driving voltage of each diode was measured using a current-voltage meter (Keithley 2400) at 15 mA/cm$^2$.

TABLE 5

| | First host | Second host | First host:Second host | Driving voltage (V) | Efficiency (cd/A) | 97% life-span (h) at 6000 cd/m² |
|---|---|---|---|---|---|---|
| Example 10 | 1 | E-1 | 1:1 | 3.61 | 50.3 | 650 |
| Example 11 | 1 | E-22 | 1:1 | 3.64 | 52.0 | 750 |
| Example 12 | 1 | E-25 | 1:1 | 3.77 | 51.0 | 950 |
| Example 13 | 1 | E-31 | 1:1 | 3.65 | 52.0 | 800 |
| Example 14 | 1 | E-31 | 3:7 | 3.70 | 52.9 | 900 |
| Example 15 | 5 | E-31 | 3:7 | 3.66 | 53.0 | 1,000 |
| Example 16 | 6 | E-31 | 3:7 | 3.62 | 53.2 | 950 |
| Example 17 | 13 | E-31 | 3:7 | 3.69 | 52.0 | 1,200 |
| Example 18 | 13 | E-31 | 1:1 | 3.65 | 55.7 | 1,050 |
| Example 19 | 13 | E-22 | 1:1 | 3.62 | 53.1 | 950 |
| Example 20 | 13 | E-22 | 3:7 | 3.63 | 51.7 | 1,000 |
| Comparative Example 6 | CBP | E-1 | 1:1 | 4.51 | 35.3 | 50 |
| Comparative Example 7 | Host 1 | E-1 | 1:1 | 4.53 | 45.1 | 150 |
| Comparative Example 8 | Host 2 | E-1 | 1:1 | 3.82 | 48.0 | 300 |
| Comparative Example 9 | Host 3 | E-1 | 1:1 | 4.40 | 45.0 | 100 |
| Comparative Example 10 | Host 2 | E-31 | 1:1 | 3.85 | 47.8 | 350 |

Referring to Table 5, the organic light emitting diodes according to Examples 10 to 20 exhibited remarkably improved luminous efficiency and driving voltage characteristics compared with the organic light emitting diodes according to Comparative Examples 6 to 105.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present disclosure in any way.

DESCRIPTION OF SYMBOLS 100, 200: organic light emitting diode
105: organic layer
110: cathode
120: anode
130: light emitting layer
140: hole auxiliary layer

What is claimed is:

1. A composition for an organic optoelectronic device, comprising:
a first compound represented by Chemical Formula 1; and
a second compound represented by Chemical Formula 2,

[Chemical Formula 1]

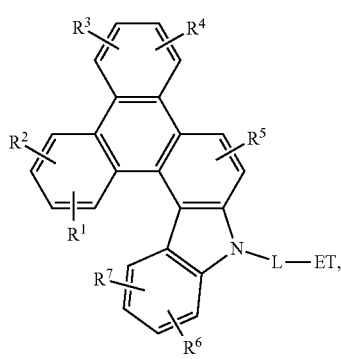

wherein, in Chemical Formula 1,
$R^1$ to $R^7$ are independently hydrogen, deuterium, a substituted or unsubstituted C1 to C5 alkyl group, or a substituted or unsubstituted C6 to C18 aryl group,
L is a single bond, a substituted or unsubstituted C6 to C20 arylene group, or a substituted or unsubstituted C2 to C30 heteroarylene group, and
ET is a substituted or unsubstituted C2 to C30 heterocyclic group including at least two N's,
wherein, in Chemical Formula 1, the "substituted" refers to replacement of at least one hydrogen by deuterium, a cyano group, a C1 to C20 alkyl group, a C6 to C30 aryl group, or a C2 to C30 heteroaryl group;

[Chemical Formula 2]

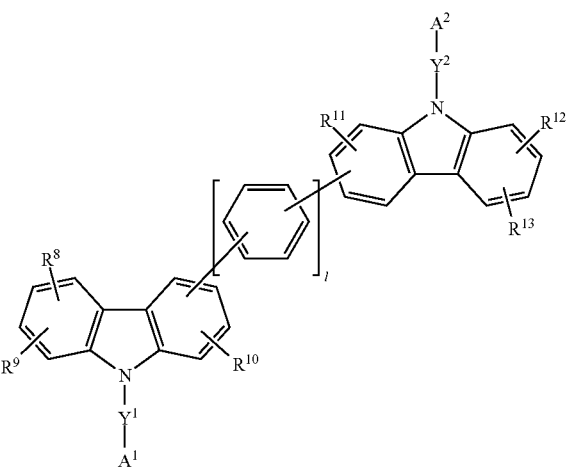

wherein, in Chemical Formula 2,
$Y^1$ and $Y^2$ are independently a single bond, a substituted or unsubstituted C6 to C30 arylene group, a substituted or unsubstituted C2 to C30 heteroarylene group, or a combination thereof,
$A^1$ and $A^2$ are independently substituted or unsubstituted C6 to C30 aryl group, a substituted or unsubstituted C2 to C30 heterocyclic group, or a combination thereof,
$R^8$ to $R^{13}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and l is an integer of 0 to 2;

wherein the "substituted" refers to replacement of at least one hydrogen by deuterium, a C1 to C4 alkyl group, a C6 to C18 aryl group, or a C2 to C30 heteroaryl group.

2. The composition for an organic optoelectronic device as claimed in claim 1, wherein ET of Chemical Formula 1 is a substituted or unsubstituted pyrimidinyl group, a substituted or unsubstituted triazinyl group, a substituted or unsubstituted quinazolinyl group, a substituted or unsubstituted benzoquinazolinyl group, a substituted or unsubstituted benzothieno[3,2-d]pyrimidinyl group, a substituted or unsubstituted benzothieno[2,3-d]pyrimidinyl group, a substituted or unsubstituted benzofuro[3,2-d]pyrimidinyl group, or a substituted or unsubstituted benzofuro[2,3-d]pyrimidinyl group.

3. The composition for an organic optoelectronic device as claimed in claim 1, wherein the first compound represented by Chemical Formula 1 is represented by one of Chemical Formula 1-I, Chemical Formula 1-II, Chemical Formula 1-III, Chemical Formula 1-IV, Chemical Formula 1-V and Chemical Formula 1-VI:

[Chemical Formula 1-I]

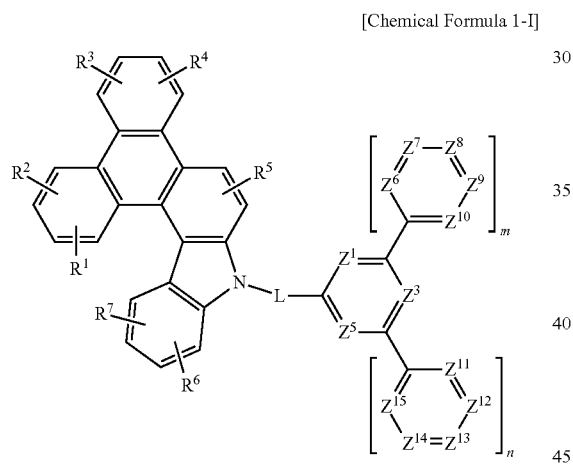

[Chemical Formula 1-II]

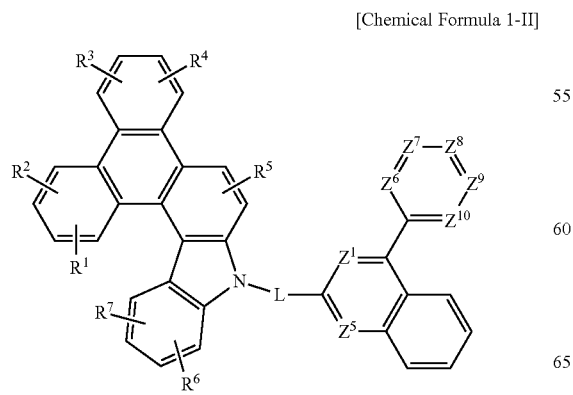

[Chemical Formula 1-III]

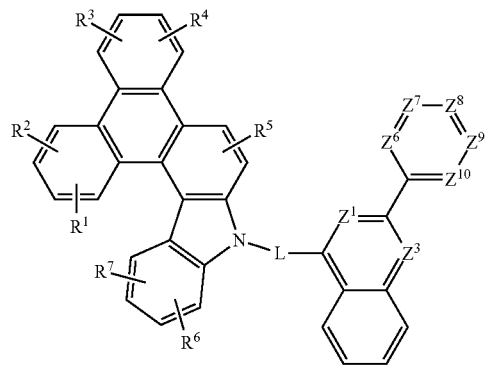

[Chemical Formula 1-IV]

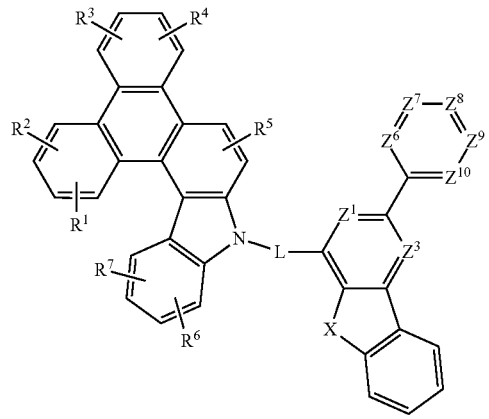

[Chemical Formula 1-V]

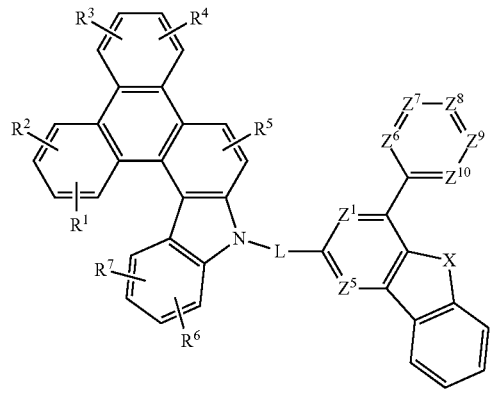

[Chemical Formula 1-VI]

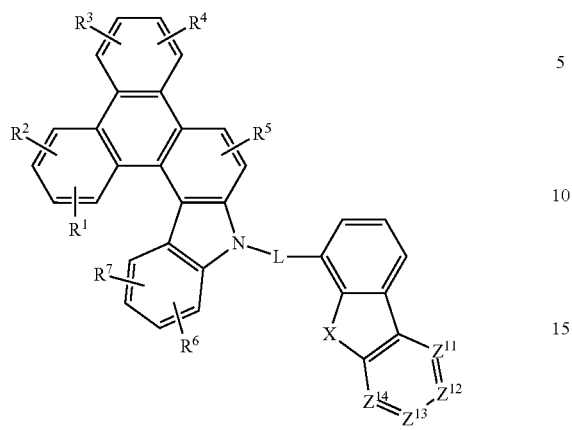

wherein, in Chemical Formula 1-I, Chemical Formula 1-II, Chemical Formula 1-III, Chemical Formula 1-IV, Chemical Formula 1-V, and Chemical Formula 1-VI, $Z^1$, $Z^3$, $Z^5$, and $Z^6$ to $Z^5$ are independently N or $CR^a$, m and n are independently an integer of 0 to 2, X is O or S, at least two of $Z^1$, $Z^3$ and $Z^5$ of Chemical Formula 1-I to Chemical Formula 1-V are N, at least two of $Z^{11}$ to $Z^{14}$ of Chemical Formula 1-VI are N, $R^a$ and $R^1$ to $R^7$ are independently hydrogen, deuterium, a substituted or unsubstituted C1 to C5 alkyl group, or a substituted or unsubstituted C6 to C18 aryl group, and L is a single bond, a substituted or unsubstituted C6 to C20 arylene group, or a substituted or unsubstituted C2 to C30 heteroarylene group.

4. The composition for an organic optoelectronic device as claimed in claim 1, wherein ET of Chemical Formula 1 is selected from substituents of Group I:

[Group I]

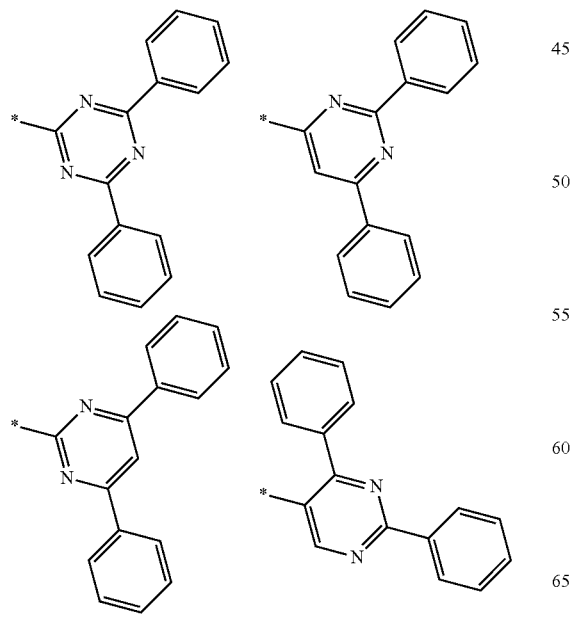

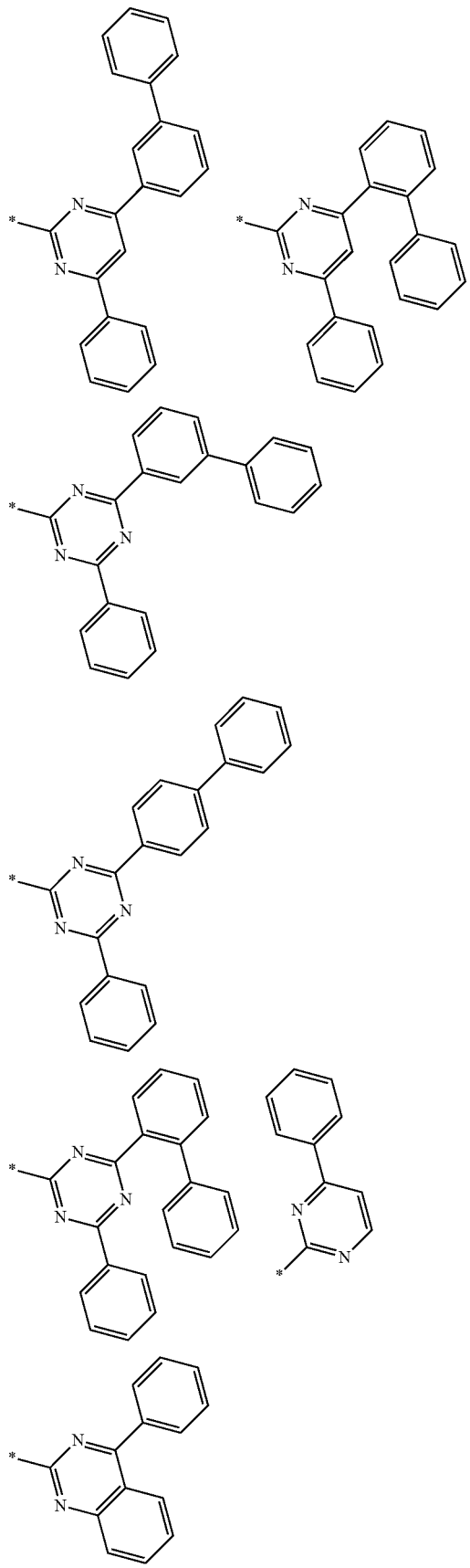

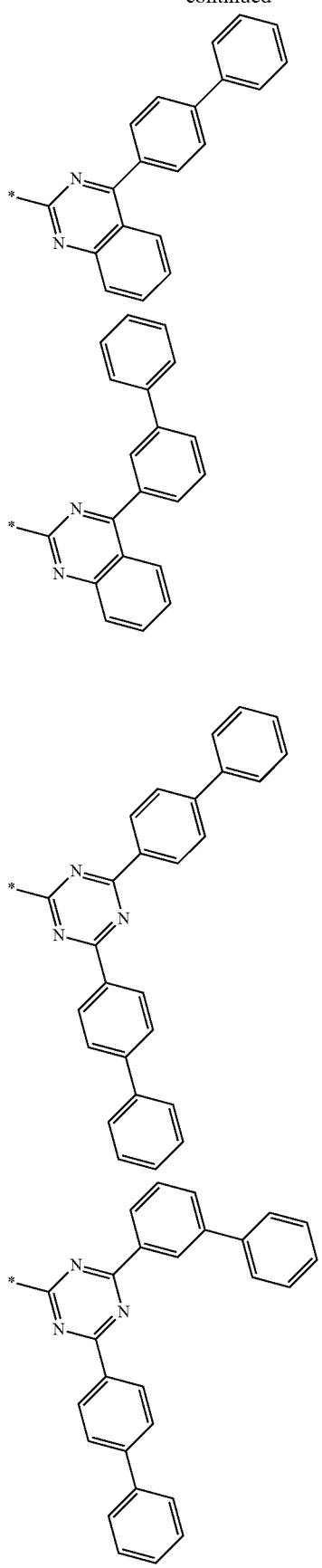
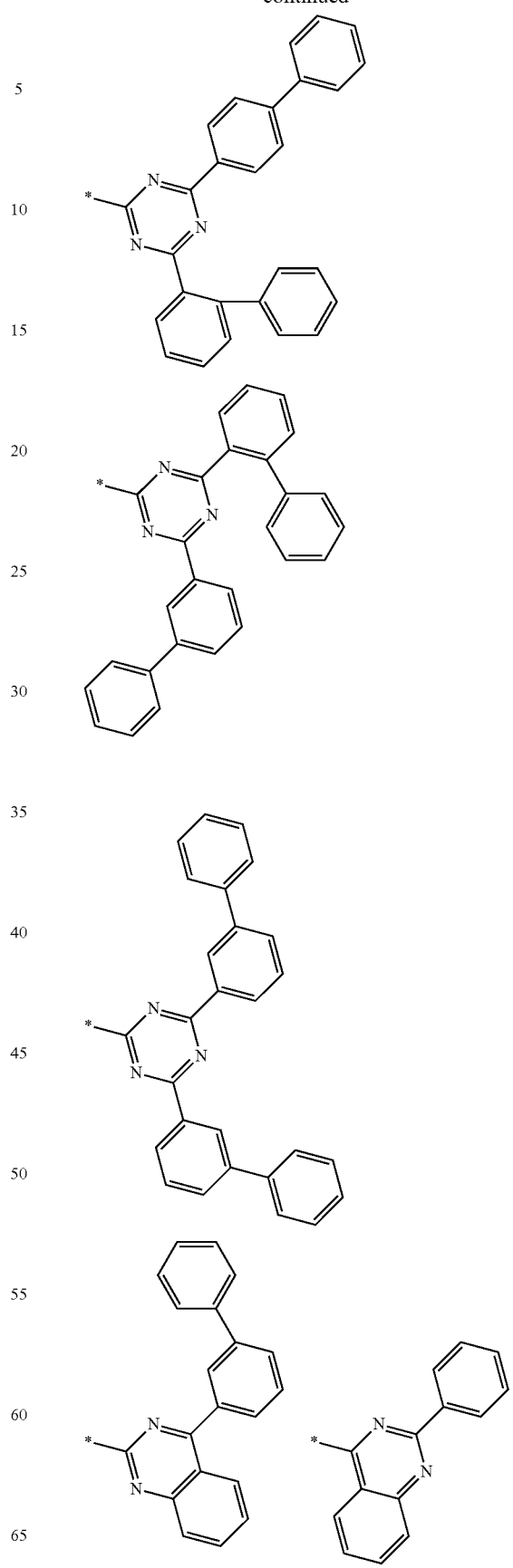

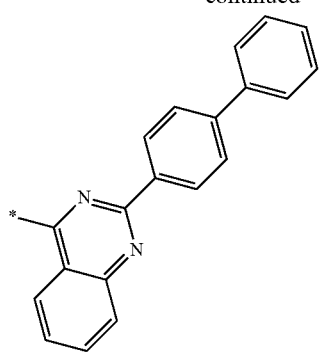
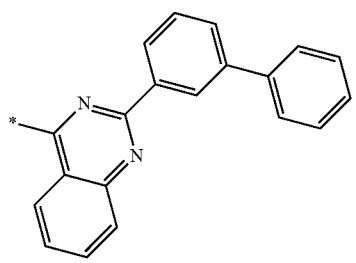
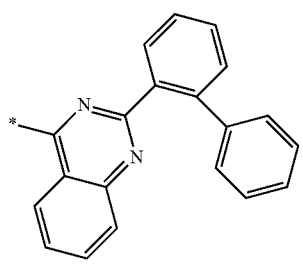
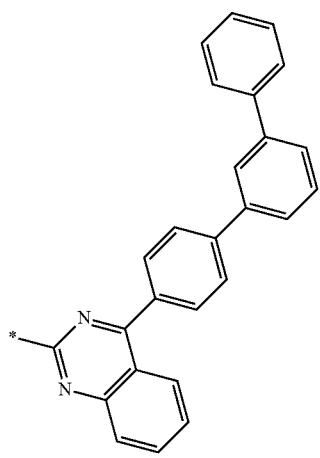
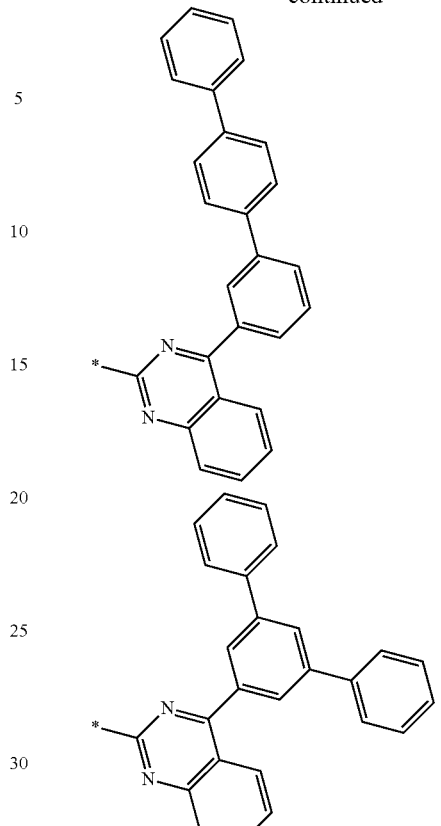
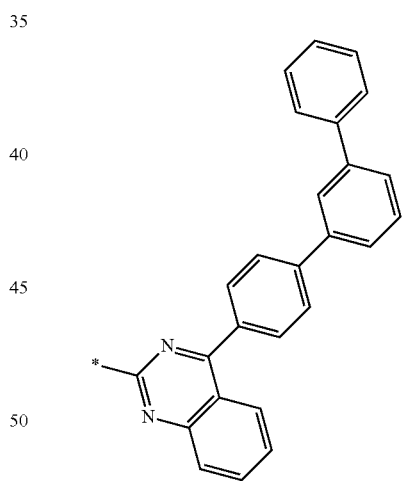
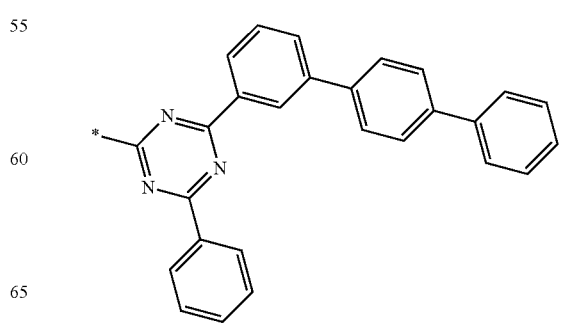

133
-continued
134
-continued
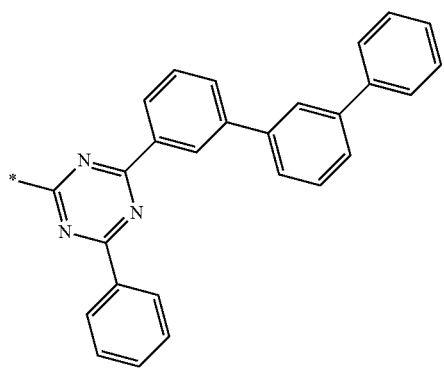
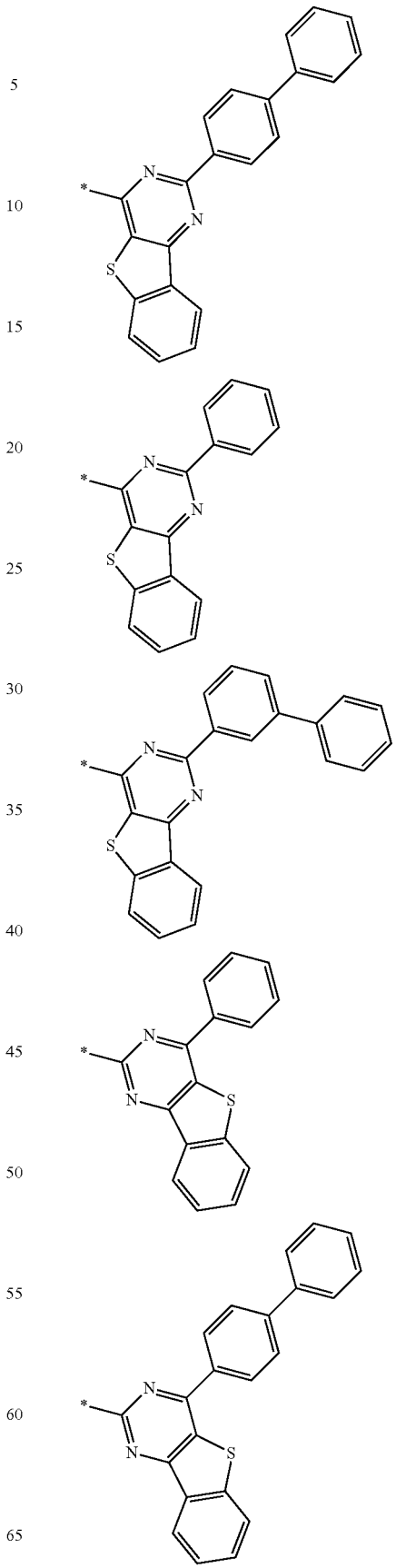

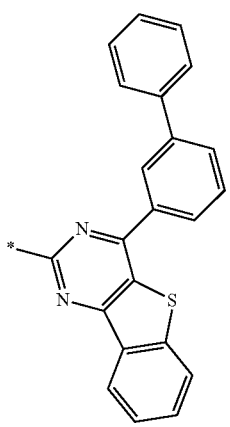

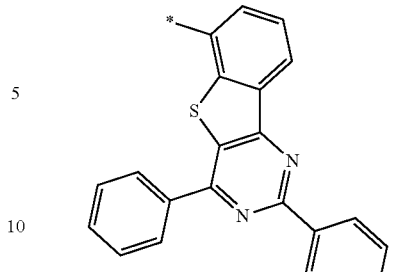

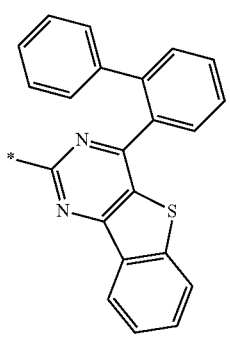

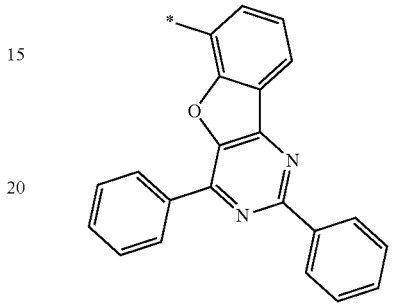

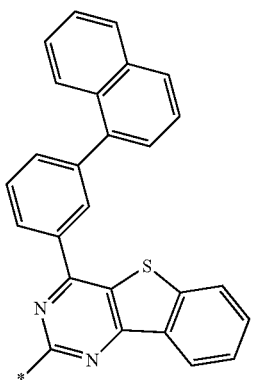

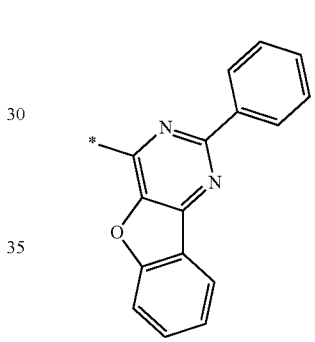

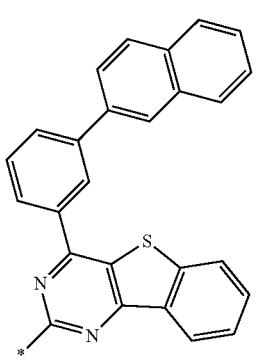

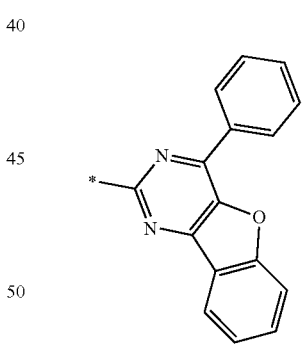

wherein, in Group I, is a linking point with "L" of Chemical Formula 1.

5. The composition for an organic optoelectronic device as claimed in claim 1, wherein L of Chemical Formula 1 is a single bond, a substituted or unsubstituted phenylene group, a substituted or unsubstituted biphenylene group, a substituted or unsubstituted terphenylene group, or a substituted or unsubstituted naphthylene group.

6. The composition for an organic optoelectronic device as claimed in claim 1, wherein the first compound represented by Chemical Formula 1 is selected from compounds of Group 1:

[Group 1]
1
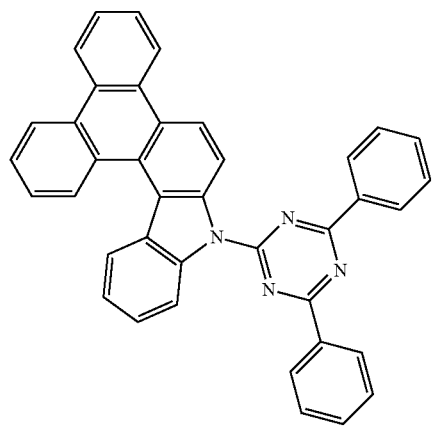
2
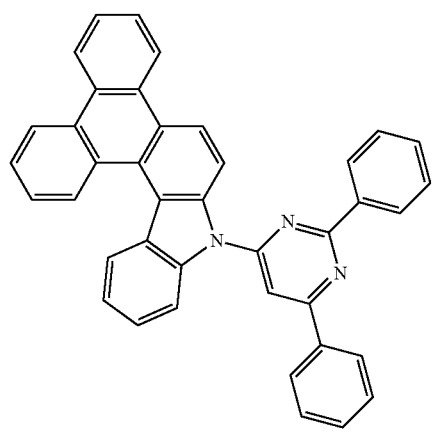
3
4
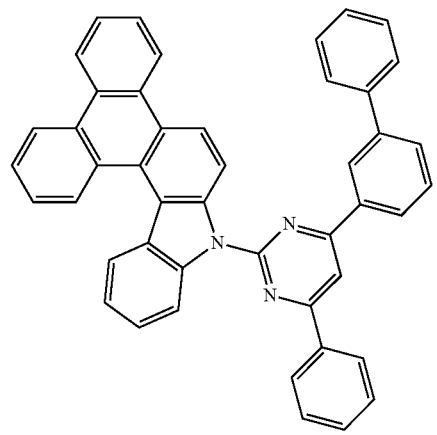
5
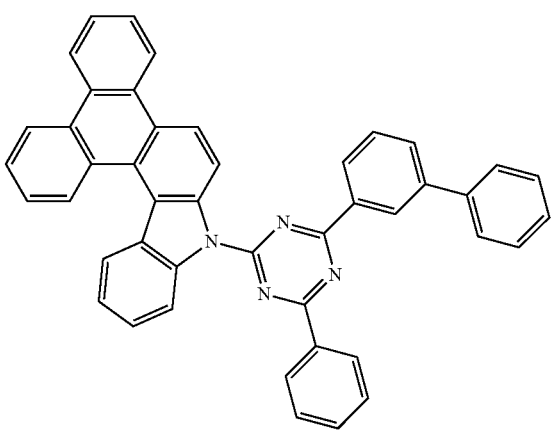
6
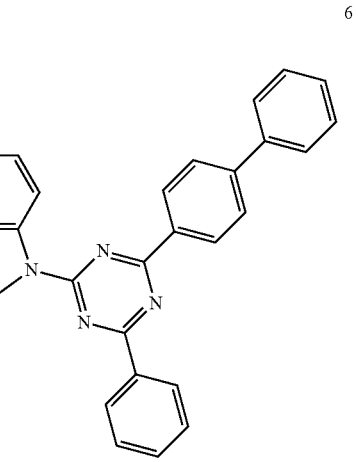

7
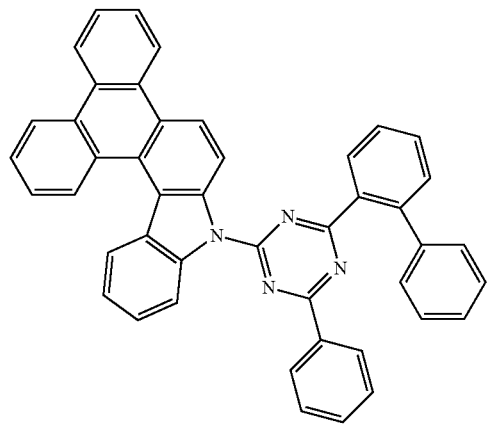
8
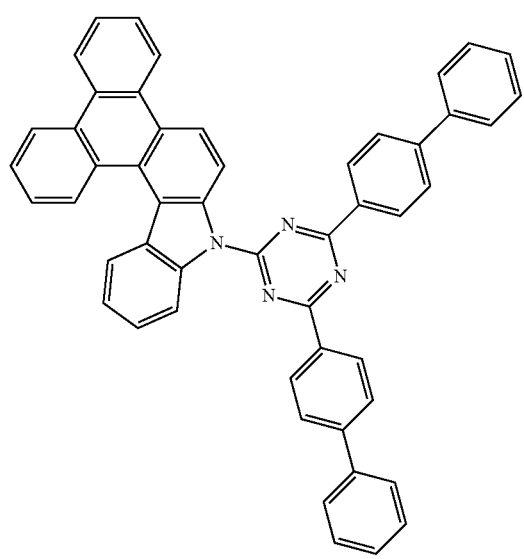
9
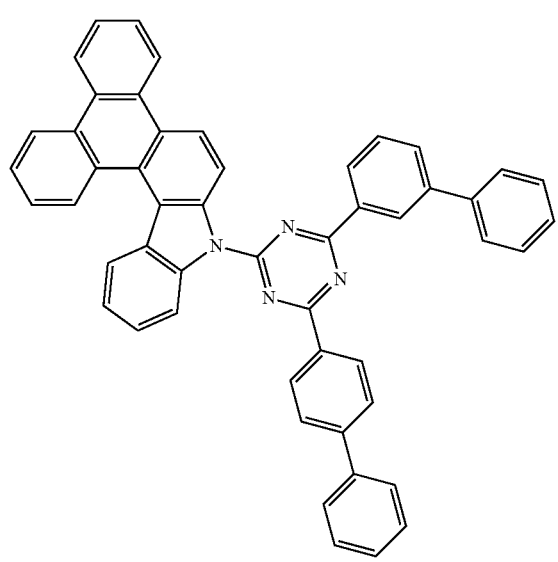
10
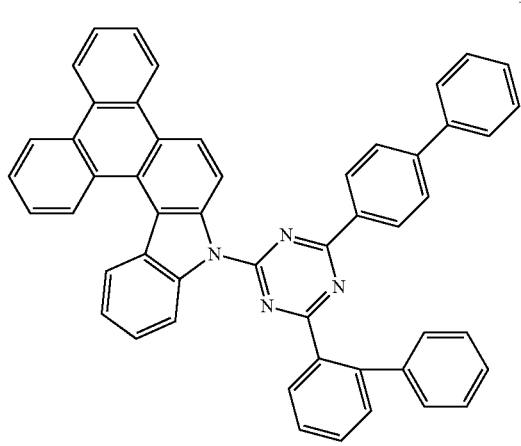
11
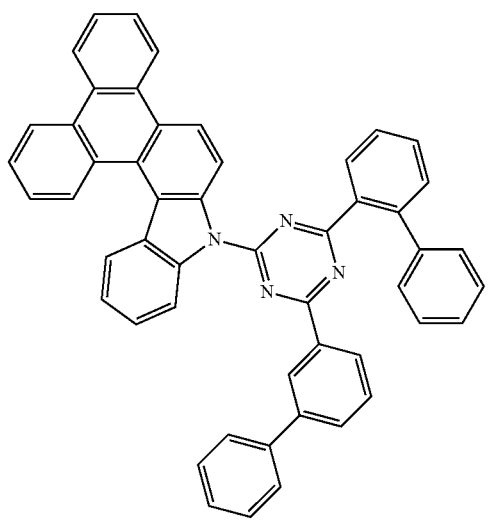
12
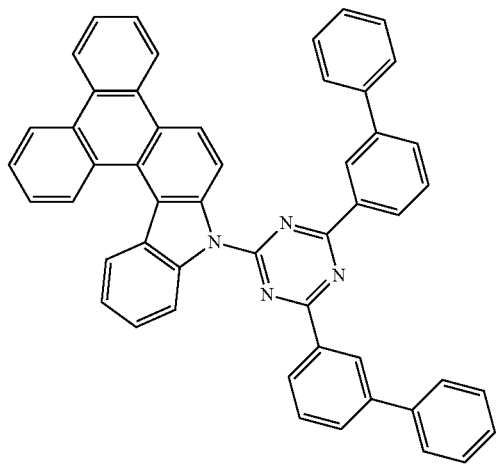

13
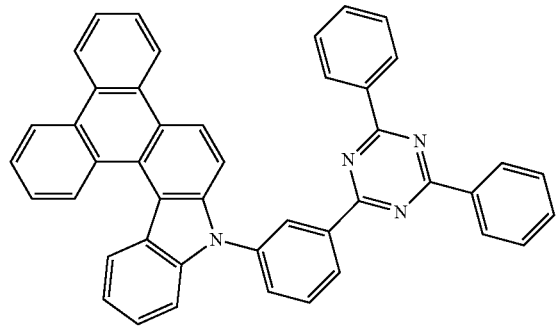
14
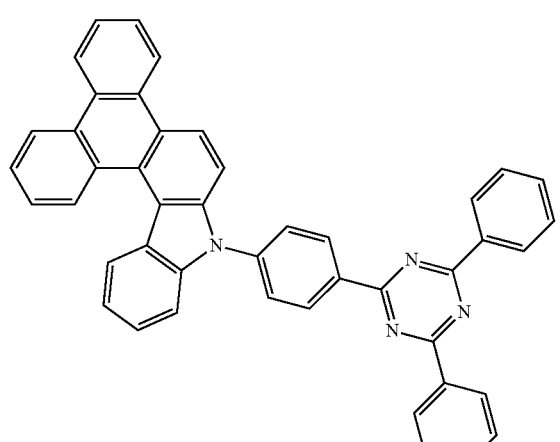
15
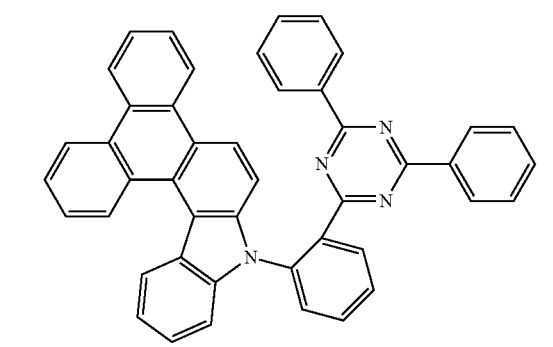
16
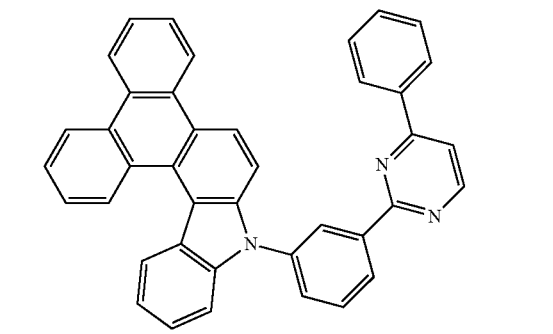
17
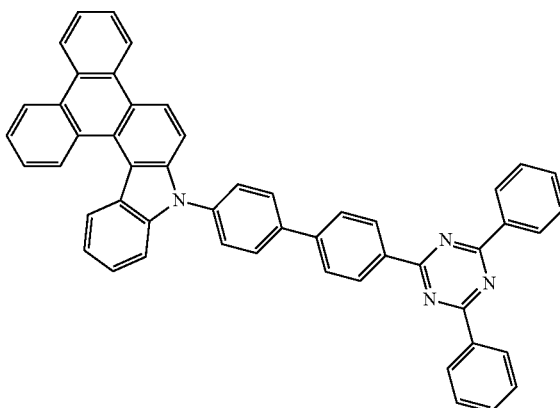
18
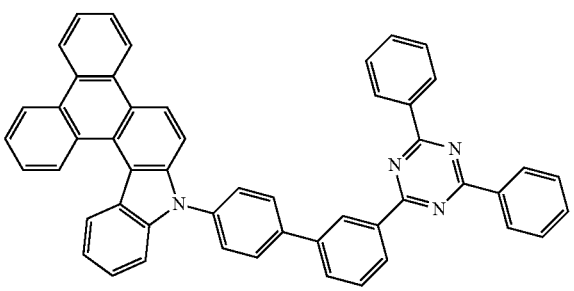
19
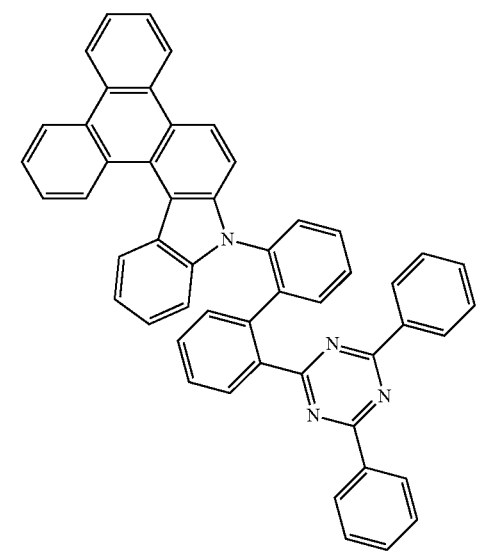

143
-continued
20
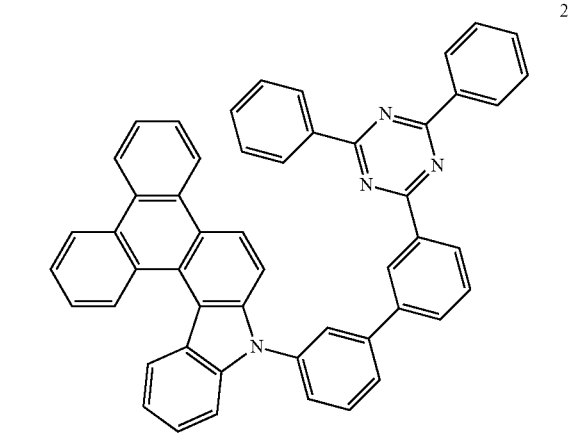
21
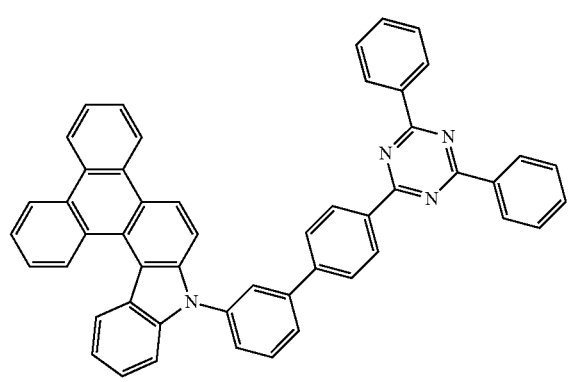
22
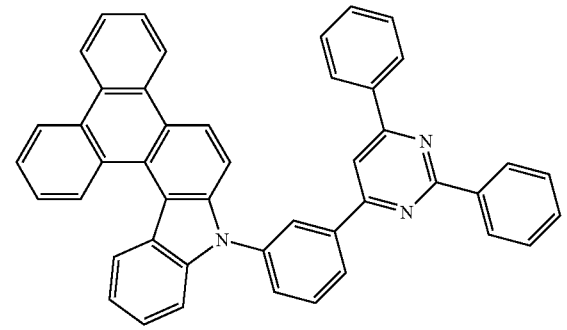
23
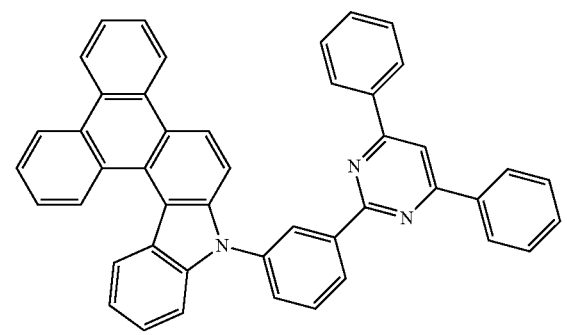
144
-continued
24
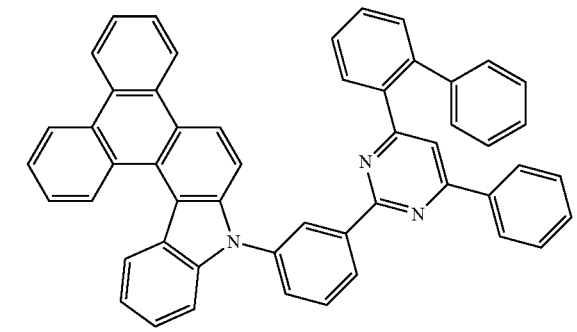
25
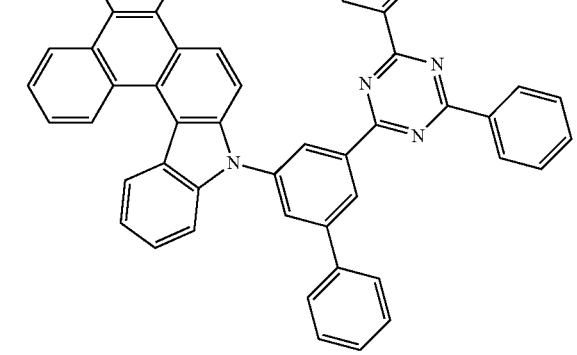
26
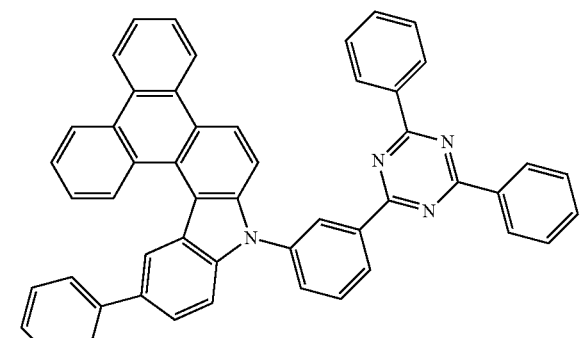
27
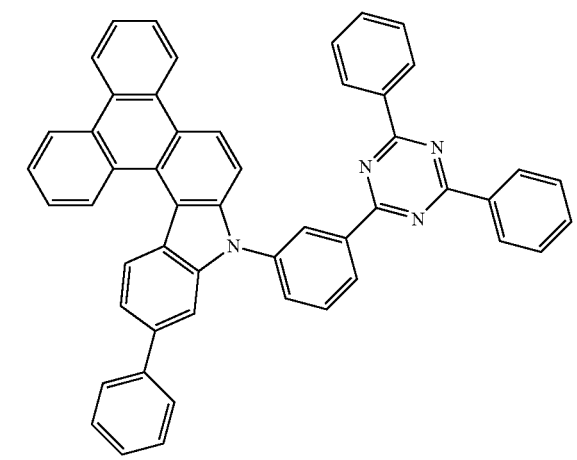

28
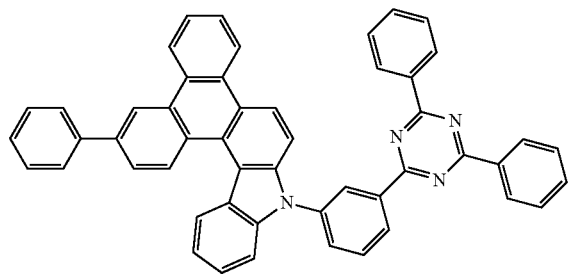
29
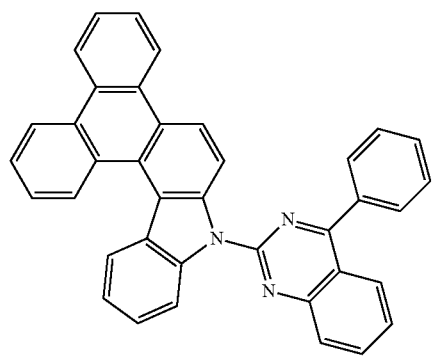
30
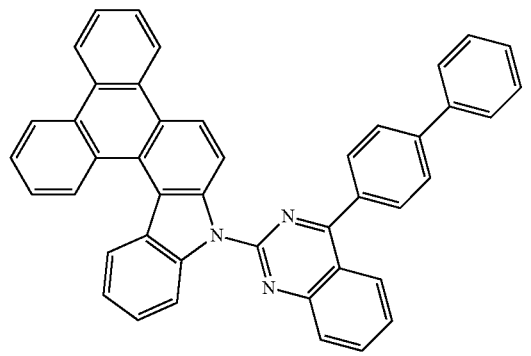
31
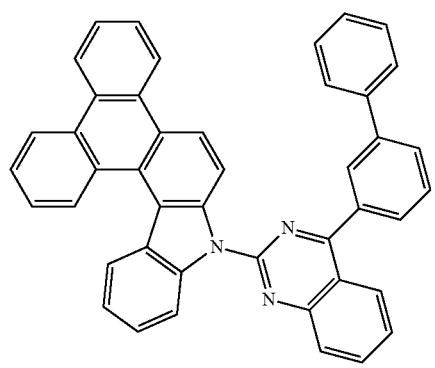
32
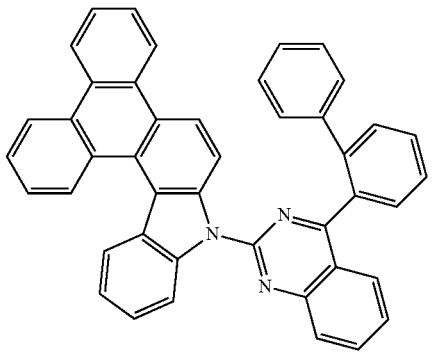
33
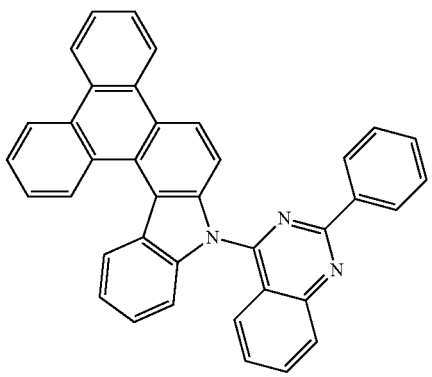
34
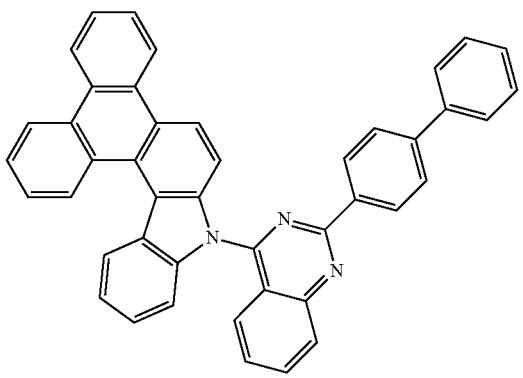
35
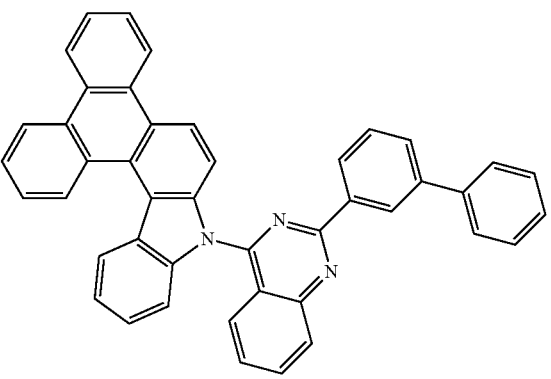

36
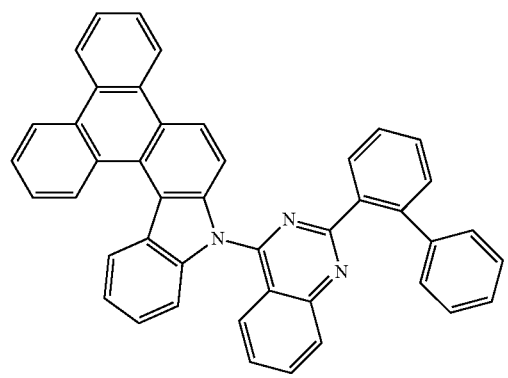
37
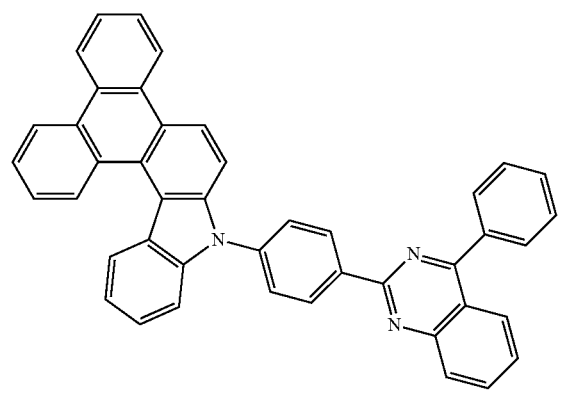
38
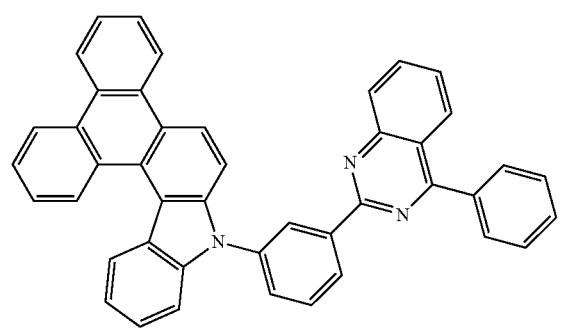
39
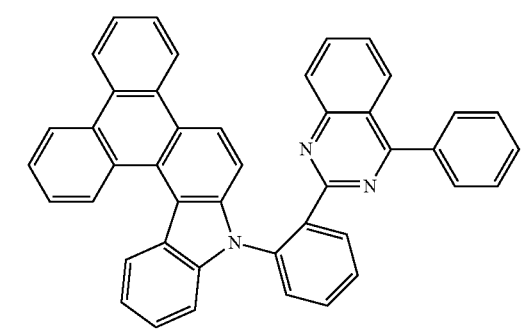
40
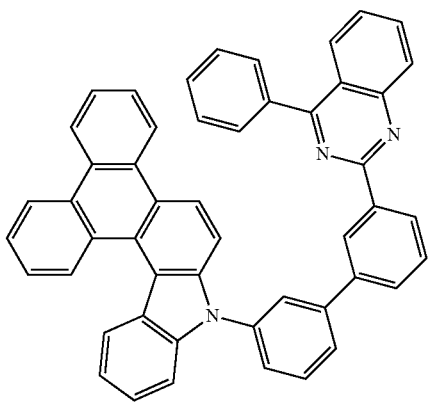
41
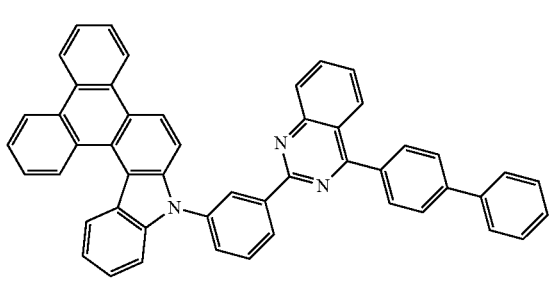
42
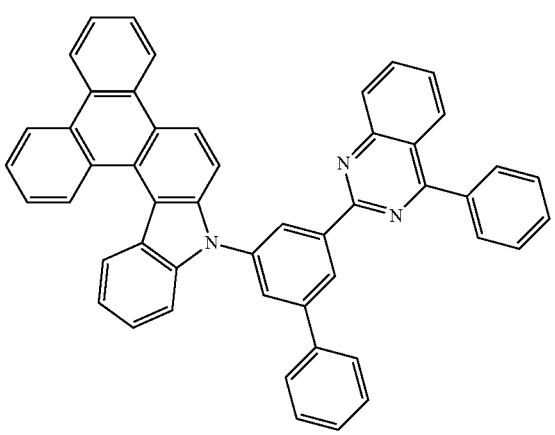
43
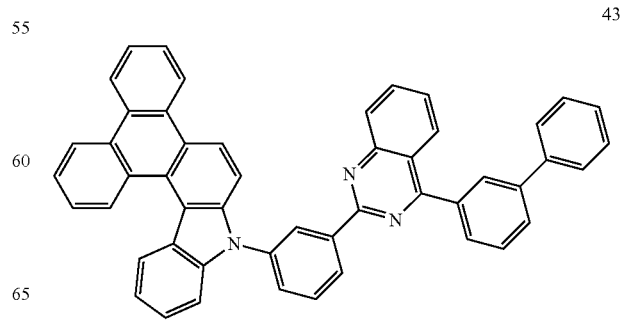

-continued
44
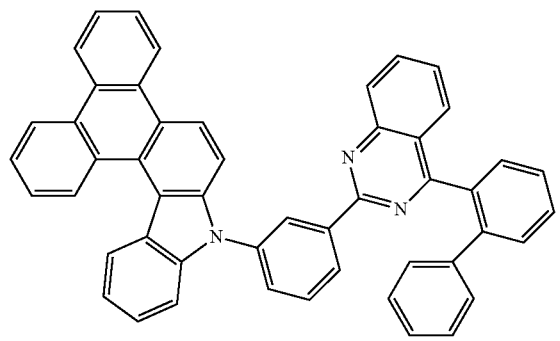
45
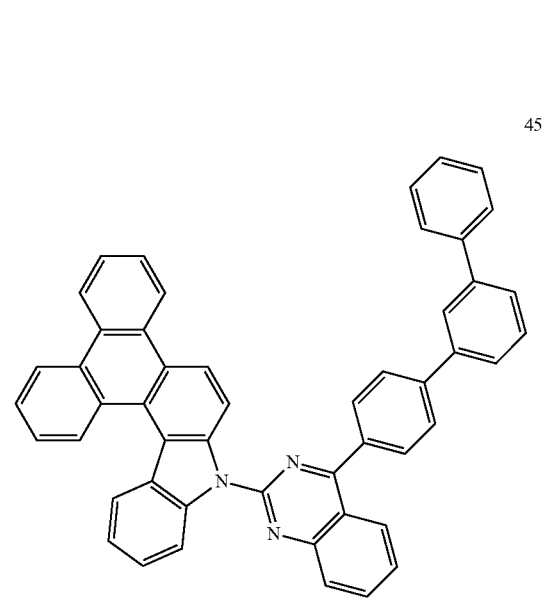
46
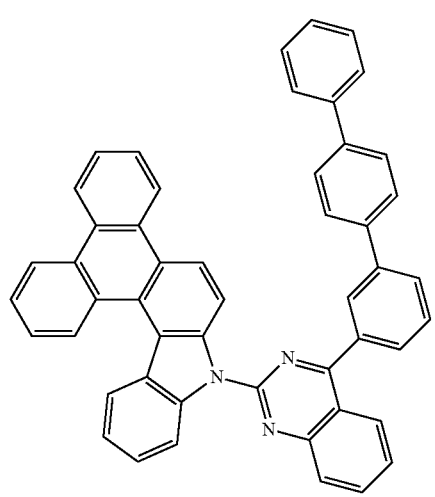
-continued
47
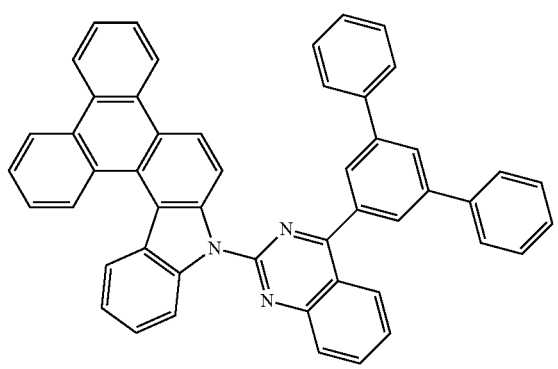
48
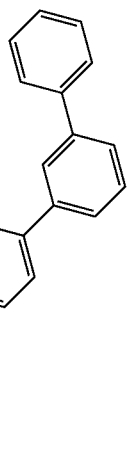
49
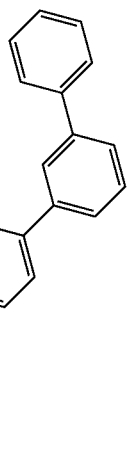
50
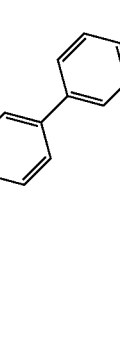

151
-continued
51
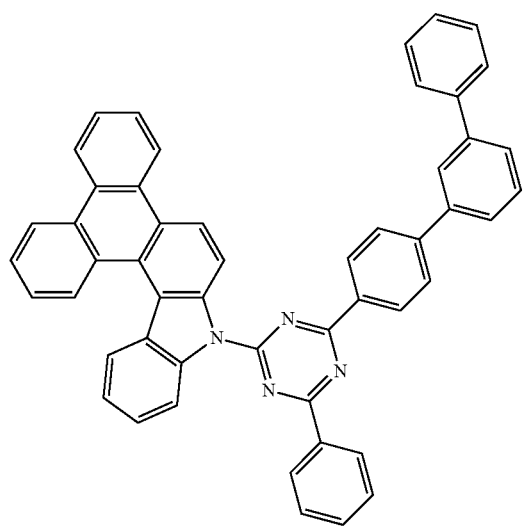
52
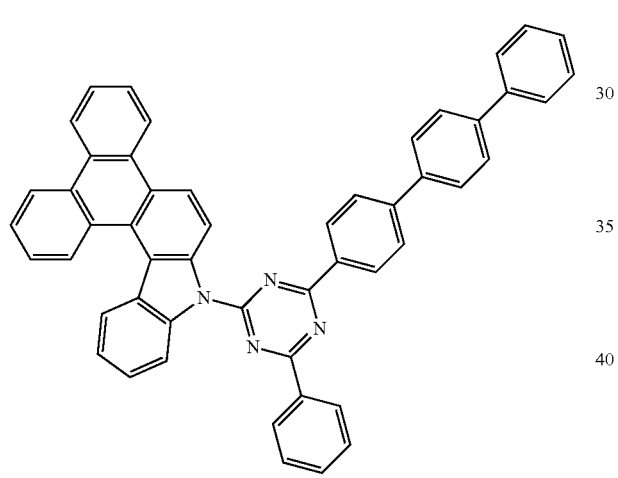
53
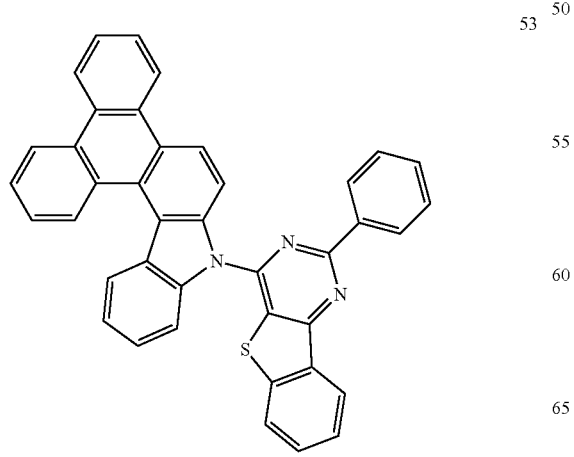
152
-continued
54
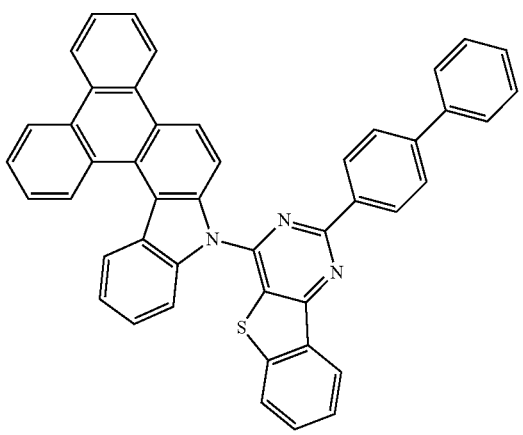
55
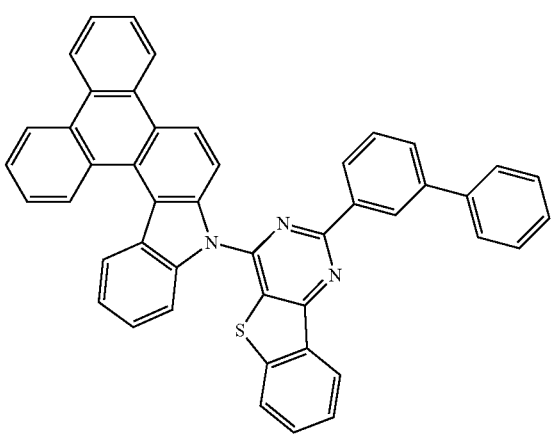
56
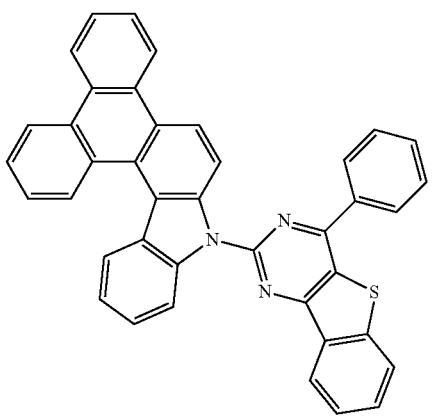

153
-continued
57
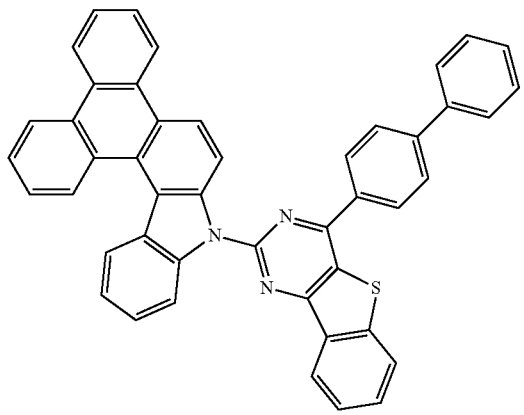
58
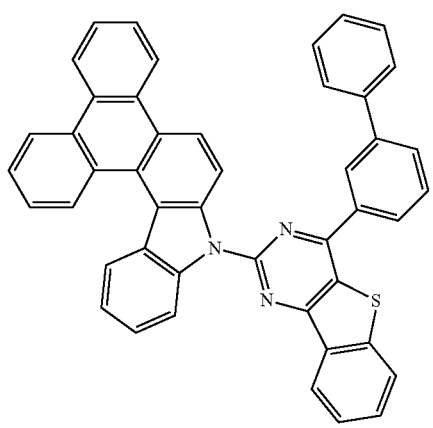
59
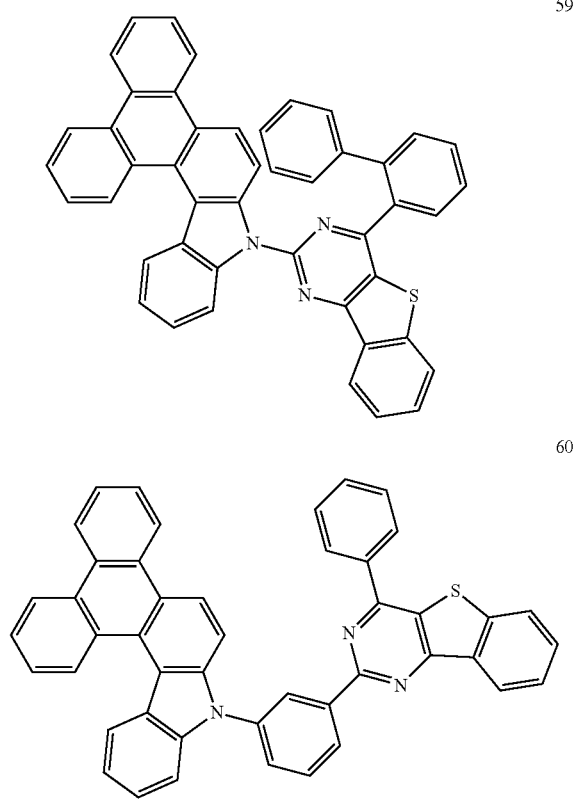
154
-continued
61
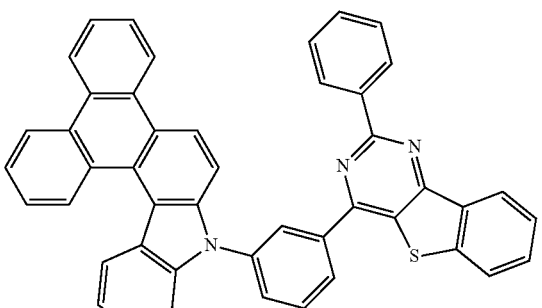
62
63
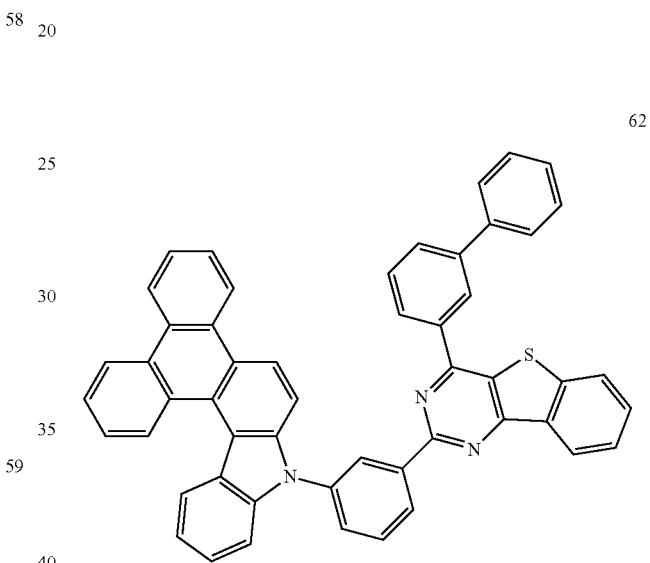

64
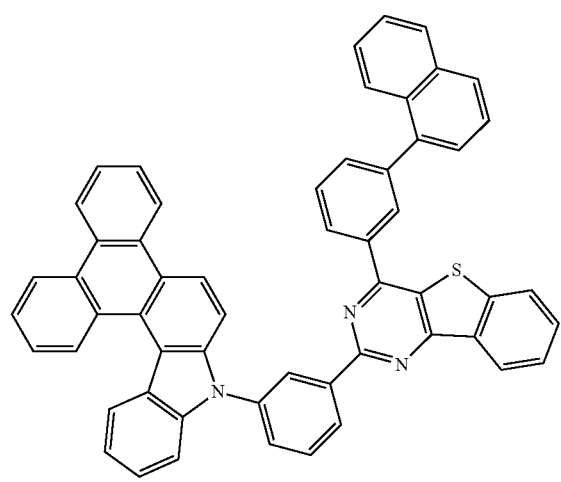
65
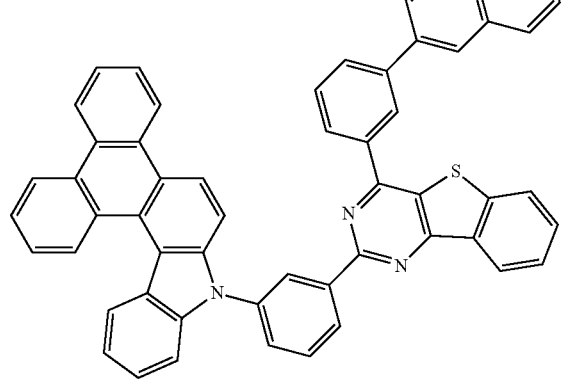
66
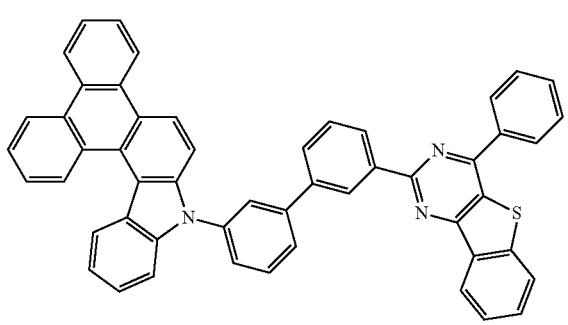
67
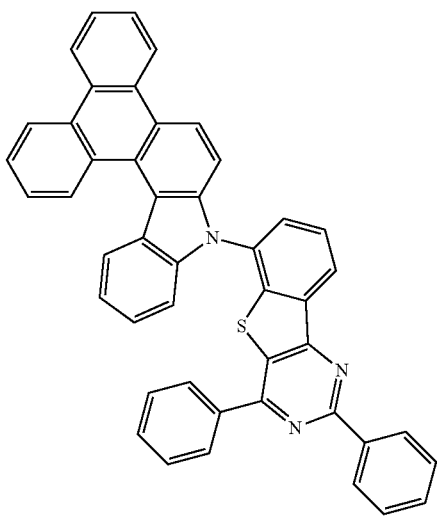
68
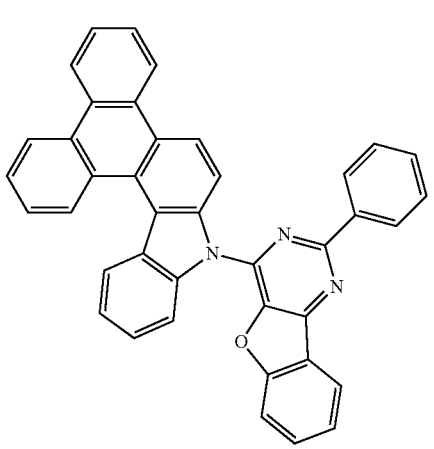
69

-continued

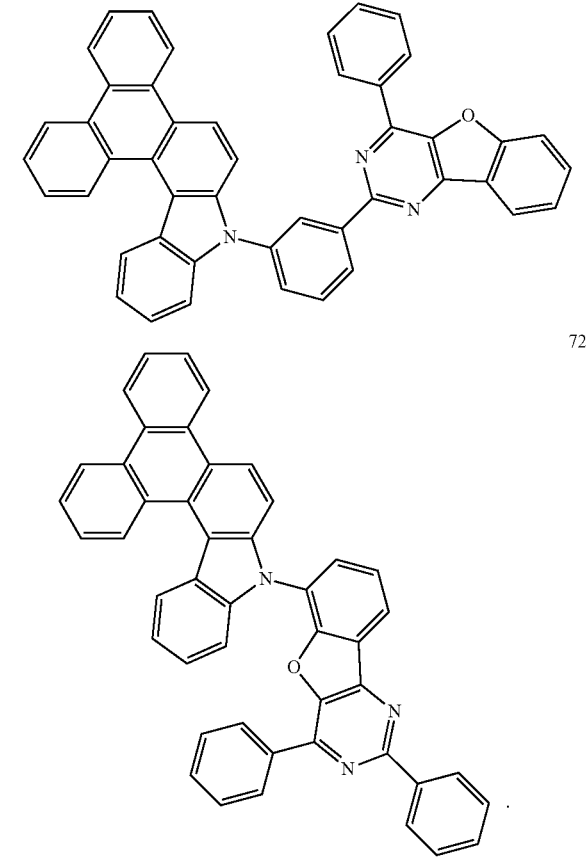

7. The composition for an organic optoelectronic device as claimed in claim 1, wherein $A^1$ and $A^2$ of Chemical Formula 2 are independently a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted anthracenyl group, a substituted or unsubstituted triphenylene group, a substituted or unsubstituted pyridinyl group, a substituted or unsubstituted dibenzofuranyl group, a substituted or unsubstituted dibenzothiophenyl group, a substituted or unsubstituted carbazolyl group, a substituted or unsubstituted fluorenyl group, or a combination thereof.

8. The composition for an organic optoelectronic device as claimed in claim 1, wherein:

Chemical Formula 2 has one of structures of Group II, and *—$Y^1$-$A^1$ and *—$Y^2$-$A^2$ of Chemical Formula 2 are one of substituents of Group III:

[Group II]

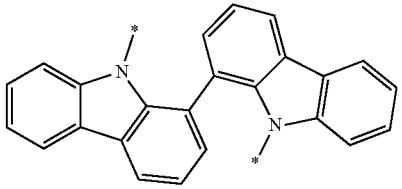
C-1

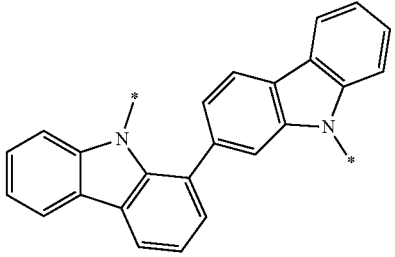
C-2

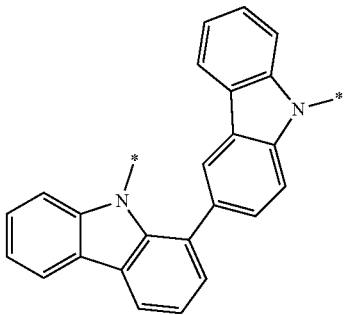
C-3

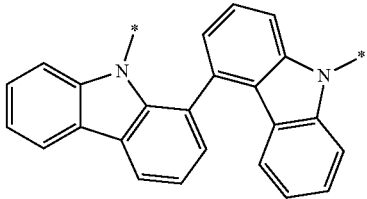
C-4

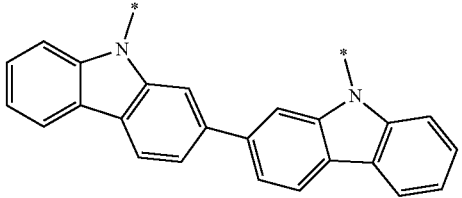
C-5

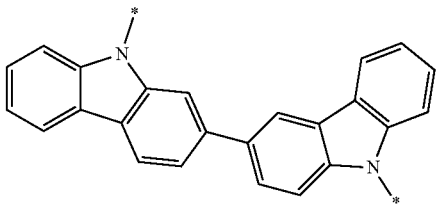
C-6

-continued
C-7
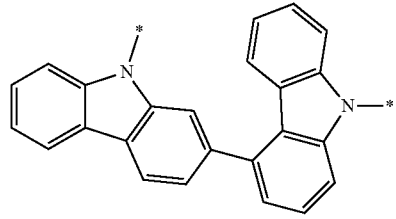
C-8
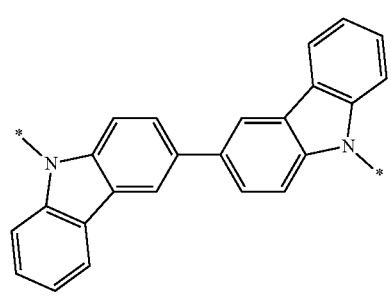
C-9
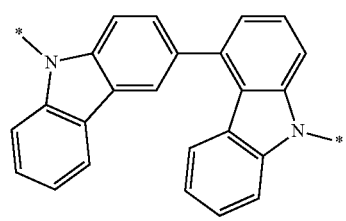
C-10
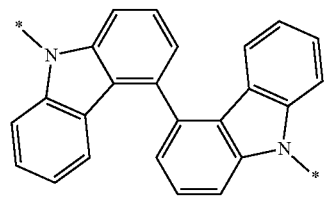
C-11
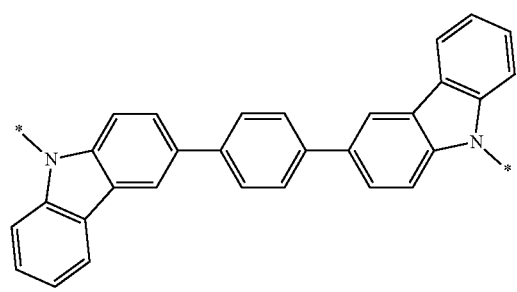
C-12
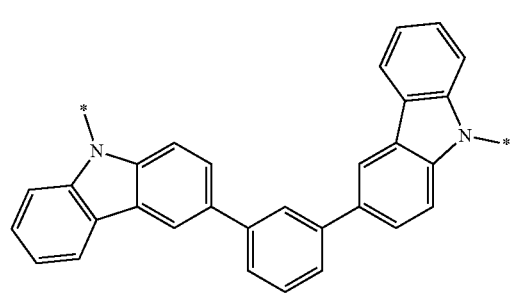
-continued
C-13
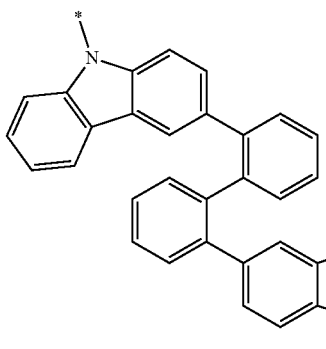
C-14
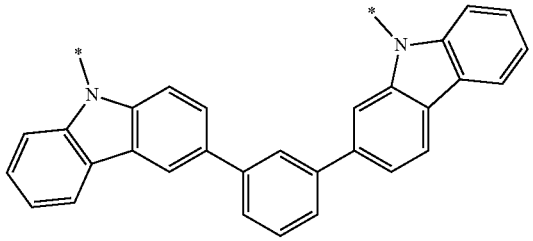
C-15
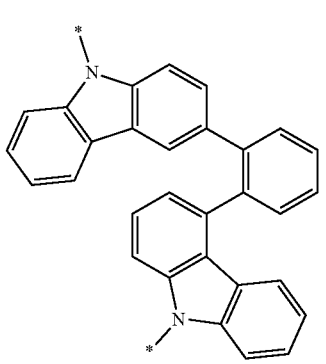
C-16
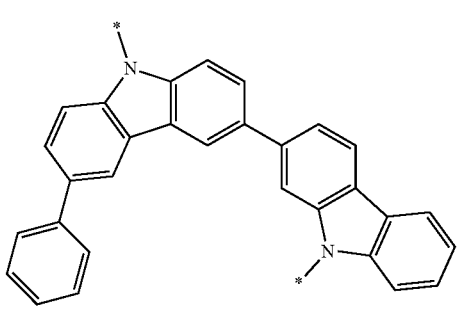
C-17
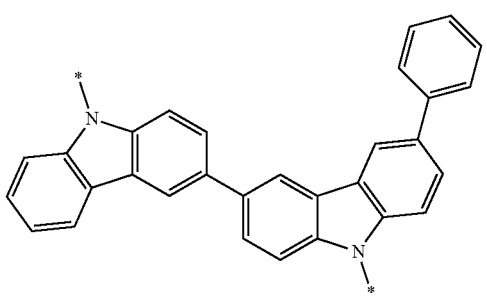

-continued
C-18
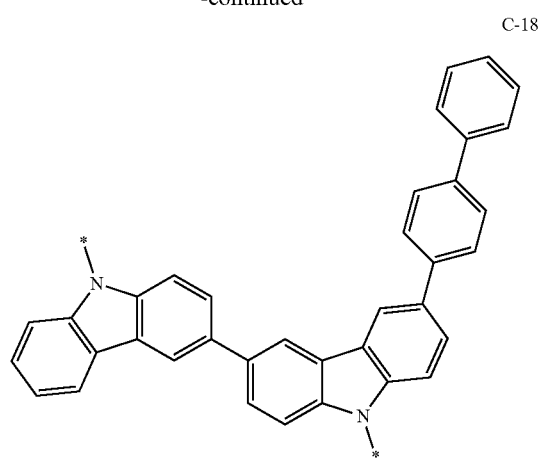
[Group III]
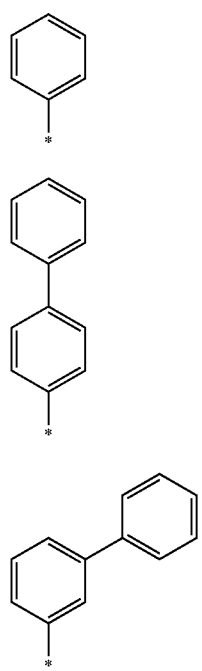
B-1
B-2
B-3
B-4
B-5
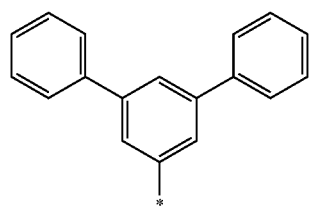
B-6
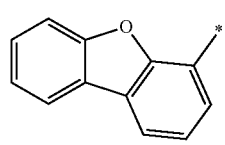
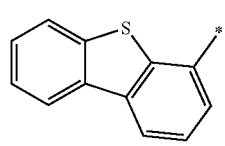
-continued
B-7
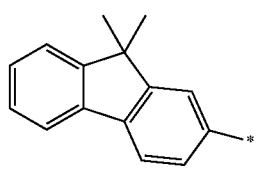
B-8
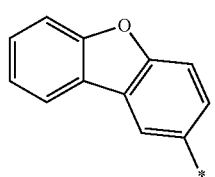
B-9
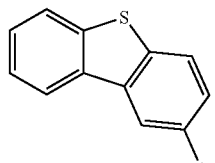
B-10
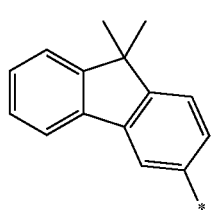
B-11
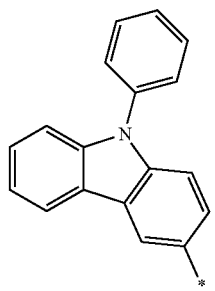
B-12
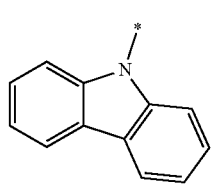
B-13
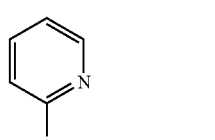
B-14
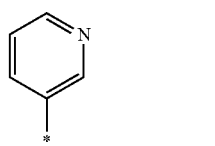

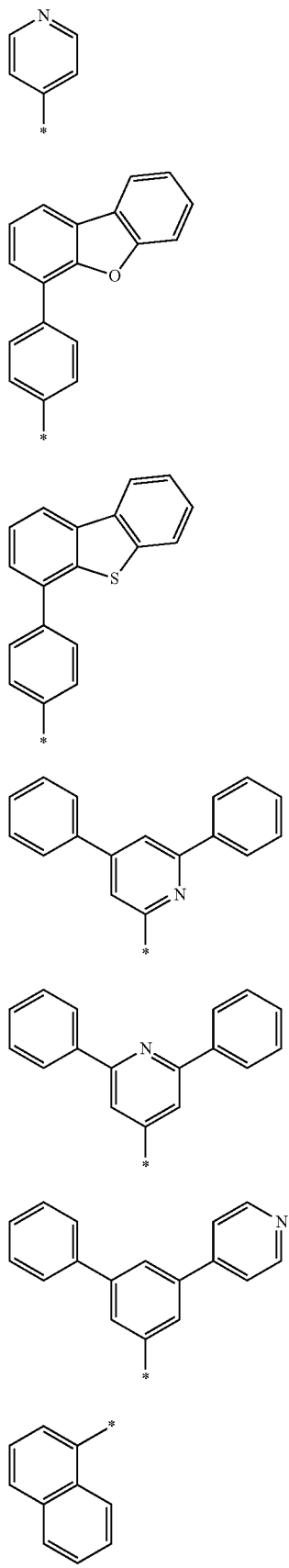
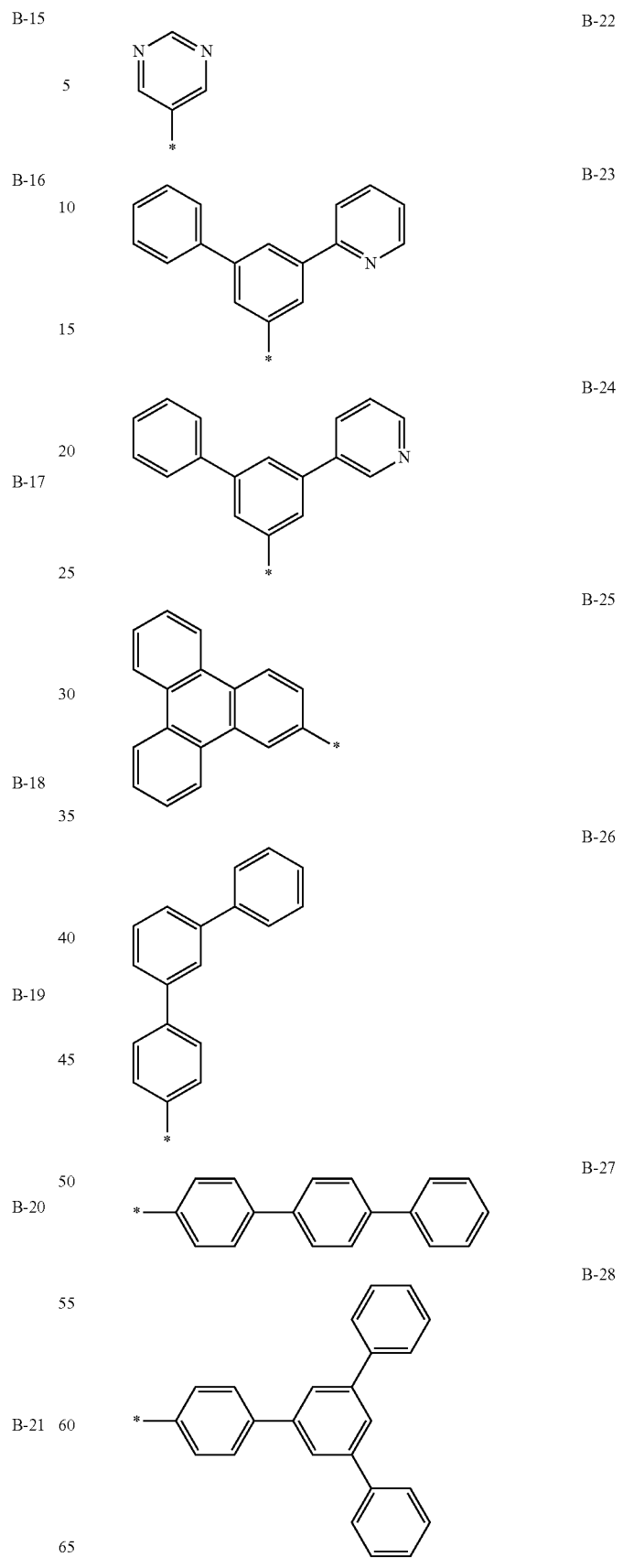

[Group III]
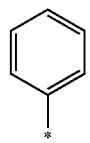
B-1
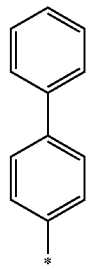
B-2
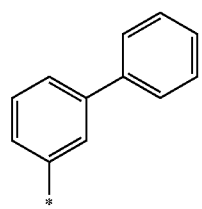
B-3
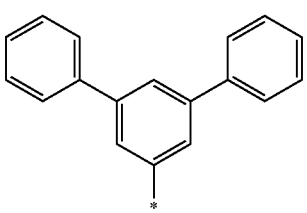
B-4
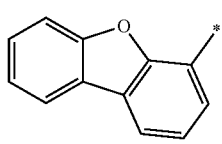
B-5
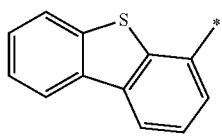
B-6
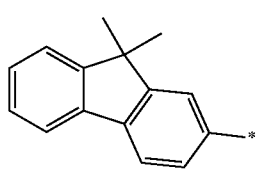
B-7
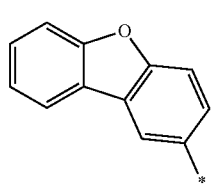
B-8
-continued
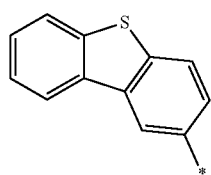
B-9
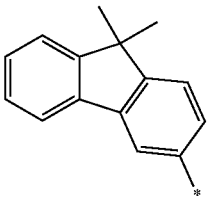
B-10
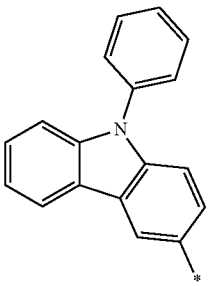
B-11
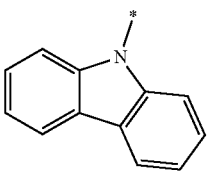
B-12
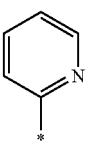
B-13
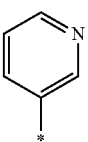
B-14
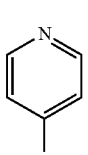
B-15
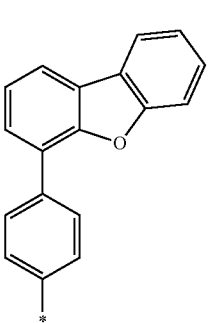
B-16

B-17

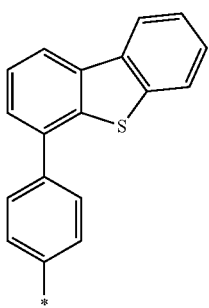

B-18

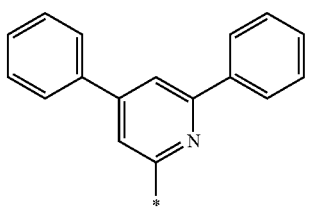

B-19

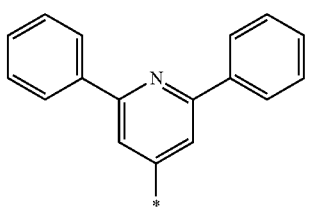

B-20

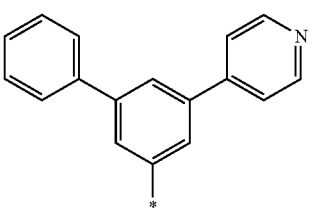

B-21

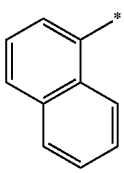

B-22

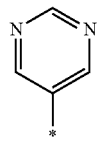

B-23

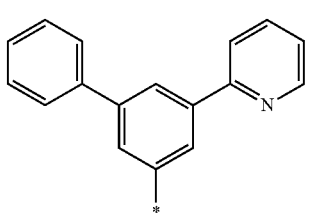

B-24

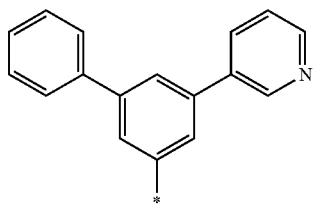

B-25

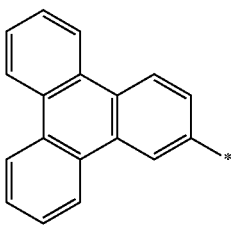

B-26

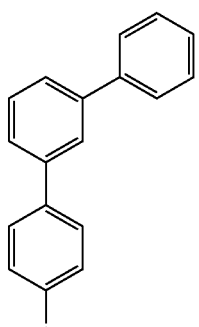

B-27

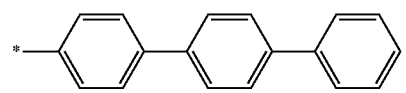

B-28

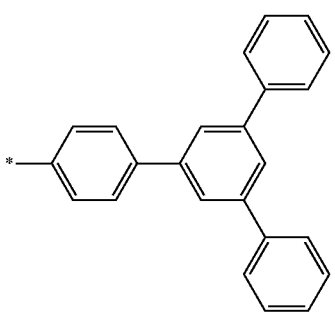

wherein, in Groups II and III, * is a linking point.

9. The composition for an organic optoelectronic device as claimed in claim 8, wherein:
Chemical Formula 2 is represented by Chemical Formula C-8 or Chemical Formula C-17 of Group II, and
*—Y¹-A¹ and *—Y²-A² of Chemical Formula 2 are selected from B-1, B-2, B-3, B-18, and B-25 of Group III.

10. The composition for an organic optoelectronic device as claimed in claim 1, wherein:
the first compound represented by Chemical Formula 1 is represented by Chemical Formula 1-Ia, Chemical Formula 1-IIa, or Chemical Formula 1-Va, and
the second compound represented by Chemical Formula 2 is represented by Chemical Formula C-8 or Chemical Formula C-17:

[Chemical Formula 1-Ia]

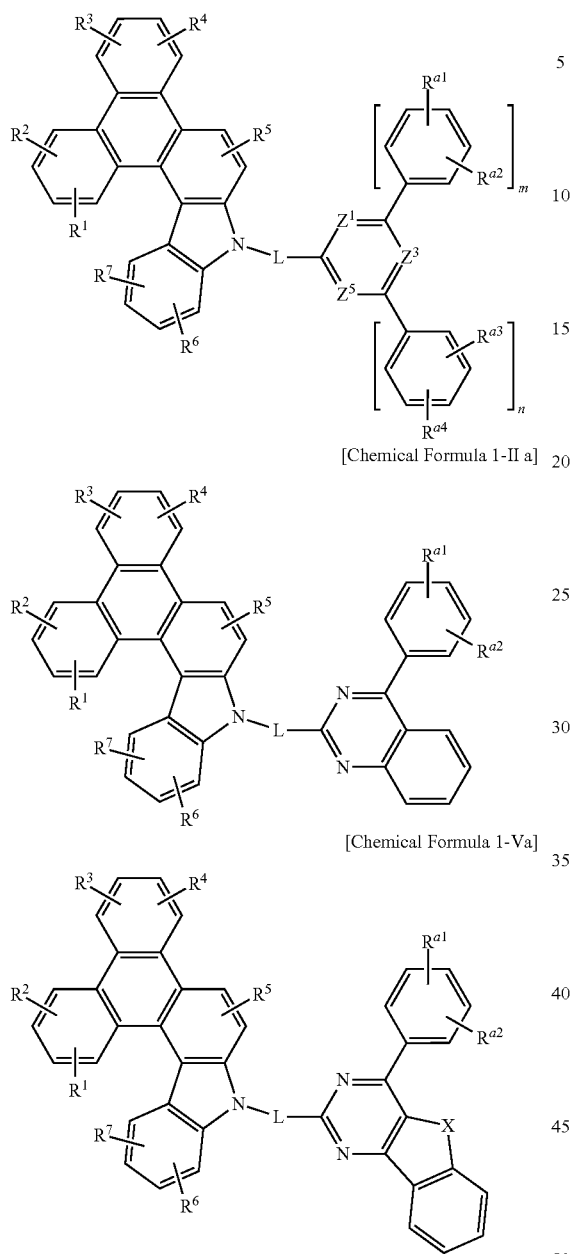

[Chemical Formula 1-IIa]

[Chemical Formula 1-Va]

wherein, in Chemical Formula 1-Ia, Chemical Formula 1-IIa, and Chemical Formula 1-Va, $Z^1$, $Z^3$, and $Z^5$ are independently N or $CR^a$, at least two of $Z^1$, $Z^3$, and $Z^5$ are N, $R^a$, $R^{a1}$, $R^{a2}$, $R^{a3}$, $R^{a4}$, and $R^1$ to $R^7$ are independently hydrogen, a substituted or unsubstituted phenyl group, a substituted or unsubstituted biphenyl group, or a substituted or unsubstituted naphthyl group, L is a single bond, a substituted or unsubstituted phenylene group, or a substituted or unsubstituted biphenylene group, m and n are independently an integer of 0 or 1, and X is O or S;

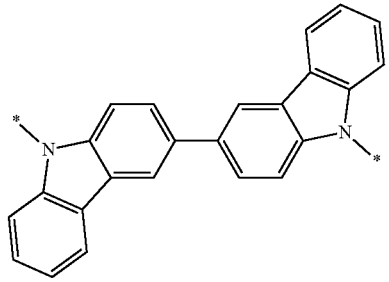

C-8

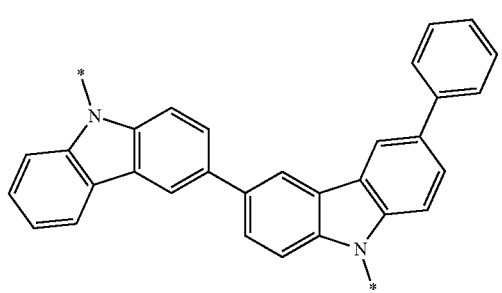

C-17

11. An organic optoelectronic device, comprising
   an anode and a cathode facing each other, and
   at least one organic layer disposed between the anode and the cathode,
   wherein the organic layer includes the composition for an organic optoelectronic device as claimed in claim 1.

12. The organic optoelectronic device as claimed in claim 11, wherein:
   the organic layer includes a light emitting layer, and
   the light emitting layer includes the composition for an organic optoelectronic device.

13. The organic optoelectronic device as claimed in claim 12, wherein the composition for an organic optoelectronic device is included as a host of the light emitting layer.

14. A display device comprising the organic optoelectronic device as claimed in claim 11.

* * * * *